United States Patent
Jaskiewicz et al.

(10) Patent No.: US 10,907,166 B2
(45) Date of Patent: Feb. 2, 2021

(54) METHOD FOR IDENTIFYING SUBSTANCES WHICH PRIME CELLS FOR A STRESS RESPONSE AND CELLS FOR USE IN THIS METHOD

(71) Applicant: Rheinisch-Westfälische Technische Hochschule Aachen, Aachen (DE)

(72) Inventors: Michal Jaskiewicz, Aachen (DE); Uwe Conrath, Kelmis (BE)

(73) Assignee: Bayer CropScience Aktiengesellschaft, Monheim (DE)

( * ) Notice: Subject to any disclaimer, the term of this patent is extended or adjusted under 35 U.S.C. 154(b) by 267 days.

(21) Appl. No.: 14/899,344

(22) PCT Filed: Jun. 12, 2014

(86) PCT No.: PCT/EP2014/062266
§ 371 (c)(1),
(2) Date: Dec. 17, 2015

(87) PCT Pub. No.: WO2014/202463
PCT Pub. Date: Dec. 24, 2014

(65) Prior Publication Data
US 2016/0130591 A1 May 12, 2016

(30) Foreign Application Priority Data
Jun. 17, 2013 (EP) ..................... 13172304

(51) Int. Cl.
*C12N 15/82* (2006.01)
*G01N 33/50* (2006.01)

(52) U.S. Cl.
CPC ..... *C12N 15/8209* (2013.01); *G01N 33/5097* (2013.01)

(58) Field of Classification Search
None
See application file for complete search history.

(56) References Cited

U.S. PATENT DOCUMENTS

| 4,407,956 A | 10/1983 | Howell |
| 4,536,475 A | 8/1985 | Anderson |
| 2016/0130591 A1 | 5/2016 | Jaskiewicz et al. |

FOREIGN PATENT DOCUMENTS

| EP | 0 067 553 | 12/1982 |
| EP | 3 010 329 B1 | 11/2019 |
| WO | WO 93/03161 | 2/1993 |
| WO | WO 95/34668 | 12/1995 |

OTHER PUBLICATIONS

Jaskiewicz et al. (EMBO Reports, 12:50-55; Jan. 2011).*
Kim et al.( Plant Molecular Biology, 24:105-117, 1994). (Year: 1994).*
Donald et al. (EMBO J. 9:1717-1726, 1990). (Year: 1990).*
Benfey et al. (Science 250:959-966, 1990). (Year: 1990).*
Liu et al. (Annu. Rev. Plant Biol. 61:395-420,2010) (Year: 2010).*
Besser et al. (FEBS Letters, 269:358-362, 1990). (Year: 1990).*
Mathieu et al. (The Plant Journal, 29:313-323, 2002) (Year: 2002).*
Jaskiewicz et al. (EMBO Reports, 12:50-55; Jan. 2011). (Year: 2011).*
Ueda et al. (Plant Mol. Biol. 67:683-697, 2008).*
Bang et al. (Plant Physiol., 142:586-594; 2006).*
Gutterson (HortScience 30:964-966,1995).*
Bruening (Proc. Natl. Acad. Sci., 95:13349-13351, 1998).*
Colliver et al. (Plant molecular Biology, 35:509-522, 1997).*
Elomaa et al. (Molecular Breeding, 2:41-50, 1996).*
Emery et al. (Current Biology 13:1768-1774, 2003).*
Arziman et al. (Nucleic Acids Research, 33:582-588, 2005).*
Bonawitz et al.,(Annu. Rev. Genet. 44: 337-363, 2010).*
Paul et al. (Plant Cell Reports; 35:1417-1427; 2016).*
Matsuda et al. (The Plant Journal, 57:96-108, 2009).*
Osborne et al. (NCBI, Gen Bank Sequence Accession No. AC000375.1; Published Jun. 9, 1997).*
Tamaoki et al. (Plant Signaling & Behavior 8:6, e24260; Jun. 2013).*
Robatzek et al. (The Plant Journal, 28:123-133, 2001).*
Koiwa et al. (PNAS, 99:10893-10898, 2002).*
Christiansen et al., "Negative regulation of defence signaling pathways by the EDR1 Protein kinase," Mol. Plant. Pathol. vol. 12 No. 8, pp. 746-758; (2011).
Conrath et al., "Priming: Getting Ready for Battle," Mol. Plant. Microbe Interact. vol. 19, No. 10, pp. 1062-1071 (2006).
Ding et al., "Multiple exposures to drought 'train' transcriptional responses in *Arabidopsis*," Nature Communications 3: 740, pp. 1-9 (2012).
Haring et al., "Chromatin immunoprecipitation: optimization, quantitative analysis and data normalization," Plant Methods; vol. 3; pp. 11-27 (2007).
Hase et al., "Colonization of *Arabidopsis* roots by Pseudomonas fluorescens primes the plant to produce higher levels of ethylene upon pathogen infection," Physiological and Molecular Plant Pathology; vol. 62, No. 4, pp. 219-226 (Apr. 2003).

(Continued)

*Primary Examiner* — Vinod Kumar
(74) *Attorney, Agent, or Firm* — Jenkins, Wilson, Taylor & Hunt, P.A.

(57) ABSTRACT

The present invention relates to a transgenic eukaryotic cell or non-human organism comprising one or more genetic modifications providing the activation of one or more signal transduction pathways which are involved in stress-induced gene expression and/or the pre-activation of one or more members of the transcriptional machinery and an expression cassette which comprises a nucleic acid sequence coding for a reporter protein under the control of a promoter the methylation of which increases upon priming for a stress response. The present invention also relates to a method for identifying substances which prime eukaryotic cells for a stress response by using this transgenic cell or organism.

6 Claims, 1 Drawing Sheet
Specification includes a Sequence Listing.

(56) References Cited

OTHER PUBLICATIONS

Hayes, et al., "Regulaton of Interferon Production by Human Monocytes: Requirements for Priming for Lipopolysaccharide-Induced Production," J. Leukocyte Bioi., vol. 50, pp. 176-181 (1991).
Hayes et al., "Regulation of Interleukin-12 Expression in Human Monocytes: Selective Priming by Interferon-γ of Lipopolysaccharide-Induced p35 and p40 Genes," Blood vol. 86, pp. 646-650 (1995).
Koiwa et al., "C-terminal domain phosphatase-like family members (AtCPLs) differently regulate *Arabidopsis thaliana* abiotic stress signaling, growth, and development," Proc. Natl. Acad. Sci. USA; vol. 99; No. 16; pp. 10893-10898 (2002).
Li et al., "The WRKY70 Transcription Factor: A Node of Convergence for Jasmonate-Mediated and Salicylate-Mediated Signals in Plant Defense," The Plant Cell, vol. 16, pp. 319-331 (2004).
Mosher et al., "A comprehensive Structure-Function Analysis of *Arabidopsis* SNI1 Defines Essential Regions and Transcriptional Repressor Activity," The Plant Cell, vol. 18, No. 25, pp. 1750-1765 (2006).
Shim et al., "AtMYB44 regulates WRKY70 expression and modulated antagonistic interaction between salicyclic acid and jasmonic acid signaling,"The Plant J. 73: 483-495; (2013).
Thesis of Enrico Gobbato, "Analysis of mechanisms underlying EDSI-PAD4 cooperation in *Arabidopsis* immune signaling," University of Cologne, pp. 1-138 (2007).
Ueda et al., "The *Arabidopsis thaliana* carboxyl-terminal domain phosphatase-like 2 regulates plant growth, stress and auxin responses," Plant Mol. Bioi. vol. 67; pp. 683-697 (2008).
Wada et al., "DSIF, a novel transcription elongation factor that regulates RNA polymerase II processivity, is composed of human Spt4 and Spt5 homologs," Genes Dev. 12:343-356 (1998).
Alvarez-Venegas et al. (2007) Epigenetic Control of a Transcription Factor at the Cross Section of Two Antagonistic Pathways. Epigenetics 2(2):106-113.
Ding et al. (2012) Supplemental Figures and Supplementary Table. 1-4.
Office Action corresponding to European patent application No. 14 731 582.4 dated Dec. 18, 2017.
Quintin et al. (2012) *Candida albicans* Infection Affords Protection against Reinfection via Functional Reprogramming of Monocytes. Cell Host Microbe 12(2):1-15.
Official Action corresponding to European patent application serial No. 14731582.4 dated Mar. 20, 2017.
Alle Biotechnology—Innovative Technology Groundbreaking Results, Home Page, http://www.allelebiotech.com, p. 1, copyright 2016 (Accessed Nov. 30, 2016).
Beckers et al., "Mitogen-Activated Protein Kinases 3 and 6 Are Required for Full Priming of Stress Responses in *Arabidopsis thaliana*," The Plant Cell, vol. 21, pp. 944-953 (Mar. 2009).
Chen et al., "Potentiation of Developmentally Regulated Plant Defense Response by AtWRKY18, a Pathogen-Induced *Arabidopis* Transcription Factor," Plant Physiol., vol. 129; pp. 706-716 (2002).
Communication of the extended European Search report for European Patent Application No. 13172304.1 dated Nov. 12, 2013.
Conrath, "Priming of Induced Plant Defense Responses," Advances in Botanical Research, vol. 51, pp. 361-695 (Jan. 2009).
Conrath, "Molecular aspects of defence priming," Trends in Plant Science, vol. 16, No. 10, pp. 524-531 (Oct. 2011).
Eurasian *Arabidopsis* Stock Centre (uNASC), Home Page, http://http://arabidopsis.info/, The University of Nottingham, p. 1 (Accessed Nov. 30, 2016).
Interntional Search Report corresponding to International Patent Application No. PCT/EP2014/062266 dated Sep. 16, 2014.
Jaskiewicz et al., "Chromatin modication acts as a memory for systemic acquired resistance in the plant stress response," EMBO Reports, vol. 12, No. 1, pp. 50-55 (Jan. 2011).
Jaskiewicz et al., "Mechanisms of gene regulation in the primed stress response of *Arabidopsis thaliana*," pp. 1-129 (2013).
Koiwa et al., "*Arabidopsis* C-terminal domain phosphatase-like 1 and 2 are essential Ser-5-specific C-terminal domain phosphatases," Proc. Natl. Acad. Sci. USA, vol. 101, No. 40; pp. 14539-14544 (Oct. 5, 2004).
Noutoshi et al., "Novel Plant Immune-Priming Compounds Identified via High-Throughput Chemical Screening Target Salicyclic Acid Glycosyltransferasas in *Arabidopsis* ", The Plant Cell, vol. 24, pp. 3795-3804 (Sep. 2012).
Po-Wen et al., "Priming of the *Arabidopsis* pattern-triggered immunity response upon infection by necrotrophic Pectobacterium carotovorum bacteria," Molecular Plant Pathology, vol. 14, No. 1, pp. 58-70 (2013).
Clough et al., "Floral dip: a simplified method for *Agrobacterium*-mediated transformation of *Arabidopsis thaliana*," Plant Journal, vol. 16, No. 6, pp. 735-743 (1998).
IPRP and Written Opinon corresponding to International Patent Application No. PCT/EP2014/062266 dated Dec. 22, 2015.
Pieterse et al., "Networking by small-molecule hormones in plant immunity," Nature Chemical Biology, vol. 5, No. 5, pp. 308-316 (May 2009).
Saleh et al., "Dynamic and stable histone H3 methylation patterns at the *Arabidopsis* FLC and AP1 loci," Gene, vol. 423, Issue 1, pp. 43-47, Oct. 15, 2008 (Abstract).

* cited by examiner

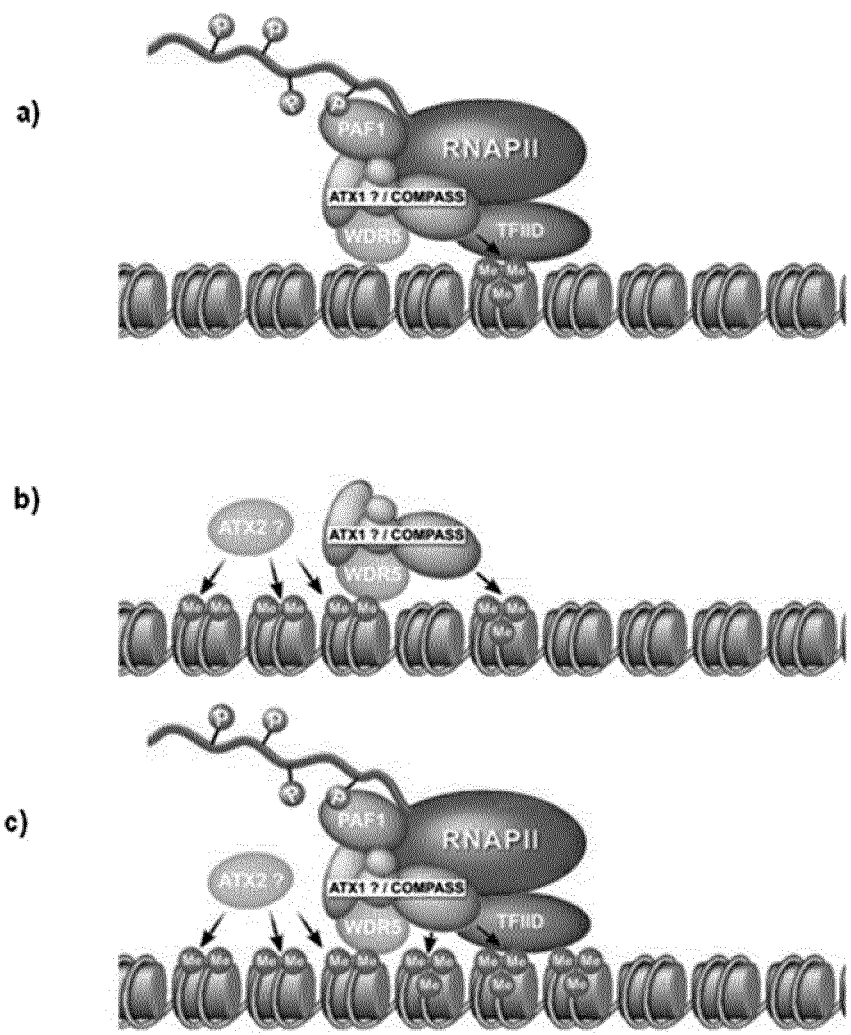

US 10,907,166 B2

METHOD FOR IDENTIFYING SUBSTANCES WHICH PRIME CELLS FOR A STRESS RESPONSE AND CELLS FOR USE IN THIS METHOD

FIELD OF THE INVENTION

The present invention relates to a transgenic eukaryotic cell or non-human organism comprising one or more genetic modifications providing the activation of one or more signal transduction pathways which are involved in stress-induced gene expression and/or the pre-activation of the transcriptional machinery and an expression cassette which comprises a nucleic acid sequence coding for a reporter protein under the control of a promoter the methylation of which increases upon priming for a stress response. The present invention also relates to a method for identifying substances which prime eukaryotic cells for a stress response by using this transgenic cell or organism.

BACKGROUND OF THE INVENTION

Plant diseases which are caused by various pathogens such as viruses, bacteria, oomycetes and fungi or abiotic stress such as drought, cold, freeze and salt may lead to significant crop losses of cultivated plants, resulting in economic detriments and in threatening food and feed supply.

Since the last century, chemical pesticides have been used for controlling plant diseases. Nevertheless, at present at least 40% of the possible plant yield is lost due to diseases and abiotic stress such as drought. Hence, there is still a need for improved methods for controlling plant diseases and abiotic stresses. Due to the low acceptance of genetically modified plants in Europe and because of the increasing demand for substances which are uncritical for the environment, there is a huge interest in using natural or near-natural substances for an effective plant protection.

Natural or near-natural substances are particularly effective, if they do not only harm or kill pathogens, but also stimulate certain parts of the plant's endogenous immune system. This is particularly true for agents which act via the so-called "defence priming" (reviewed in Conrath (2011) Trends in Plant Science 16(10): 524-531; Conrath et al. (2006) Mol. Plant. Microbe Interact. 19(10): 1062-1071). Defence priming prepares the plant's endogenous immune system for a future challenge such as pathogen infection or abiotic stress, but does not directly activate immunity. It has been shown that treatment of plant cells with priming substances induce chromatin modifications on endogenous defence gene promoters that are normally found on active genes, although the genes remain inactive (Jaskiewicz et al. (2011) EMBO Reports 12(1): 50-55). However, primed plants respond to very low levels of a stimulus, such as biotic or abiotic stress, in a more rapid and robust manner than non-primed plants. Hence, pesticides which induce priming confer an increased stress resistance to plants without reducing the yield. Consequently, there is a strong demand for substances which induce defence priming in plants.

It has been shown that priming is not restricted to plant cells, but also occurs in animal cells with a similar mechanism (see, e.g., Hayes et al. (1991) J. Leukocyte Biol. 50: 176-181). For example, interferon-γ or GM-CSF can prime the induction of the expression of the cytokines interferon-α, interferon-β, tumour necrosis factor α and IL-12 which cytokines are involved in the overall defence response (Hayes et al. (1995) Blood 86: 646-650). The induction of cytokine expression is mediated by signal transduction through p38 and ERK1/2 kinases.

However, since the priming process does not lead to a direct activation of the defence mechanisms, the search for substances which act via priming is rather difficult. So far, no system for the direct screening for priming compounds is known which is easy to handle and based on the use of plants. In the methods of the prior art, the cells have to be stimulated twice to be able to determine whether they were in a primed state after treatment with a specific substance. The first stimulus by a substance to be tested primes the cell, for example for gene expression and the second stimulus, e.g. an infection with a pathogen, induces the actual defence reaction which is used as a read-out system in this method to determine whether the substance induces priming or not. Both the first and the second stimulus are necessary to determine whether the cells were in a primed state after treatment with the substance to be tested. Such a system is described in Noutoshi et al. (2012) Plant Cell 24(9): 3795-3804 where *Arabidopsis* MM1 cell suspension cultures were first treated with potential immune-priming substances and then with bacteria Pst-avrRpm1, before immune-related cell death was measured by staining the dead plant cells with Evans blue dye. Hence, this system necessarily involves the death of plant cells.

Consequently, there is still a need for a method which enables the direct identification of substances which prime cells or organisms for a stress response in one treatment step and with a convenient read-out system.

OBJECT AND SUMMARY OF THE INVENTION

It is thus an object of the present invention to provide a method for identifying substances which prime cells or organisms for a stress response and to provide transgenic cells or organisms for use in this method.

These and further objects of the invention, as will become apparent from the description, are attained by the subject-matter of the independent claims.

Some of the preferred embodiments of the present invention form the subject-matter of the dependent claims.

The present inventors have found that in the induction of an enhanced stress-activated gene response after priming of plants two molecular events are involved:
(1) an epigenetic alteration, i.e. an increase in the methylation of histone H3 in promoters regulating the expression of genes which are involved in the defence response, and
(2) the activation of one or more signal transduction events involved in stress-induced gene expression or the pre-activation of the transcriptional machinery.

In the method of the present invention the activation of one or more signal transduction pathways involved in stress-induced gene expression or the pre-activation of the transcriptional machinery mimics the stress stimulus which induces the defence reaction, i.e. the expression of genes involved in the defence response. Hence, in the method of the present invention only one stimulus, i.e. the treatment with a substance which is supposed to induce the priming is required to determine whether this substance induces priming or not. Consequently, it was possible to develop a simple method for directly identifying substances which induce the priming of cells.

Accordingly, the present invention provides a transgenic eukaryotic cell or non-human organism comprising:
a) one or more genetic modifications providing the activation of one or more signal transduction pathways which are involved in stress-induced gene expression and/or the pre-activation of one or more members of the transcriptional machinery; and b) an expression cassette which comprises:
  (i) a promoter the methylation of which increases upon priming for a stress response or a functional fragment or functional derivative of such a promoter;
  (ii) operatively linked thereto a nucleic acid sequence coding for a reporter protein; and
  (iii) optionally, further regulatory elements.

Preferably, the one or more genetic modifications providing the activation of one or more signal transduction pathways which are involved in stress-induced gene and/or the pre-activation of one or more members of the transcriptional machinery lead to an altered expression or activity of a protein selected from the group consisting of RNA polymerase II, EDR1, MKP1, MKP2, MPK4, EDS1, PAD4, WRKY70, WRKY18, MYB44, SPT4, SPT5 and SNI1.

More preferably, the one or more genetic modifications lead to an increased expression or activity of RNA polymerase II. Even more preferably, the RNA polymerase II is constitutively phosphorylated and most preferably the RNA polymerase II is constitutively phosphorylated by reducing the activity of a phosphatase capable of dephosphorylating RNA polymerase II.

The promoter the methylation of which increases upon priming for a stress response may be the promoter of a gene selected from the group consisting of: WRKY6, WRKY29, WRKY70, WRKY53, PR1, PAL1, PAL2, 4CL, C4H, RD29B, RAB18, P5CS1, LPT3, LPT4, HSFA6A, HIPP22, WRKY38, PR5, ICS1, WRKY31, HEL, PDF1-2, p35, p40, tumour necrosis factor α, interferon-α and interferon-β or a functional fragment or functional derivative of any of these promoters.

The reporter protein may be selected from the group consisting of: fluorescent proteins, luciferase proteins, β-galactosidase, alkaline phosphatase, β-glucuronidase and chloramphenicol acetyltransferase.

The transgenic eukaryotic cell or non-human organism may be a plant cell or plant organism, preferably the plant cell is from an *Arabidopsis thaliana* plant or the plant organism is an *Arabidopsis thaliana* plant.

If the transgenic eukaryotic cell or non-human organism is a plant cell or plant organism, preferably an *Arabidopsis thaliana* cell or an *Arabidopsis thaliana* plant, the promoter the methylation of which increases upon priming for a stress response may be the promoter of a gene selected from the group consisting of: WRKY6, WRKY29, WRKY70, WRKY53, PR1, PAL1, PAL2, 4CL, C4H, RD29B, RAB18, P5CS1, LPT3, LPT4, HSFA6A, HIPP22, WRKY38, PR5, ICS1, WRKY31; HEL, PDF1-2 or a functional fragment or a functional derivative of any of these promoters.

In an alternative embodiment the transgenic eukaryotic cell or non-human organism may be an animal cell or a non-human animal organism, preferably a mammalian cell and more preferably a rodent or human cell.

If the transgenic eukaryotic cell or non-human organism is an animal cell or a non-human animal organism, preferably a mammalian cell and more preferably a rodent or human cell, the promoter the methylation of which increases upon priming for a stress response may be the promoter of a gene selected from the group consisting of: p35, p40, tumour necrosis factor α, interferon-α and interferon-β or a functional fragment or functional derivative of any of these promoters.

The present invention also relates to a transgenic plant cell or plant organism comprising:

(a) one or more genetic modifications leading to an altered expression or activity of a protein selected from the group consisting of RNA polymerase II, EDR1, MKP1, MKP2, MPK4, EDS1, PAD4, WRKY70, WRKY18, MYB44, SPT4, SPT5 and SNI1; and
(b) an expression cassette which comprises the following elements in 5' to 3' direction:
  (i) a promoter of a gene selected from the group consisting of: WRKY6, WRKY29, WRKY70, WRKY53, PR1, PAL1, PAL2, 4CL, C4H, RD29B, RAB18, P5CS1, LPT3, LPT4, HSFA6A, HIPP22, WRKY38, WRKY31, PR5, ICS1, HEL, PDF1-2 or a functional fragment or functional derivative of any of these promoters;
  (ii) operatively linked thereto a nucleic acid sequence coding for a reporter protein; and
  (iii) optionally, a transcription termination sequence.

In another embodiment, the present invention relates to a transgenic plant cell or plant organism comprising:

a) a genetic modification resulting in the constitutive phosphorylation of RNA polymerase II; and
b) an expression cassette which comprises the following elements in 5' to 3' direction:
  (i) a promoter of a gene selected from the group consisting of: WRKY6, WRKY29, WRKY70, WRKY53, PR1, PAL1, PAL2, 4CL, C4H, RD29B, RAB18, P5CS1, LPT3, LPT4, HSFA6A, HIPP22, WRKY38, PR5, ICS1, WRKY31, HEL, PDF1-2 or a functional fragment or functional derivative of any of these promoters;
  (ii) operatively linked thereto a nucleic acid sequence coding for a reporter protein; and
  (iii) optionally, a transcription termination sequence.

Preferably, the modification resulting in the constitutive phosphorylation of RNA polymerase II is a reduction of activity of a phosphatase capable of dephosphorylating RNA polymerase II.

Preferably, the phosphatase is CPL1 or CPL3 and more preferably the phosphatase has the nucleic acid sequence according to SEQ ID No. 1 or 2.

In a preferred embodiment the activity of the phosphatase is reduced by a T-DNA insertion or chemically induced mutation which leads to a reduction of phosphatase expression, by RNA interference, by miRNA, by an aptamer, by an antibody specifically binding to the phosphatase, by an antisense sequence, by TILLING, by TALENs or by post-transcriptional gene silencing, more preferably it is reduced by a T-DNA insertion which leads to a reduction of phosphatase expression and most preferably the T-DNA insertion is the one present in the plants obtainable from The European *Arabidopsis* Stock Centre under a catalogue number selected from the group consisting of N6541, N415837, N481418, N861773, N865879 and N6542.

Preferably, the promoter is the promoter of the WRKY6 gene and more preferably it has the sequence according to SEQ ID No. 6 or is a functional fragment or functional derivative thereof.

Hence, the present invention in particular relates to a transgenic plant cell or plant organism comprising:
(a) a T-DNA insertion which leads to a reduction of expression of a phosphatase which is capable of dephosphorylating RNA polymerase II; and
(b) an expression cassette which comprises the following elements in 5' to 3' direction:
  (i) a promoter of the WRKY6 gene or a functional fragment or functional derivative of this promoter;
  (ii) operatively linked thereto a nucleic acid sequence coding for a reporter protein; and
  (iii) optionally, a transcription termination sequence.

In still another embodiment, the present invention relates to a method for identifying substances which prime eukaryotic cells for a stress response, comprising the steps of:
 a) treating the transgenic eukaryotic cell or non-human organism or the transgenic plant cell or plant organism of the present invention with one or more candidate substances; and
 b) determining expression of the reporter gene.

Hence, in particular the present invention relates to a method for identifying substances which prime eukaryotic cells for a stress response, comprising the steps of:
 (a) treating a transgenic plant cell or plant organism comprising:
  (i) a T-DNA insertion which leads to a reduction of expression of a phosphatase which is capable of dephosphorylating RNA polymerase II; and
  (ii) an expression cassette which comprises the following elements in 5' to 3' direction:
   a promoter of the WRKY6 gene or a functional fragment or a functional derivative of this promoter;
   operatively linked thereto a nucleic acid sequence coding for a reporter protein; and
   optionally, a transcription termination sequence, with one or more candidate substances; and
 (b) determining expression of the reporter gene.

The transgenic cell or non-human organism may be treated with the one or more candidate substances for a period between 6 hours and 5 days, preferably 10 hours to 4 days, more preferably 12 hours to 3 days and most preferably 48 to 72 hours.

Finally, the present invention relates to the use of the transgenic eukaryotic cell or non-human organism or the transgenic plant cell or plant organism of the present invention for the identification of substances which prime cells for a stress response.

BRIEF DESCRIPTION OF THE DRAWINGS

FIG. 1: Hypothetical model of priming and transcription-associated methylation on the WRKY6 promoter
a) After stress stimulus, without priming: During normal transcription lysine 4 of histone 3 (H3K4) becomes trimethylated (H3K4me3) by a methyltransferase complex that is recruited and activated by phosphorylated RNA polymerase II (RNAPII).
b) After priming: H3K4 becomes dimethylated and the WDR5 protein of the methyltransferase complex recruits H3K4me3 to chromatin.
c) Stress stimulus after priming: During primed transcription the combination of WDR5-dependent coupling of the H3K4me3 methyltransferase and the phosphorylation of RNA polymerase II both lead to a high trimethylation of the promoter and enhanced transcription.

DETAILED DESCRIPTION OF THE INVENTION

The present invention as illustratively described in the following may suitably be practiced in the absence of any element or elements, limitation or limitations, not specifically disclosed herein.

The present invention will be described with respect to particular embodiments, but the invention is not limited thereto, but only by the claims.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group which preferably consists only of these embodiments.

For the purposes of the present invention, the term "obtained" is considered to be a preferred embodiment of the term "obtainable". If hereinafter e.g. a cell or organism is defined to be obtainable by a specific method, this is also to be understood to disclose a cell or organism which is obtained by this method.

Where an indefinite or definite article is used when referring to a singular noun, e.g. "a", "an" or "the", this includes a plural of that noun unless something else is specifically stated.

The term "transgenic" means that a cell or organism has been altered using recombinant DNA technology to contain a nucleic acid sequence which would otherwise not be present in said cell or organism. Within the present invention, the transgenic cell or organism contains a nucleic acid sequence coding for a reporter protein which is operably linked to a promoter to which the nucleic acid sequence is not linked in the genome of a non-transgenic cell or organism. The transgenic eukaryotic cell or non-human organism also contains a further modification by recombinant DNA technology which leads to the activation of one or more members of a signal transduction pathway leading to stress-induced gene expression or the pre-activation of one or more members of the transcriptional machinery, such as RNA polymerase II. Preferably, the genetic modification leads to the constitutive phosphorylation of RNA polymerase II.

Eukaryotic cells are characterized by a nucleus which is surrounded by a membrane and which distinguishes the eukaryotic cells from prokaryotic cells. In particular, eukaryotic cells include animal cells, plant cells and fungal cells. Preferably, the cells of the present invention are plant cells.

The term "cell" as used herein refers to a single cell and also includes a population of cells. The population may be a pure population comprising one cell type. Likewise, the population may comprise more than one cell type. A cell within the meaning of the invention may be isolated (e.g., in suspension culture) or comprised in a tissue, organ or organism at any developmental stage, such as a plant tissue, plant organ or plant organism.

The term "organism" as used herein refers to a living system which is capable of responding to stimuli, of reproduction, of growth and of development. An organism usually consists of many cells which are grouped into specialized tissues and organs. Preferably, the eukaryotic organism of the present invention is a plant organism.

The term "genetic modification" refers to the alteration of the genetic material of a cell or organism, which genetic modification is preferably stable so that it is inherited to future generations. By this genetic modification the genome of a transgenic cell can be distinguished from the genome of a non-transgenic cell.

The term "signal transduction pathway which is involved in stress-induced gene expression" is intended to include all proteins which are involved in the transduction of a stress stimulus from the extracellular membrane to the cell nucleus via a signaling cascade, thereby leading to the induction of gene expression. In particular, the signal transduction pathway includes signal transduction molecules such as adaptor proteins, GTPases, kinases and phosphatases. The skilled person knows the members of the signal transduction pathways leading to stress-induced gene expression.

The signal transduction pathway which is involved in stress-induced gene expression is activated, if the stress-induced gene expression occurs earlier and/or to a higher extent after an additional stress stimulus than the stress-induced gene expression without activated signal transduction pathway leading to stress-induced gene expression. Usually, the members of the signal transduction pathway will be in a state which is the same as after stimulation of the cell with a stimulus which leads to the activation of the signal transduction pathway. For example, if a stress leads to the activation of a kinase present in the signal transduction pathway, the signal transduction pathway is activated in the cells of the present invention if the kinase is active without the stimulus. Alternatively, if a stress stimulus leads to the inactivation of a repressor or negative regulator, the signal transduction pathway is activated, if the function of this repressor or negative regulator is reduced or eliminated.

The term "members of the transcriptional machinery" is intended to include regulators of transcription, such as specific transcription factors, basal transcription factors, repressors and enhancers as well as RNA polymerase II which regulators are necessary to obtain gene expression and which regulators are differentially modified or bound to the DNA during the transcription cycle. Preferably, the members of the transcriptional machinery are transcriptional regulators which are able to bind to multiple promoters or at least to several promoters which are involved in stress responses.

The members of the transcriptional machinery are in a "pre-activated state", if the transcription occurs earlier and/or to a higher extent after an additional stimulus than the transcription without pre-activated members of the transcriptional machinery. For example, in the pre-activated state one or more transcription factors or other transcription-stimulating factors may already be bound to regulatory regions of a gene without activating transcription. Preferably, the member of the transcriptional machinery is RNA polymerase II and more preferably the RNA polymerase II is constitutively phosphorylated.

Preferably, the one or more genetic modifications providing the activation of one or more signal transduction pathways which are involved in stress-induced gene expression and/or the pre-activation of the transcriptional machinery leads to an altered expression or activity of one or more proteins selected from the group consisting of RNA polymerase II, EDR1, MKP1, MKP2, MPK4, EDS1, PAD4, WRKY70, WRKY18, MYB44, SPT4, SPT5 and SNI1.

SPT4 and SPT5 are subunits of the negative elongation factor which cause the RNA polymerase to stay on the promoter without starting transcription (Wada et al. (1998) Genes Dev. 12: 343-356). Hence, the inhibition of the expression or activity of SPT4 and/or SPT5 will result in an activation of transcription.

SNI1 is a transcription factor which acts as negative regulator of stress responses in Arabidopsis thaliana (Mosher et al. (2006) The Plant Cell 18: 1750-1765). Hence, a reduced expression or activity of SNI1 will result in an activation of stress-induced transcription.

EDS1, PAD4, WRKY and MYB transcription factors are positive regulators of a stress response so that their expression leads to an activation of stress-induced gene expression (Li et al. (2004) The Plant Cell 16: 319-331; Chen and Chen (2002) Plant Physiol. 129: 706-716; Shim et al. (2013) The Plant J. 73: 483-495; Thesis of Enrico Gobbato at the University of Cologne (2007)).

More preferably, the member of a signal transduction pathway which is involved in stress-induced gene expression or the member of the transcriptional machinery is RNA polymerase II and/or EDR1, and most preferably it is RNA polymerase II.

EDR1 is a protein kinase which negatively regulates defense signaling pathways (Christiansen et al. (2011) Mol. Plant. Pathol. 12(8): 746-758). Hence, inhibition of EDR1 expression or activity will result in an activation of stress-induced transcription.

RNA polymerase II is a core component of the transcription complex which catalyses mRNA synthesis and is also involved in the regulation of various mRNA maturation processes, such as capping, splicing and poly-adenylation. The largest subunit of RNA polymerase II contains a C-terminal domain which is composed of up to 52 repeats of the heptapeptide sequence YSPTSPS (SEQ ID No. 67) which repeats are essential for polymerase activity. It has been shown that the function of RNA polymerase II is determined by the phosphorylation status of the C-terminal domain. During the transcription cycle the repeats of the C-terminal domain are differentially phosphorylated, predominantly at serine 2 or serine 5.

In the transgenic cells and the method of the present invention, the RNA polymerase II is preferably constitutively phosphorylated. The term "constitutively phosphorylated" is intended to mean that the phosphorylation is constant and not significantly influenced by external stimuli. The phosphorylation status can be detected by immunoprecipitating the RNA polymerase II with a suitable antibody such as an antibody directed to RNA polymerase II and detecting the phosphorylation of the protein with a phospho-specific antibody, such as an antibody directed to phospho-serine.

The skilled person is aware of methods for obtaining a constitutively phosphorylated RNA polymerase II. These methods include the overexpression of a kinase which is capable of phosphorylating RNA polymerase II, for example mitogen-activated protein kinase 3. It has been shown that RNA polymerase II is phosphorylated by mitogen-activated protein kinase 3 (Ueda et al. (2008) Plant Mol. Biol. 67:683-697). Further, this kinase was shown to the required for full priming in Arabidopsis thaliana (Beckers et al. (2009) Plant Cell 21:944-953). Another kinase which may be involved in the phosphorylation of RNA polymerase II may be mitogen-activated protein kinase 6 (MPK6).

Methods for the overexpression of proteins are known to the person skilled in the art. For example, the coding region of the protein may be operably linked to a promoter which shows strong and constitutive activity in the cells to be transformed and the resulting expression construct may be transformed into the host cells.

Another alternative for obtaining constitutively phosphorylated RNA polymerase II is to reduce or inhibit the activity of a phosphatase which is capable of dephosphorylating RNA polymerase II. Such phosphatases include, but are not limited to C-terminal domain phosphatase-like (CPL) 1 and 3 (see Koiwa et al. (2002) Proc. Natl. Acad. Sci. USA 99 (16): 10893-10898; Koiwa et al. (2004) Proc. Natl. Acad. Sci. USA 101 (40): 14539-14544). The nucleic acid sequences coding for CPL1 and CPL3 are depicted in SEQ ID Nos. 1 and 2.

The skilled person knows methods to reduce the expression of a certain protein, including, but not being limited to, T-DNA insertion which leads to a reduction of phosphatase expression, by RNA interference, by miRNA, by an aptamer, by an antibody specifically binding to the phosphatase, by an antisense sequence or by post-transcriptional gene silencing. Further methods include the expression of a ribozyme which specifically recognizes the nucleic acid sequence coding for the protein or the expression of ribonuclease P (RNAseP) together with a leading sequence which directs RNAseP to the mRNA of the protein. Further, the skilled person knows many techniques for suppressing or inhibiting the expression of an endogenous gene by a small double-stranded RNA molecule, so called small interfering RNAs or siRNAs.

Another possibility would be to integrate a nucleic acid sequence for reducing the expression of the phosphatase into the natural locus of the sequence by targeted homologous recombination. The activity may also be reduced by the targeted induced local lesions in genomes (TILLING) method or by transcription activator-like effector nucleases (TALENs).

Preferably, the activity of the phosphatase is reduced by a T-DNA insertion into the coding sequence of the phosphatase which insertion leads to an abrogation of expression of said phosphatase. Plants carrying such an insertion are known to the skilled person (Koiwa et al. (2002) Proc. Natl. Adad. Sci. USA 99 (16): 10893-10898; Koiwa et al. (2004) Proc. Natl. Acad. Sci USA 101 (40): 14539-14544). Such plants can be obtained, for example, from The European *Arabidopsis* Stock Center (arabidopsis.info; Nottingham *Arabidopsis* Stock Centre, School of Biosciences, University of Nottingham, Sutton Bonington Campus, Loughborough, LE12 5RD United Kingdom) under any of the catalogue numbers N6541, N415837, N481418, N861773, N865879, N6542. If such plants are used, they are transformed with a vector carrying the expression cassette comprising the promoter the methylation of which increases upon priming for a stress response operatively linked to a nucleic acid sequence coding for the reporter protein to obtain the transgenic plants or plant cells of the present invention.

Within the scope of the present invention, the term "expression cassette" means a nucleic acid molecule which contains all elements which are necessary for the expression of a nucleic acid sequence, i.e. the nucleic acid sequence to be expressed under the control of a suitable promoter and optionally further regulatory sequences such as termination sequences. An expression cassette of the present invention may be part of an expression vector which is transferred into a cell or may be integrated into the chromosome of a transgenic cell or organism after transformation.

As used herein, the term "vector" refers to a nucleic acid molecule capable of transporting another nucleic acid to which it has been linked and may be used herein interchangeably with the term "recombinant nucleic acid molecule". One type of vector is a "plasmid", which refers to a circular double stranded DNA loop into which additional DNA segments can be ligated. In the present specification, "plasmid" and "vector" can be used interchangeably as the plasmid is the most commonly used form of vector. For the transformation of plants, the vector can be a binary vector or a T-DNA that comprises a left and a right border and may include a gene of interest in between. The term "expression vector" means a vector capable of directing expression of a particular nucleotide sequence in an appropriate host cell. An expression vector comprises a regulatory nucleic acid element operably linked to a nucleic acid of interest, which is—optionally—operably linked to a termination signal and/or other regulatory element.

The term "promoter" as used herein refers to a DNA sequence which, when ligated to a nucleotide sequence of interest, is capable of controlling the transcription of the nucleotide sequence of interest into mRNA. A promoter is typically, though not necessarily, located 5' (e.g., upstream) of a nucleotide sequence of interest (e.g., proximal to the transcriptional start site of a structural gene) whose transcription into mRNA it controls, and provides a site for specific binding by RNA polymerase and other transcription factors for initiation of transcription.

The methylation of histones on the promoter used in the present invention increases upon priming for a stress response, i.e. when the cell is treated with a substance which primes the cell for a stress response, the methylation of the histones present in the chromatin of the promoter used in the expression cassette of the present invention increases compared to the methylation of the histones present in the chromatin of the promoter of an untreated cell. The methylation of a promoter can for example be detected by chromatin immunoprecipitation (ChIP) which involves the cross-linking of proteins bound to chromatin with chromatin, the shearing of chromatin to produce smaller fragments, the precipitation of the DNA/protein complex with an antibody which is directed to the methylated histone protein, the de-crosslinking of proteins and chromatin and determination of the DNA sequence of the DNA-fragment that was bound to the protein when the protein was immunoprecipitated by amplifying the DNA sequence with suitable DNA primers. A suitable method for chromatin immunoprecipitation from plant cells is described in Haring et al. (2007) Plant Methods 3: 11-27.

Within the meaning of the present invention the term "methylation" is intended to mean the attachment of one or more methyl residues to lysine 4 of histone H3 and includes mono-, di- and trimethylation. The promoter is preferably trimethylated after priming for a stress response, i.e. three methyl residues are attached to lysine 4 of histone H3 proteins within the chromatin of the promoter sequence. Accordingly, the terms "monomethylated" and "dimethylated" are intended to refer to the attachment of one or two methyl residues, respectively, to lysine 4 of histone H3 proteins within the chromatin of the promoter sequence The antibody which is used to detect the trimethylation of a promoter is directed to H3K4me3, i.e. histone H3 which is trimethylated on lysine 4. Such an antibody is available from Abcam (Catalogue No. ab8580) and Diagenode (Catalogue No. pAB-003-50). The antibody which is used to detect the mono-methylation of a promoter is directed to H3K4me1, i.e. histone H3 which is monomethylated on lysine 4. Such an antibody is available from Abcam (Catalogue No. ab8895). The antibody which is used to detect the dimethylation of a promoter is directed to H3K4me2, i.e. histone H3 which is dimethylated on lysine 4. Such an antibody is available from Abcam (Catalogue No. ab7766) and Upstate (Catalogue No. 07-030).

To identify promoters which are suitable for use in the present invention, i.e. promoters the methylation of which increases upon priming for a stress response, cells are treated with a substance which is known to induce histone H3 methylation and the priming for a stress response, such as benzo(1,2,3)thiadiazole-7-carbothioic acid S-methyl ester (BTH), salicylic acid (SA), beta-aminobutyric acid (BABA) or acetyl salicylic acid (aspirin) and the methylation of the promoter is detected as described above using chromatin immunoprecipitation and compared to the methylation of the promoter in an untreated cell. If the methylation of the promoters increases upon treatment with any of these substances, the promoter can be used in the present invention. Candidate promoters which can be tested for an increase in methylation after priming for a stress response are promoters which are known to be induced by exposure to biotic or abiotic stress and/or which are known to have a stronger activity or an earlier onset of activity after repeated exposure to stress.

Plant promoters for which it has been shown that their methylation increases after treatment with substances which are known to induce priming are the promoters of the WRKY29, WRKY6, WRKY70, WRKY53, PR1, PAL1, PAL2, 4CL, C4H, RD29B, RAB18, P5CS1, LPT3, LPT4, HSFA6A and HIPP22 genes (Jaskiewicz et al. (2011) EMBO Reports 12(1): 50-55; Ding et al. (2012) Nature Communications 3: 740). Hence, the promoters of the WRKY29, WRKY6, WRKY70, WRKY53, PR1, PAL1, PAL2, 4CL, C4H, RD29B, RAB18, P5CS1, LPT3, LPT4, HSFA6A and HIPP22 genes are preferred for use in plant cells of the present invention. The promoters of the WRKY29, WRKY6, WRKY70, WRKY53, PR1, RD29B, RAB18, P5CS1, LPT3, LPT4, HSFA6A and HIPP22 genes have been shown to be trimethylated after treatment with substances which are known to induce priming and are therefore particularly preferred for use in plant cells of the present invention. Further promoters which are suitable for use in plant cells of the present invention include the promoters of the WRKY38, PR5, ICS1, WRKY31, HEL and PDF1-2 genes.

The sequences of these promoters from *Arabidopsis thaliana* are depicted in SEQ ID No. 3 (WRKY29), SEQ ID No. 6 (WRKY6), SEQ ID No. 7 (WRKY70), SEQ ID No. 8 (WRKY53), SEQ ID No. 9 (PR1), SEQ ID No. 10 (PAL1), SEQ ID No. 11 (PAL2), SEQ ID No. 12 (4CL), SEQ ID No. 13 (C4H), SEQ ID No. 14 (RD29B), SEQ ID No. 15 (RAB18), SEQ ID No. 16 (P5CS1), SEQ ID No. 17 (LPT3), SEQ ID no. 18 (LPT4), SEQ ID No. 19 (HSFA6A), SEQ ID No. 20 (HIPP22), SEQ ID No. 21 (WRKY38), SEQ ID No. 22 (PR5), SEQ ID No. 23 (ICS1), SEQ ID No. 24 (WRKY31), SEQ ID No. 63 (PDF1-2) and SEQ ID No. 64 (HEL).

Promoters from animal cells which are known to be induced in the priming process include, but are not limited to, the promoters of the p35, p40, tumour necrosis factor α (TNF-α), interferon-α (IFN-α) and interferon-β (IFN-β) genes.

The sequences of these promoters are depicted in SEQ ID No. 25 (p35), SEQ ID No. 26 (p40), SEQ ID No. 27 (TNF-α), SEQ ID No. 28 (IFN-α) and SEQ ID No. 29 (IFN-β).

In one embodiment, the promoter used in the expression cassette may be operably linked to a part or all of the coding sequence of the gene to which it is naturally linked, i.e. the nucleic acid sequence the expression of which it controls in a wild-type cell, in addition to the nucleic acid sequence coding for the reporter protein. For example, the promoter of the WRKY29 gene may be linked to the 5' untranslated region (5' UTR) and a part of the first exon of the WRKY29 gene or it may be linked to the 5' UTR, the first exon, the first intron, the second exon, the second intron and part of the third exon of the WRKY29 gene. Such sequences are shown in SEQ ID Nos. 4 and 5. The promoter of the WRKY6 gene may be linked to the first to third exon of the WRKY6 gene. The sequence of the first to third exon of the WRKY6 gene is shown in SEQ ID No. 50. The nucleic acid sequence coding for the reporter protein is located downstream of the part or all of the coding sequence of the gene to which the promoter is naturally linked. Additionally or alternatively, the promoter used in the expression cassette may be operably linked to the 5' UTR of a gene to which it is not naturally linked, such as the 5' UTR of chalcone synthase to provide a suitable ribosome binding site.

In an alternative embodiment, the promoter is not linked to a part or all of the coding sequence of the gene to which it is naturally linked, i.e. the nucleic acid sequence the expression of which it controls in a wild-type cell. Nevertheless, it may be operably linked to the 5' UTR of a gene to which it is not naturally linked, such as the 5' UTR of chalcone synthase to provide a suitable ribosome binding site.

A "functional fragment" of a promoter refers to a smaller part of the promoter with a contiguous nucleotide sequence found in the full-length promoter. The fragment is functional, if it is able to bind the transcription complex and cause expression of the reporter gene to which it is linked and if it its methylation increases upon priming for a stress response.

A "functional derivative" of a promoter refers to a sequence which differs from the wild-type promoter, for example the promoter shown in any of SEQ ID Nos. 3 and 6 to 29, in one or more nucleotides, but to which the transcription complex can still bind and cause expression of the reporter gene and the methylation of which increases upon priming for a stress response. In particular, the term "functional derivative" is intended to include promoters from species other than *Arabidopsis thaliana* which promoters are homologous to the promoters shown in any of SEQ ID Nos. 3 and 6 to 24, i.e. they direct the expression of homologous genes. For example, a promoter homologous to the WRKY6 promoter directs the expression of the WRKY6 gene in another species.

The term "priming" refers to the induction of a physiological state that enables the primed cells to respond to very low levels of a stimulus, preferably an abiotic or biotic stress, in a faster and/or stronger manner than non-primed cells. Thus, primed plants show faster and/or stronger activation of stress responses when challenged by biotic or abiotic stress after priming.

Stress responses are the reaction of a cell or organism to biotic or abiotic stress and include, but are not limited to, enhanced transcription of defence genes such as PAL1, PAL2, 4CL, C4H, WRKY29, WRKY6 and WRKY53.

With respect to nucleic acid sequences or DNA sections in expression cassettes or vectors the terms "operatively linked" and "operably linked" mean that nucleic acid sequences are linked to each other such that the function of one nucleic acid sequence is influenced by the other nucleic acid sequence. For example, if a nucleic acid sequence is operably linked to a promoter, its expression is influenced by said promoter.

Reporter proteins which are encoded by reporter genes are proteins the expression of which can be easily detected and which are attached to a regulatory sequence of another gene to investigate the expression pattern of this regulatory sequence. Hence, the regulatory sequence, in particular the promoter, and the reporter gene are not operably linked in wild-type cells. In a preferred embodiment the expression of the reporter protein is not detected by measuring the expression level of the reporter protein by detecting the amount of mRNA or protein expressed, but by measuring an activity of the reporter protein.

Suitable reporter proteins include, for example the β-glucuronidase (GUS)-encoding uidA gene from *E. coli*, fluorescent proteins, luciferase proteins such as firefly luciferase from *Photinus pyralis*, renilla luciferase from *Renilla reniformis* or the NanoLuc™ luciferase, alkaline phosphatase and the β-galactosidase (lacZ) gene from *E. coli*. If expressed, the GUS, luciferase and β-galactosidase proteins catalyse a reaction which leads to a detectable product, whereas the expression of the fluorescent proteins can be directly determined by detecting the fluorescence.

Further reporter proteins are proteins which confer resistance to certain substances such as the proteins chloramphenicol transferase or neomycin phosphotransferase which confer resistance to chloramphenicol and kanamycin, respectively.

Particularly preferred in the method of the present invention are fluorescent proteins such as AcGFP1, AmCyan1, AsRed2, mBanana, mCherry, Dendra2, DsRed2, E2-Crimson, GFP, HcRed1, mOrange, PAm cherry, mPlum, mRaspberry, mStrawberry, tandem-d-Tomato, Timer, Zsgreen1, Zsyellow1, mNeonGreen, mVenus and superfolder GFP and most preferred is mNeonGreen. The nucleic acid sequences coding for mOrange, tandem-d-tomato, superfolder GFP, mVenus and mNeonGreen are depicted in SEQ ID Nos. 30-34.

The skilled person is aware of methods for determining the expression of the reporter protein. In case of fluorescent proteins, the fluorescent protein is excited with a suitable wavelength and the emitted fluorescent is detected at a suitable wavelength. Suitable wavelengths for exciting and detecting fluorescence of fluorescent proteins are known to the person skilled in the art. For example, for detecting expression of the mNeonGreen protein the cells or organisms are irradiated with light of a wavelength of 480 nm and fluorescence is detected at a wavelength of 530 nm.

The vectors which are used in the method of the present invention may further comprise regulatory elements in addition to the nucleic acid sequence to be transferred. Which specific regulatory elements must be included in said vectors depends on the procedure which is to be used for said vectors. Those skilled in the art, who are familiar with the various methods for producing transgenic cells and organisms know which regulatory elements and also other elements said vectors must include.

Typically, the regulatory elements which are contained in the vectors ensure the transcription and, if desired, the translation in the plant cell.

The term "transcription regulatory element" as used herein refers to a polynucleotide that is capable of regulating the transcription of an operably linked polynucleotide. It includes, but is not limited to, promoters, enhancers, introns, 5' UTRs, and 3' UTRs.

For enhancing the fluorescence of the fluorescent protein, the fluorescent protein may be fused to a localization sequence which targets the protein to the endoplasmic reticulum and/or a retention sequence which retains the fluorescent protein in the endoplasmic reticulum of the cell. Suitable sequences for targeting and retaining proteins to the endoplasmic reticulum are known to the person skilled in the art and shown in SEQ ID Nos. 35 to 37.

So-called termination sequences are sequences which ensure that the transcription or the translation is terminated properly. If the introduced nucleic acids are to be translated, said nucleic acids are typically stop codons and corresponding regulatory sequences; if the introduced nucleic acids are only to be transcribed, said nucleic acids are normally poly-A sequences.

The transgenic eukaryotic cell may be a plant or an animal cell, such as a mammalian cell. Preferably it is a plant cell. The plant cell may be derived from a monocotyledonous or dicotyledonous plant and the plant organism may also be a dicotyledonous or monocotyledonous organism.

Examples of monocotyledonous plants are plants belonging to the genera *Avena* (oat), *Triticum* (wheat), *Secale* (rye), *Hordeum* (barley), *Oryza* (rice), *Panicum*, *Pennisetum*, *Setaria*, Sorghum (millet), *Zea* (maize), and the like.

Dicotyledonous useful plants comprise, inter alia, *Arabidopsis*, cotton, legumes, like leguminous plants and in particular alfalfa, soybean, rape, canola, tomato, sugar beet, potato, ornamental plants, and trees. Further useful plants can comprise fruit (in particular apples, pears, cherries, grapes, citrus, pineapple, and bananas), pumpkin, cucumber, wine, oil palms, tea shrubs, cacao trees, and coffee shrubs, tobacco, sisal, as well as, with medicinal plants, *rauwolfia* and *digitalis*.

Particularly preferred are plants or plant cells which are easy to manipulate and to cultivate such as *Arabidopsis thaliana* plants or plant cells or *Nicotiana tabacum* plants or plant cells. Most preferably, the plant cells are from *Arabidopsis thaliana* or the plant is *Arabidopsis thaliana*.

Suitable mammalian cells include, but are not limited to, human, mouse, rat, hamster, bovine and porcine cells. Preferably the cells are rodent or human cells. Examples of suitable mammalian cells include HeLa, NIH3T3, CHO and 293 cells.

The expression cassette can be introduced into the cells by any method known in the art.

For introducing DNA into a plant cell, a number of well-known techniques are available and those skilled in the art may easily determine the suitable technique for each case. Said techniques comprise the transformation of plant cells with T-DNA using *Agrobacterium tumefaciens* or *Agrobacterium rhizogenes* as transformation means, viral infection by using viral vectors (EP 0 067 553; U.S. Pat. No. 4,407,956, WO 95/34668; WO 93/03161), the fusion of protoplasts, polyethylene glycol-induced DNA uptake, liposome-mediated transformation (U.S. Pat. No. 4,536,475), incubation of dry embryos in DNA-comprising solution, microinjection, the direct gene transfer of isolated DNA in protoplasts, the electroporation of DNA, the introduction of DNA by the biolistic procedure, as well as other possibilities. Thereby, stable as well as transient transformants may be produced.

Methods for introducing the expression cassette into mammalian cells include, but are not limited to, liposome mediated transfection, dendrimer based transfection, electroporation, microinjection, virus-mediated gene delivery, calcium phosphate precipitation, DEAE-dextran-mediated transfection and lipofection. Commercially available kits for transfection, such as SuperFect, PolyFect, Effectene (Qiagen), TransFast™, ProFection®, Transfectam® (Promega) and TransPass™ (NEB) may also be used. Preferably, the cells are transfected while in suspension and under serum-free conditions.

The transgenic cells of the present invention are usually stably transfected, which means that the transgene is stably integrated into the genome of the cell and that successfully transformed cells are selected after transfection by means of a selection agent which kills the non-transfected cells, whereas the transfected cells containing the resistance gene continue growing. For this purpose, the vector used for the transfection which comprises the expression cassette usually also comprises a nucleic acid sequence encoding a selection marker, such as a protein conferring resistance to an agent which is toxic for a wild-type cell.

The transgenic eukaryotic cell or non-human organism may be used in a method for identifying substances which prime eukaryotic cells for a stress response. Substances which prime eukaryotic cells, in particular plant cells, for a stress response prepare the immune system of the cells for future stress. In plants which have been primed for a stress response, the stress response occurs earlier and is stronger, leading to a more effective resistance.

Substances which are known to prime plant cells for a stress response and which also increase the methylation of histones on promoters of genes involved in the stress response include benzo(1,2,3)thiadiazole-7-carbothioic acid S-methyl ester (BTH), salicylic acid (SA) or acetyl salicylic acid (aspirin).

The method of the present invention involves the treatment of the transgenic cells or the transgenic organism, preferably transgenic plant cells or a transgenic plant, with one or more candidate substances, alone or in combination, wherein the cells or organism is contacted with the substance for a certain time period, such as 6 hours and 5 days, preferably 10 hours to 4 days, more preferably 12 hours to 3 days and most preferably 48 to 72 hours. The person skilled in the art will appreciate that the actual incubation time may be different for different reporter genes.

Candidate substances are substances which should be tested for their ability to prime cells for a stress response and include natural and synthetic substances. The term "candidate substances" is also intended to include bacteria and other microorganisms which may secrete substances which prime cells for a stress response. It has been shown that the colonization of *Arabidopsis* roots with *Pseudomonas fluorescens* bacteria primes the plant for a response to pathogens (Hase et al. (2003) Physiological and Molecular Plant Pathology 62: 219-226).

After incubation of the substance with a cell or organism the expression of the reporter protein is determined by a method suitable for determining expression of this reporter protein. For example, if the reporter protein is a fluorescent protein, the expression is detected by exciting the fluorescent protein with light of a suitable wavelength and measuring the emitted light at a suitable wavelength. Suitable incubation times for a particular reporter protein are known or can be easily determined.

As a positive control, the cell or organism may also be treated with one or more substances, from which it is known that they prime cells for a stress response, such as benzo(1,2,3)thiadiazole-7-carbothioic acid S-methyl ester (BTH), salicylic acid (SA) or acetyl salicylic acid (aspirin).

Further, the expression of the reporter protein is usually compared with the expression of this protein in cells or organisms which act as a negative control. Suitable negative control cells or organisms include, but are not limited to:
  (i) cells or organisms of the present invention which have not been treated with the one or more candidate substances and
  (ii) cells or organisms which carry the expression cassette comprising the promoter and the nucleic acid sequence encoding a reporter protein, but which do not comprise the one or more genetic modifications providing the activation of one or more signal transduction pathways which are involved in stress-induced gene expression and/or the pre-activation of one or more members of the transcriptional machinery and which have been treated with the one or more candidate substances.

The negative control cells or organisms are from the same organisms or are the same organisms as the cells of the present invention which are incubated with candidate substances.

Those substances which lead to a significantly increased expression of the reporter protein in the treated cells of the present invention in comparison to the negative control cells are substances which prime the cells for a stress response.

Instead of using the whole organism such as a whole plant or a cell from this organism in the method of the present invention, also parts of the organism can be used in the method of the present invention, such as stems, roots, ovules, stamens, leaves, embryos, meristematic regions, callus tissue, cell suspensions, seedlings, gametophytes, sporophytes, pollen, microspores, seeds and the like.

After identifying substances which are capable of priming a stress response by the method of the present invention, it can be confirmed that these substances prime the cells for a stress response by treatment of wild-type plants with this substance and then contacting the plants with pathogen or abiotic stress and measuring the stress response. It is confirmed that a substance primes cells for a stress response, if after treatment with the substance and contacting the plants with pathogen or abiotic stress the stress response in the plant treated with the substance occurs earlier and/or is stronger than in a plant not treated with the substance.

The production of a transgenic plant cell of the present invention as well as its use in a method of identifying substances which prime for a stress response is described in the following examples:

EXAMPLES

1. Preparation of a Reporter Gene Construct

The expression cassette comprising the promoter the methylation of which increases after priming for a stress response operably linked to a reporter protein was cloned into the pGreenII-0229 plasmid which carries a kanamycin and a phosphinothricin resistance gene (SEQ ID No. 65). The plasmid was cut with C/al to remove the lacZ expression cassette and then self-ligated.

The WRKY6 promoter was amplified via PCR with the DNA primers according to SEQ ID Nos. 51 and 52 from *Arabidopsis thaliana* genomic DNA and ligated in the pGreenII-0229 plasmid which had been cut with EcoRV and EcoRI.

The 5' UTR from CHS was amplified from *Petroselinum crispum* genomic DNA using the primers according to SEQ ID Nos. 53 and 54 and ligated 3' of the WRKY6 promoter via the EcoRI and SmaI restriction sites.

The WAK1 ER localisation sequence was amplified from *Arabidopsis thaliana* genomic DNA using the primers according to SEQ ID Nos. 55 and 56 and ligated 3' of the 5' UTR from CHS via the SmaI and NotI restriction sites.

The WRKY coding sequence from the first to the third exon was amplified from *Arabidopsis thaliana* genomic DNA using the primers according to SEQ ID Nos. 57 and 58 and ligated 3' of the WAK1 ER localisation sequence via the NotI and AleI restriction sites.

The nucleic acid sequence coding for the reporter protein monomeric NeonGreen was amplified from a plasmid obtained from Allele Biotechnology, 6404 Nancy Ridge Drive San Diego, Calif. 92121 (allelebiotech.com) using the primers according to SEQ ID Nos. 59 and 60. In this PCR reaction the nucleic acid sequence coding for the ER retention signal was fused to the nucleic acid sequence coding for monomeric NeonGreen. The resulting nucleic acid molecule was ligated 3' of the WRKY6 coding sequence via the AleI and SapI restriction sites.

Finally, the terminator sequence from octopin synthase was amplified from plasmid pEarleyGate 100 (ABRC stock number CD3-724) using the primers according to SEQ ID Nos. 61 and 62 and ligated 3' of the nucleic acid sequence coding for monomeric NeonGreen via the SapI restriction site.

The plasmid was transformed into *E. coli* cells by heat shock and positive colonies were selected with kanamycin.

2. Transformation of the Reporter Gene Construct

The plasmid carrying the complete expression cassette of example 1 was transformed into *Agrobacterium tumefaciens* strain GV3101 using heat shock. Agrobacteria containing the plasmid were selected and used to transform *Arabidopsis thaliana* plants in which the activity of CPL1 was abrogated by a T-DNA insertion. These plants were obtained from The European *Arabidopsis* Stock Centre (arabidopsis.info; Nottingham *Arabidopsis* Stock Centre, School of Biosciences, University of Nottingham, Sutton Bonington Campus, Loughborough, LE12 5RD United Kingdom) under catalogue number N6541. For the transformation the floral dip method (Clough and Bent (1998) Plant J. 16: 735-743) was used. Seeds were obtained from the transformed plants and transferred to soil containing phosphinotricin to select for plants carrying the transformed plasmid. From positive seeds complete plants were recovered.

3. Identification of Substances which Induce Priming

Plant seeds obtained from the plants prepared in Example 2 were transferred into soil and plants were grown for five weeks at a light intensity of 80 to 180 µmol/m$^2$/s. A solution or suspension of the substances to be tested was sprayed on the plants. Three days after the spraying the plants were irradiated with light with a wavelength of 480 nm and the emitted light was detected at a wavelength of 530 nm to determine the expression of the reporter protein. The intensity of the emitted light indicated whether the substance has induced the priming or not. If the intensity of the light emitted by the treated plants was stronger than the intensity of the light emitted by treated plants which carry only the reporter gene construct, but not the CPL1 mutation, the substance had an influence on the promoter of the reporter gene construct and on the priming of the cells.

Some embodiments of the present invention include:
1. Transgenic eukaryotic cell or non-human organism comprising:
a) one or more genetic modifications providing the activation of one or more signal transduction pathways which are involved in stress-induced gene expression and/or the pre-activation of one or more members of the transcriptional machinery; and
b) an expression cassette which comprises:
 (i) a promoter the methylation of which increases upon priming for a stress response or a functional fragment or functional derivative of such a promoter;
 (ii) operatively linked thereto a nucleic acid sequence coding for a reporter protein; and
 (iii) optionally, further regulatory elements.
2. Transgenic eukaryotic cell or non-human organism of 1, wherein the one or more genetic modifications providing the activation of one or more signal transduction pathways which are involved in stress-induced gene expression and/or the pre-activation of one or more members of the transcriptional machinery lead to an altered expression or activity of a protein selected from the group consisting of RNA polymerase II, EDR1, MKP1, MKP2, MPK4, EDS1, PAD4, WRKY70, WRKY18, MYB44, SPT4, SPT5 and SNI1.
3. Transgenic eukaryotic cell or non-human organism of 1 or 2, wherein the one or more genetic modifications lead to an increased expression or activity of a protein selected from the group consisting of RNA polymerase II, EDS1, PAD4, WRKY70, WRKY18 and MYB44.
4. Transgenic eukaryotic cell or non-human organism of 1 or 2, wherein the one or more genetic modifications lead to a decreased expression or activity of a protein selected from the group consisting of EDR1, MKP1, MKP2, MPK4, SPT4, SPT5 and SNI1.
5. Transgenic eukaryotic cell or non-human organism of 1 or 2, wherein the genetic modification providing the activation of one or more signal transduction pathways which are involved in stress-induced gene expression and/or the pre-activation of one or more members of the transcriptional machinery leads to an altered expression or activity of RNA polymerase II.
6. Transgenic eukaryotic cell or non-human organism of 5, wherein the RNA polymerase II is constitutively phosphorylated.
7. Transgenic eukaryotic cell or non-human organism of 6, wherein the RNA polymerase II is constitutively phosphorylated by reducing the activity of a phosphatase capable of dephosphorylating RNA polymerase II.
8. Transgenic eukaryotic cell or non-human organism of any of 1 to 7, wherein the methylation is the attachment of one, two or three methyl residues to lysine 4 of histone H3.
9. Transgenic eukaryotic cell or non-human organism of any of 1 to 7, wherein the methylation is the attachment of three methyl residues to lysine 4 of histone H3.
10. Transgenic eukaryotic cell or non-human organism of any of 9 to 7, wherein the promoter is the promoter of a gene selected from the group consisting of: WRKY6, WRKY29, WRKY70, WRKY53, PR1, PAL1, PAL2, 4CL, C4H, RD29B, RAB18, P5CS1, LPT3, LPT4, HSFA6A, HIPP22, WRKY38, WRKY31, PR5, ICS1, HEL, PDF1-2, p35, p40, tumour necrosis factor α, interferon-α and interferon-β or a functional fragment or functional derivative of any of these promoters.
11. Transgenic eukaryotic cell or non-human organism of any of 1 to 10, wherein the promoter has a sequence selected from the group consisting of SEQ ID Nos. 3, 6 to 29, 63 and 64 or is a functional fragment or functional derivative of any of these promoters.
12. Transgenic eukaryotic cell or non-human organism of any of 1 to 10, wherein the promoter is the promoter of a gene selected from the group consisting of: WRKY29, WRKY6, WRKY70, WRKY53, PR1, PAL1, PAL2, 4CL, C4H, RD29B, RAB18, P5CS1, LPT3, LPT4, HSFA6A and HIPP22.
13. Transgenic eukaryotic cell or non-human organism of 12, wherein the promoter has a sequence selected from the group consisting of SEQ ID Nos. 3 and 6 to 20 or is a functional fragment or functional derivative of any of these promoters.
14. Transgenic eukaryotic cell or non-human organism of any of 1 to 10, wherein the promoter is the promoter of a gene selected from the group consisting of: WRKY29, WRKY6, WRKY70, WRKY53, PR1, RD29B, RAB18, P5CS1, LPT3, LPT4, HSFA6A and HIPP22.
15. Transgenic eukaryotic cell or non-human organism of 14, wherein the promoter has a sequence selected from the group consisting of SEQ ID Nos. 3, 6 to 9 and 14 to 20 or is a functional fragment or functional derivative of any of these promoters.

16. Transgenic eukaryotic cell or non-human organism of any of 1 to 15, wherein the reporter protein is selected from the group consisting of: fluorescent proteins, luciferase proteins, β-galactosidase, alkaline phosphatase, β-glucuronidase and chloramphenicol acetyltransferase.

17. Transgenic eukaryotic cell or non-human organism of 16, wherein the fluorescent protein is selected from the group consisting of AcGFP1, AmCyan1, AsRed2, mBanana, mCherry, Dendra2, DsRed2, E2-Crimson, GFP, HcRed1, mOrange, PAm cherry, mPlum, mRaspberry, mStrawberry, tandem-d-Tomato, Timer, Zsgreen1, Zsyellow1, mNeonGreen, mVenus and superfolder GFP.

18. Transgenic eukaryotic cell or non-human organism of 17, wherein the fluorescent protein is mNeonGreen.

19. Transgenic eukaryotic cell or non-human organism of 18, wherein the fluorescent protein is encoded by the nucleic acid sequence according to SEQ ID No. 34.

20. Transgenic eukaryotic cell or non-human organism of any of 1 to 19, being a plant cell or plant organism.

21. Transgenic eukaryotic cell or non-human organism of 20, wherein the plant cell is from an *Arabidopsis thaliana* plant or the plant organism is an *Arabidopsis thaliana* plant.

22. Transgenic eukaryotic cell or non-human organism of 20 or 21, wherein the promoter is the promoter of a gene selected from the group consisting of: WRKY6, WRKY29, WRKY70, WRKY53, PR1, PAL1, PAL2, 4CL, C4H, RD29B, RAB18, P5CS1, LPT3, LPT4, HSFA6A, HIPP22, WRKY38, WRKY31, PR5, ICS1, HEL, PDF1-2 or a functional fragment or functional derivative of any of these promoters.

23. Transgenic eukaryotic cell or non-human organism of 20 to 22, wherein the promoter has a sequence selected from the group consisting of SEQ ID Nos. 3, 6 to 24, 63 and 64 or is a functional fragment or functional derivative of any of these promoters.

24. Transgenic eukaryotic cell or non-human organism of 20 to 22, wherein the promoter is the promoter of a gene selected from the group consisting of: WRKY29, WRKY6, WRKY70, WRKY53, PR1, PAL1, PAL2, 4CL, C4H, RD29B, RAB18, P5CS1, LPT3, LPT4, HSFA6A and HIPP22.

25. Transgenic eukaryotic cell or non-human organism of 23, wherein the promoter has a sequence selected from the group consisting of SEQ ID Nos. 3 and 6 to 20 or is a functional fragment or functional derivative of any of these promoters.

26. Transgenic eukaryotic cell or non-human organism of 20 to 22, wherein the promoter is the promoter of a gene selected from the group consisting of: WRKY29, WRKY6, WRKY70, WRKY53, PR1, RD29B, RAB18, P5CS1, LPT3, LPT4, HSFA6A and HIPP22.

27. Transgenic eukaryotic cell or non-human organism of 26, wherein the promoter has a sequence selected from the group consisting of SEQ ID Nos. 3, 6 to 9 and 14 to 20 or is a functional fragment or functional derivative of any of these promoters.

28. Transgenic eukaryotic cell or non-human organism of any of 1 to 19, being an animal cell or a non-human animal organism.

29. Transgenic eukaryotic cell or non-human organism of 28, being a mammalian cell.

30. Transgenic eukaryotic cell or non-human organism of 28 or 29, wherein the promoter is the promoter of a gene selected from the group consisting of: p35, p40, tumour necrosis factor α, interferon-α and interferon-β or a functional fragment or functional derivative of any of these promoters.

31. Transgenic eukaryotic cell or non-human organism of 28 to 30, wherein the promoter has a sequence selected from the group consisting of SEQ ID Nos. 25 to 29 or is a functional fragment or functional derivative of any of these promoters.

32. Transgenic plant cell or plant organism comprising:
(a) one or more genetic modifications leading to an altered expression or activity of one or more proteins selected from the group consisting of RNA polymerase II, EDR1, MKP1, MKP2, MPK4, EDS1, PAD4, WRKY70, WRKY18, MYB44, SPT4, SPT5 and SNI1; and
(b) an expression cassette which comprises the following elements in 5' to 3' direction:
  (i) a promoter of a gene selected from the group consisting of: WRKY6, WRKY29, WRKY70, WRKY53, PR1, PAL1, PAL2, 4CL, C4H, RD29B, RAB18, P5CS1, LPT3, LPT4, HSFA6A, HIPP22, WRKY38, WRKY31, PR5, ICS1, HEL, PDF1-2 or a functional fragment or functional derivative of any of these promoters;
  (ii) operatively linked thereto a nucleic acid sequence coding for a reporter protein; and
  (iii) optionally, a transcription termination sequence.

33. Transgenic plant cell or plant organism of 32, wherein the one or more genetic modifications lead to an increased expression or activity of a protein selected from the group consisting of RNA polymerase II, EDS1, PAD4, WRKY70, WRKY18 and MYB44.

34. Transgenic plant cell or plant organism of 32, wherein the one or more genetic modifications lead to a decreased expression or activity of a protein selected from the group consisting of EDR1, MKP1, MKP2, MPK4, SPT4, SPT5 and SNI1.

35. Transgenic plant cell or plant organism comprising:
(a) a genetic modification resulting in the constitutive phosphorylation of RNA polymerase II; and
(b) an expression cassette which comprises the following elements in 5' to 3' direction:
  (i) a promoter of a gene selected from the group consisting of: WRKY6, WRKY29, WRKY70, WRKY53, PR1, PAL1, PAL2, 4CL, C4H, RD29B, RAB18, P5CS1, LPT3, LPT4, HSFA6A, HIPP22, WRKY38, WRKY31, PR5, ICS1, HEL, PDF1-2 or a functional fragment or functional derivative of any of these promoters;
  (ii) operatively linked thereto a nucleic acid sequence coding for a reporter protein; and
  (iii) optionally, a transcription termination sequence.

36. Transgenic plant cell or plant organism of 35, wherein the modification results in the reduction of activity of a phosphatase capable of dephosphorylating RNA polymerase II.

37. Transgenic plant cell or plant organism of 36, wherein the phosphatase is CPL1 or CPL3.

38. Transgenic plant cell or plant organism of 37, wherein the nucleic acid sequence encoding CPL1 is the sequence according to SEQ ID No. 1.

39. Transgenic plant cell or plant organism of 37, wherein the nucleic acid sequence encoding CPL3 is the sequence according to SEQ ID No. 2.

40. Transgenic plant cell or plant organism of any of 35 to 39, wherein the activity of the phosphatase is reduced by a T-DNA insertion which leads to a reduction of phosphatase expression, by chemical mutagenesis, by RNA interference, by miRNA, by an aptamer, by an antibody specifically binding to the phosphatase, by an antisense sequence, by TILLING, by TALENS or by post-transcriptional gene silencing.

41. Transgenic plant cell or plant organism of 40, wherein the activity of the phosphatase is reduced by a T-DNA insertion which leads to a reduction of phosphatase expression.

42. Transgenic plant cell or plant organism of 41, wherein the T-DNA insertion is the one present in the plants obtainable from The European *Arabidopsis* Stock Centre under a catalogue number selected from the group consisting of N6541, N415837, N481418, N861773, N865879 and N6542.

43. Transgenic plant cell or plant organism of any of 32 to 42, wherein the promoter is the promoter of a gene selected from the group consisting of: WRKY29, WRKY6, WRKY70, WRKY53, PR1, PAL1, PAL2, 4CL, C4H, RD29B, RAB18, P5CS1, LPT3, LPT4, HSFA6A and HIPP22.

44. Transgenic plant cell or plant organism of 43, wherein the promoter has a sequence selected from the group consisting of SEQ ID Nos. 3 and 6 to 20 or is a functional fragment or functional derivative of any of these promoters.

45. Transgenic plant cell or plant organism of any of 32 to 42, wherein the promoter is the promoter of a gene selected from the group consisting of: WRKY29, WRKY6, WRKY70, WRKY53, PR1, RD29B, RAB18, P5CS1, LPT3, LPT4, HSFA6A and HIPP22.

46. Transgenic plant cell or plant organism of 45, wherein the promoter has a sequence selected from the group consisting of SEQ ID Nos. 3, 6 to 9 and 14 to 20 or is a functional fragment or functional derivative of any of these promoters.

47. Transgenic plant cell or plant organism of any of 32 to 46, wherein the promoter is the promoter of the WRKY6 gene.

48. Transgenic plant cell or plant organism of 47, wherein the promoter of the WRKY6 gene has the sequence according to SEQ ID No. 6 or is a functional derivative or functional fragment thereof.

49. Transgenic plant cell or plant organism of any of 32 to 48, wherein the reporter protein is selected from the group consisting of: fluorescent proteins, luciferase protein, β-galactosidase, alkaline phosphatase, β-glucuronidase and chloramphenicol acetyltransferase.

50. Transgenic plant cell or plant organism of 49, wherein the fluorescent protein is selected from the group consisting of: AcGFP1, AmCyan1, AsRed2, mBanana, mCherry, Dendra2, DsRed2, E2-Crimson, GFP, HcRed1, mOrange, PAm cherry, mPlum, mRaspberry, mStrawberry, tandem-d-Tomato, Timer, Zsgreen1, Zsyellow1, mNeonGreen, mVenus and superfolder GFP.

51. Transgenic plant cell or plant organism of 50, wherein the fluorescent protein is mNeonGreen.

52. Transgenic plant cell or plant organism of 51, wherein the fluorescent protein is encoded by the nucleic acid sequence according to SEQ ID No. 34.

53. Transgenic plant cell or plant organism of any of 32 to 52, wherein the cell is from an *Arabidopsis thaliana* plant or the plant is an *Arabidopsis thaliana* plant.

54. Transgenic plant cell or plant organism comprising:
(a) a T-DNA insertion which leads to a reduction of the expression of a phosphatase capable of dephosphorylating RNA polymerase II;
(b) an expression cassette which comprises the following elements in 5' to 3' direction:
  (i) a promoter of the WRKY6 gene or a functional fragment or functional derivative of this promoter;
  (ii) operatively linked thereto a nucleic acid sequence coding for a reporter protein; and
  (iii) optionally, a transcription termination sequence.

55. Transgenic plant cell or plant organism of 54, wherein the T-DNA insertion is the one present in the plants obtainable from The European *Arabidopsis* Stock Centre under a catalogue number selected from the group consisting of N6541, N415837, N481418, N861773, N865879 and N6542.

56. Transgenic plant cell or plant organism of 54 or 55, wherein the promoter of the WRKY6 gene has the sequence according to SEQ ID No. 6 or is a functional derivative or functional fragment thereof.

57. Transgenic plant cell or plant organism of any of 54 to 56, wherein the reporter protein is selected from the group consisting of: proteins, luciferase protein, β-galactosidase, alkaline phosphatase, β-glucuronidase and chloramphenicol acetyltransferase.

58. Transgenic plant cell or plant organism of 57, wherein the fluorescent protein is selected from the group consisting of: AcGFP1, AmCyan1, AsRed2, mBanana, mCherry, Dendra2, DsRed2, E2-Crimson, GFP, HcRed1, mOrange, PAm cherry, mPlum, mRaspberry, mStrawberry, tandem-d-Tomato, Timer, Zsgreen1, Zsyellow1, mNeonGreen, mVenus and superfolder GFP.

59. Transgenic plant cell or plant organism of 58, wherein the fluorescent protein is mNeonGreen.

60. Transgenic plant cell or plant organism of 59, wherein the fluorescent protein is encoded by the nucleic acid sequence according to SEQ ID No. 34.

61. Transgenic plant cell or plant organism of any of 54 to 60, wherein the cell is from an *Arabidopsis thaliana* plant or the plant is an *Arabidopsis thaliana* plant.

62. Method for identifying substances which prime eukaryotic cells for a stress response, comprising the steps of:
(a) treating the transgenic eukaryotic cell or non-human of any of 1 to 31 or the transgenic plant cell or plant organism of any of 32 to 61 with one or more candidate substances; and
(b) determining expression of the reporter protein.

63. Method of 62, wherein the transgenic plant cell or plant organism of any of 32 to 61 is treated with the one or more candidate substances.

62. Method of 62 or 63, wherein the transgenic eukaryotic cell or non-human organism or the transgenic plant cell or plant organism is treated with the one or more candidate substances for a period of 6 hours to 5 days.

63. Method of 62 to 64, wherein increased expression of the reporter protein compared to the expression in the negative control indicates that the candidate substance primes the cells for the stress response.

64. Method of 65, wherein the negative control is selected from the group consisting of:
(i) cells of any of claims 1 to 61 which have not been treated with the one or more candidate substances; and (ii) cells which carry the expression cassette of (b) of claims 1 to 61, but which do not comprise the one or more genetic modifications of (a) of claims 1 to 59 and which have been treated with the one or more candidate substances.

65. Use of the transgenic eukaryotic cell or non-human organism of any of 1 to 31 or the transgenic plant cell or plant organism of any of 32 to 61 for the identification of substances which prime cells for a stress response.

The invention claimed is:

1. A method for identifying substances which prime *Arabidopsis thaliana* cells for a stress response comprising;
   (a) providing a transgenic *Arabidopsis thaliana* plant cell or a transgenic *Arabidopsis thaliana* plant organism comprising:
      (i) a T-DNA insertion into the coding sequence of an endogenous plant genomic DNA gene encoding an endogenous *Arabidopsis thaliana* C-terminal domain phosphatase-like (CPL) protein capable of dephosphorylating an endogenous RNA polymerase II, wherein the T-DNA insertion results in complete loss of activity of said endogenous *Arabidopsis thaliana* CPL protein, thereby causing a loss of dephosphorylation of the endogenous RNA polymerase II by said endogenous *Arabidopsis thaliana* CPL protein, wherein the complete loss of activity of said endogenous *Arabidopsis thaliana* CPL protein results in a constitutively phosphorylated said endogenous RNA polymerase II; and
      (ii) an expression cassette which comprises; a WRKY6 promoter, wherein said WRKY6 promoter has the nucleotide sequence as set forth in SEQ ID NO: 6 or comprises a nucleotide sequence obtained from plant species other than *Arabidopsis thaliana*, and having stress responsive promoter activity of the SEQ ID NO; 6 by directing the expression of a WRKY6 coding sequence in a stress responsive manner, wherein said WRKY6 promoter is able to bind a transcription complex and cause expression of a coding sequence to which it is operatively linked, wherein said WRKY6 promoter is operatively linked to a nucleic acid sequence coding for a reporter protein, wherein the WRKY6 promoter and the nucleic acid sequence coding for the reporter protein are heterologous to each other; and wherein priming of a stress response by treatment of said transgenic *Arabidopsis thaliana* plant cell or said transgenic *Arabidopsis thaliana* plant organism with benzo-(1,2,3)-thiadiazole-7-carbothioic acid S-methyl ester (BTH) increases methylation at lysine 4 of histone 3 proteins within chromatin associated with said WRKY6 promoter and thereby increases transcription of the operatively linked coding sequence for the reporter protein;
   (b) treating said transgenic *Arabidopsis thaliana* plant cell or said transgenic *Arabidopsis thaliana* plant organism with one or more candidate substances; and
   (c) determining expression of the reporter protein, and wherein increase in expression of the reporter protein as compared to the expression in a negative control identifies said one or more candidate substances which prime *Arabidopsis thaliana* cells for the stress response.

2. The method of claim 1, wherein said transgenic *Arabidopsis thaliana* plant cell or said transgenic *Arabidopsis thaliana* plant organism is treated with said one or more candidate substances for a period of 6 hours to 5 days.

3. The method of claim 1, wherein the negative control comprises:
   a transgenic *Arabidopsis thaliana* plant cell or a transgenic *Arabidopsis thaliana* plant organism comprising:
      (1) a T-DNA insertion into the coding sequence of an endogenous plant genomic DNA gene encoding an endogenous *Arabidopsis thaliana* C-terminal domain phosphatase-like (CPL) protein capable of dephosphorylating an endogenous RNA polymerase II, wherein the T-DNA insertion results in complete loss of activity of said endogenous *Arabidopsis thaliana* CPL protein, thereby causing a loss of dephosphorylation of the endogenous RNA polymerase II by said endogenous *Arabidopsis thaliana* CPL protein, wherein the complete loss of activity of said endogenous *Arabidopsis thaliana* CPL protein results in a constitutively phosphorylated said endogenous RNA polymerase II; and
      (2) an expression cassette which comprises a WRKY6 promoter, wherein said WRKY6 promoter has the nucleotide sequence as set forth in SEQ ID NO: 6 or comprises a nucleotide sequence obtained from a plant species other than *Arabidopsis thaliana*, and having stress responsive promoter activity of the SEQ ID NO: 6 by directing the expression of a WRKY6 coding sequence in a stress responsive manner, wherein said WRKY6 promoter is able to bind a transcription complex and cause expression of a coding sequence to which it is operatively linked, wherein said WRKY6 promoter is operatively linked to a nucleic acid sequence coding for a reporter protein, wherein the WRKY6 promoter and the nucleic acid sequence coding for the reporter protein are heterologous to each other; and wherein priming of a stress response by treatment of said transgenic *Arabidopsis thaliana* plant cell or said transgenic *Arabidopsis thaliana* plant organism with benzo-(1,2,3)-thiadiazole-7-carbothioic acid S-methyl ester (BTH) increases methylation at lysine 4 of histone 3 proteins within chromatin associated with said WRKY6 promoter and thereby increases transcription of the operatively linked coding sequence for the reporter protein, and further wherein said transgenic *Arabidopsis thaliana* plant cell or said transgenic *Arabidopsis thaliana* plant organism of the negative control has not been treated with the one or more candidate substances.

4. The method of claim 3, wherein said expression cassette further comprises a termination sequence operatively linked to said nucleic acid sequence coding for said reporter protein.

5. The method of claim 1, wherein the negative control comprises:

a transgenic *Arabidopsis thaliana* plant cell or a transgenic *Arabidopsis thaliana* plant organism comprising an expression cassette which comprises a WRKY6 promoter, wherein said WRKY6 promoter has the nucleotide sequence as set forth in SEQ ID NO: 6 or comprises a nucleotide sequence obtained from a plant species other than *Arabidopsis thaliana*, and having stress responsive promoter activity of the SEQ ID NO: 6 by directing the expression of a WRKY6 coding sequence in a stress responsive manner, wherein said WRKY6 promoter is able to bind a transcription complex and cause expression of a coding sequence to which it is operatively linked, wherein said WRKY6 promoter is operatively linked to a nucleic acid sequence coding for a reporter protein, wherein the WRKY6 promoter and the nucleic acid sequence coding for the reporter protein are heterologous to each other; and wherein priming of a stress response by treatment of the transgenic *Arabidopsis thaliana* plant cell or transgenic *Arabidopsis thaliana* plant organism with benzo-(1,2,3)-thiadiazole-7-carbothioic acid S-methyl ester (BTH) increases methylation at lysine 4 of histone 3 proteins within chromatin associated with said WRKY6 promoter and thereby increases transcription of the operatively linked coding sequence for the reporter protein, and wherein said transgenic *Arabidopsis thaliana* plant cell or said transgenic *Arabidopsis* of said negative control does not comprise a T-DNA insertion into the coding sequence of an endogenous plant genomic DNA gene encoding an endogenous *Arabidopsis thaliana* C-terminal domain phosphatase-like (CPL) protein capable of dephosphorylating endogenous RNA polymerase II, wherein the T-DNA insertion results in complete loss of activity of said endogenous *Arabidopsis thaliana* CPL protein, thereby causing a loss of dephosphorylation of the endogenous RNA polymerase II by said endogenous *Arabidopsis thaliana* CPL protein, wherein the complete loss of activity of said endogenous *Arabidopsis thaliana* CPL protein results in a constitutively phosphorylated endogenous RNA polymerase and wherein said transgenic *Arabidopsis thaliana* plant cell or said transgenic *Arabidopsis thaliana* of said negative control has been treated with said one or more candidate substances.

6. The method of claim 5, wherein said expression cassette further comprises a termination sequence operatively linked to said nucleic acid sequence coding for said reporter protein.

\* \* \* \* \*

```
                        SEQUENCE LISTING

<160> NUMBER OF SEQ ID NOS: 67

<210> SEQ ID NO 1
<211> LENGTH: 2904
<212> TYPE: DNA
<213> ORGANISM: Arabidopsis thaliana

<400> SEQUENCE: 1
atgtatagta ataatagagt agaagtgttt catggtgatg aagacttgg agaattggag       60 atataccctt caagggaatt gaatcagcaa caagatgatg tgatgaagca gaggaagaag     120
aaacagaggg aagtaatgga gctagccaag atgggaatca gaataagcca cttttctcaa    180
tctggcgaga ggtgtcctcc tcttgcaata cttactacaa tttcatcttg tggcctttgt    240
ttcaaattag aagcttcacc ttctccagct caggagtcac tcagtttatt ctactcgtcc    300
tgtctcaggg acaacaagac agcagtaatg ctcttgggtg gagaagagct ccatttggtt    360
gctatgtact cggaaaatat caagaatgac cgtccttgtt tctgggcatt tagtgttgct    420
cctggaattt acgattcctg tcttgttatg ttgaatctta gatgtctggg tattgtcttt    480
gatcttgatg aaaccttgt agtggcgaat accatgcgct catttgagga taagattgac     540
gggtttcagc ggagaataaa caacgagatg gaccctcaac gccttgccgt tatagtggct    600
gagatgaagc gttatcaaga tgacaaaaat ctattgaagc aatatattga aagtgaccag    660
gttgttgaaa acggggaggt gataaaggtg caatctgaaa ttgttcctgc cttgtctgac    720
aaccatcagc ctcttgttcg ccctctgata aggttgcaag agaagaatat tattctgact    780
cgcattaacc caatgattcg tgatacaagt gttcttgtga aatgaggcc ctcatgggag     840 gaacttcgaa gctatttgac agcaaaaggg cgtaagcgtt ttgaagtata tgtttgcacg    900
atggctgaaa gagattacgc cttagagatg tggaggctcc ttgatccaga agggaatttg    960
ataaacacaa atgacttgct tgctcgcatc gtttgtgtga aatctggttt taaaaagtca   1020
ctgttcaatg tgtttctcga tggaacctgc catccaaaga tggcattggt aattgatgat   1080
cgattgaaag tttgggatga aaggatcag ccgagggtac atgtggttcc tgcattcgct    1140 ccctatatt ctcctcaagc tgaagctgct gcaacaccag tactatgtgt tgccaggaac    1200
gttgcctgtg gtgtcagagg tggatttttc agggatttg atgatagtct gctaccaagg    1260
attgctgaaa tttcttatga aatgatgct gaggatattc cttctccgcc tgatgtcagc     1320
cattatttgg tgtcggagga tgatacatcg ggtttaaatg ggaacaaaga tccactttcc   1380
tttgacggga tggctgatac tgaagtggag agaagactga aggaggcaat ttctgcatct   1440
tcagctgtcc ttccggcggc aaatatagat ccgaggatag ctgctcccgt tcagttcccc   1500
atggcttctg cttcttctgt ttcagttcca gtaccagtac aagtcgtgca acaagcaata   1560
caaccttcag ctatggcctt tccaagtatt ccatttcaac aacctcaaca accgacatca   1620
atagctaaac acttggttcc ttcagaacca agcttgcaga gttctcctgc tagagaggaa   1680
ggtgaggtac ctgaatcaga attagatcca gatactagga ggagactcct catattgcag   1740
catggacaag atactaggga tcctgctcca agtgaacctt catttcctca gagacctcca   1800
gttcaagctc caccctcaca tgtgcaatca agaaatggct ggtttcctgt tgaggaggag   1860
```

-continued

| | |
|---|---|
| atggatcctg ctcaaattcg tcgagcagtc tcaaaagaat atccgttgga ttctgaaatg | 1920 |
| attcatatgg aaaagcacag gcctcgtcat ccatcatttt tttctaagat tgataactca | 1980 |
| actcagtctg acaggatgct tcatgagaat cgcaggccgc caaaggagtc tctccggaga | 2040 |
| gatgaacagt tacgttcaaa taacaatcta cctgactctc atcctttcta tggggaggat | 2100 |
| gcgtcttgga atcaatcttc ctctaggaac agtgatcttg acttcctacc tgaacgaagt | 2160 |
| gtctcagcaa cggagacttc agctgatgtt ctacacggaa ttgctatcaa atgtggagct | 2220 |
| aaggtggagt acaaaccaag tttagtttct agtacagatt gcggttctc tgttgaggct | 2280 |
| tggctttcta atcaaaaaat tggagaaggg attggcaaat cgagaagaga agccctgcat | 2340 |
| aaggctgctg aagcttctat acagaattta gctgatggat atatgcgtgc aaatggtgac | 2400 |
| ccagggccca gccacagaga tgctaccccc ttcaccaatg aaaatataag tatgggaaac | 2460 |
| gcaaatgcgc ttaataatca gccatttgct agagatgaaa cagcgttgcc agtttcttct | 2520 |
| agacctacag atccgagatt agaaggttct atgaggcaca ctggctccat tactgcactc | 2580 |
| agggaattgt gtgcatcgga gggtcttgag atggctttc aatctcagcg tcagcttcca | 2640 |
| tctgacatgg tccacagaga tgaattacat gctcaggttg aaatagatgg gcgtgttgta | 2700 |
| ggggaaggag ttggatcgac atgggacgaa gctagaatgc aggctgctga gagagcactg | 2760 |
| tccagtgtga gatcaatgct tggtcaacct ctgcataaac gacaaggatc tccacgatca | 2820 |
| tttggtggga tgtcaaacaa gcgattaaag ccggacttc aacggtctct gcaacggatg | 2880 |
| ccatcttcgg gaagatactc ttaa | 2904 |

<210> SEQ ID NO 2
<211> LENGTH: 4322
<212> TYPE: DNA
<213> ORGANISM: Arabidopsis thaliana

<400> SEQUENCE: 2

| | |
|---|---|
| atgcttgtag ctcgatctgg ttgttctaga acctaattc gaatgggcaa cgatgaaaac | 60 |
| ttgatggtaa tggtggatgt tgaggaaggt gagattcctg attctgtcaa cactgagatt | 120 |
| gaagttaagc acaagagtac tactactacg gccgatgttg gcggagacgt cgatgttggg | 180 |
| gttgtggctg aggaagagg aggaggtggt ggtggttcta atggcaactc tagggtttgg | 240 |
| acaatggagg agttgatttc tcagtatcct gcttaccgtc catatgcgaa ttcgggttta | 300 |
| tctaatttag cttgggctcg agctgtgcag aacaaaacct ttaatgaagg tttggtaatg | 360 |
| gattatgaac caagagagag tgataagatt gtgattgaag atagtgatga tgagaaagaa | 420 |
| gaaggtgagt tggaggaagg tgaaattgat ttggtcgaca atgcttctga tgacaatttg | 480 |
| gttgagaagg atactgaatc tgttgtgttg ataagtgctg ataaagttga agatgatcga | 540 |
| attctaaagg agagagattt ggagaagaaa gtgaaactaa ttcgtggtgt tttggagagt | 600 |
| acttcgttgg tagaagcaca gaccggattt gaaggagttt gttccagaat attgggggcg | 660 |
| ttagagtctt tgcgagagct ggtttcagat aatgatgatt ttccgaagag ggatacttta | 720 |
| gttcaattgt catttgcttc tcttcaaacc attaactatg tgttttgctc gatgaacaat | 780 |
| atttccaagg agcgtaataa ggagactatg tcaagattgc tgactcttgt aaatgaccat | 840 |
| ttttcccaat ttctctcatt caaccagaaa atgagatag agaccatgaa tcaggattta | 900 |
| agccgttctg ctattgcagt ttttgctgga accagcagtg aagagaatgt taatcaaatg | 960 |
| actcagccga gtaatggtga ttcttttctt gccaaaaagc tgacttcaga agtacacat | 1020 |
| cgaggagccg cctacttaag gagtaggttg cctatgctgc ctcttctaga ccttcataag | 1080 |

```
gatcatgatg cagacagcct tccgtcgccc acaagggaaa caacaccaag tttacctgta    1140
aatggtcgcc atacaatggt tagaccaggt tttcccgttg gtagagagag ccaaacgact    1200
gagggtgcca aagtctattc atatgagagt gatgcccgta aagcagtttc tacctaccag    1260
caaaaatttg gtcttaattc agtgtttaag acagatgacc ttccaagccc aaccccatca    1320
ggagaaccta atgatggcaa tggagacgtt ggtggagagg tttccagttc tgttgttaag    1380
agctcgaacc cggggagtca cctaatttat gggcaagacg ttcctctgcc ctccaatttt    1440
aattctagaa gcatgcctgt tgcaaattct gtttctagca ctgttccacc acatcatctg    1500
tcaattcatg ctatttctgc accaactgcc tctgatcaga cagtgaaacc ttctgcaaag    1560
agtcgagatc caagactaag gcttgcgaaa cctgatgctg ccaatgtaac catttattcg    1620
tactcgtctg gcgacgctag aaatctttca aaagtagagc tttctgcaga cttggtgaac    1680
ccaagaaaac aaaaagccgc tgatgaattt ttaattgatg ggcctgcatg gaaaagacaa    1740
aagagtgata cggatgcacc aaaagcagct ggaactggtg gctggctaga ggatacagaa    1800
tcatcgggac ttctaaaact ggaatccaag cccaggctaa ttgagaacgg tgtaacatct    1860 atgcatcaa gtgttatgcc cacgagtgct gtttctgtga gccaaaaagt acggacagct    1920
tcaactgata ctgcatcatt gcaatccctt ttgaaggata ttgcagtaaa tcctacaatg    1980
ctactgaatc tcctgaaaat gggagaaaga caaaaggtac ctgaaaaagc tattcagaaa    2040
cccatggatc caagaagagc agcacaactc cctggctctt ccgtacaacc aggggtatca    2100
acaccgctta gtatacctgc atcaaatgct ttagctgcta attctttaaa ctcaggagta    2160
cttcaggatt cttcccaaaa cgcccctgca gccgaatctg gaagcattcg catgaaacct    2220
cgtgatcctc gccgaatcct gcatggaagt actcttcaaa gaacggactc ttcaatggaa    2280
aagcagacca aagtgaatga tccttccact ctaggaacct tgactatgaa gggtaaggca    2340
gaagatttgg aaacacctcc ccagcttgat ccacggcaaa atattagcca gaatggtacc    2400
agcaaaatga aaatttcggg tgaacttctc agtgggaaga caccagactt ttcaacacaa    2460
ttcaccaaaa acctgaaaag tattgctgat atggttgtcg tatcacaaca acttggcaat    2520
cccccagcaa gtatgcattc ggtacagctt aagacggaga gagatgttaa acataatcct    2580
tcaaatccca atgcccagga tgaggatgtg tcagtttcag cagcatcagt aacggctgca    2640
gctggtccca ctcgttccat gaacagttgg ggagatgtgg aacacctatt tgaaggatat    2700
gatgacattc agagagtagc tattcaaaga gagagagttc gtaggttaga ggaacagaat    2760
aaaatgtttg catctcaaaa gctctctctt gtcttggata tagaccacac ccttctcaat    2820
tcagctaagt ttaatgaggt tgaatcccgc cacgaggaga tattaagaaa gaaggaagaa    2880
caagatcgtg agaaaccata tagacatctc tttcgtttcc tgcacatggg aatgtggact    2940
aaactaagac cagggatttg gaattttttg gagaaggcta gcaagctgta cgagttacat    3000
ctttacacta tgggaaacaa attgtatgtt acagagatgg ccaagctgct tgatcccaaa    3060
ggggttctat ttaatggacg ggtcatatcg aaaggagatg atggagatcc tcttgatgga    3120
gacgaacgag tacctaagag caaagattta gaaggagtta tgggtatgga atcgtctgtg    3180
gtgatcatag atgactctgt ccgagtgtgg cctcaacaca aaatgaattt aatagctgtt    3240
gaaagatatc tttatttccc ttgtagtaga cggcaatttg ggcttcttgg tccttctctt    3300
cttgagttag atcgtgatga ggtacctgag gagggcacat tggcatcttc attagcggtt    3360
attgagaaaa tacatcaaaa tttcttctcg cacacttcat tagatgaagt tgatgtgaga    3420
```

```
aatatttttag cttctgagca acgaaagata ttggctggtt gtaggattgt atttagtcgg    3480
ataatcccag tgggtgaagc caaaccgcac ttgcatcccc tgtggcaaac tgctgagcag    3540
tttggtgctg tctgcacaac ccaggtggat gaacatgtca ctcatgttgt cacaaattct    3600 cttgaaccg acaaggtaaa ttgggcacta accagaggta gatttgttgt tcatcctggc     3660
tgggtggaag catcagcttt tctgtaccag agagcaaatg agaacttata tgccatcaac    3720
ccgtaaacca atccatgat ccgccctctt aaatccccac catttggtgg aattgagact     3780
taagtaggcc tgaaaaccca ataagtcata ttgggttgat taggctaggc cccggggtac    3840
atacacattc ttttgcccca aaagaagcga attcattaaa atgccaaagg tattgggggc    3900
ttttaacaaa acgaactcca cattgtatca atggtctaga gtagatctac ttactttggg    3960
atggtgaagg aaactagtct gtctctggat ctaaaaaaaa taacaccaga gagacccagc    4020
attagaaagt atgatgtgcc aaggtcacgt gtcaaggag aggatcatgt tcaattttgg     4080
ttctcatctg ttgattcatg atcggtcaga taaatgtttg ttgtggtatt tatgtctctt    4140
gtcggaagca attctgatgg ggtaccaagg caacagagaa gagaagaaag ctttaattga    4200
aatgttcata tgccttacta atccccagaa ttaaatgtgg tggtggagaa accaaattca    4260
ttaagtatga caaacagaga ccacattaaa cagttacttg acgtctaaaa aaaaaaaaa    4320 aa                                                                    4322
```

```
<210> SEQ ID NO 3
<211> LENGTH: 5000
<212> TYPE: DNA
<213> ORGANISM: Arabidopsis thaliana

<400> SEQUENCE: 3
```

```
cgatttgctc atttggcaac aagttctaaa tttatatcac ttcaacacaa ttctctaaat      60
ctcttagaac attgtataac caatatagtt ggtgatgtga cacatgaggc cgtcaaaacg     120
tctgaatgtg tgtgagaaaa cattaagacg ttttggcggc ctttggatca aaatgcttgc    180
aattgcatag caaactcata ggtttatatg gacagttcga ggcattacaa agaaagagga    240
agccattagt gaatctgtct catgaatcat atttatatat gtcactagga gttaagatta    300
ttttcttatc aataattagc atgattcaac tctctaaatt actacattct ttcgagatct    360
cgaggatttc aatattatat gccaaaattt aacaatgtat tggaataaaa gtttctgaca    420
acacttggat agtttgaaga gtcagttagt ttaggcgaat ttttttttgat aatttggctt    480 ccaatgcaga caactggtgt ggctatatta ccgtgttctc aaagtcttta agcagcccaa    540
ttaacttagg catgcaaacg ccattgttaa tagggatgg gcacaatatt tagggcacaa     600
cctatacaca caagtggtta attgagaact tgagattatg gaccagattt tgaaaggtta    660 tcgtttata cacttcatat caactcatcg tatcatttca ttttgttcac atcattaatt     720 tcatttttg ggcatttaat ctatgtattt aaccaaaaaa caggaatttt attttaacaa     780
tatttatgat aatatcattg atccattgat ctattgccgc tttcaccatc accagttggc    840
aacccatctg ccactaccac tatgattcat ttagtttcca ttacatcaaa ttttcttgta    900
ataatcactt tttacaaccg aaatcgacat aagtgtatag gtcgaatcaa aacgccaacg    960 atttttatcag tttatgatgg tttagtaagt tcatattctt ggtcatatcg tttaaagcaa    1020
atttagttgt aaaagttaaa ttgagtggtc acaaatattt ttaaatatta gtagtttctg    1080
ttagtatcgt aattatgcaa tcctttccgt atattgtacg ttatttaacc aaaaaaagtt    1140
tcaatagttt attttctctt accctcaata atttggttaa caaatatata atccattaat    1200
```

```
tagtaatgac acgaaaacgc gtacggagac atgtcacatc aaatattcaa atccaaagca    1260
atttaacaga agatgaataa cgataatttt attggcttta gactttagta ttgaataatc    1320
aaaatcaata atctgtatat aaacaacaat aactctagtc gaccaaaaat tatattgagt    1380
atgataatgt catcttatca ccacgttata tacaaaaatg aattcgtgca tcgagacgta    1440
cgacacagca ttcctttgta cggaactaac tttaattaaa agttaatacc aaaattatat    1500
caagttactc aacatatgtg tatactaaag tattagaatt tgaatttcaa cagtttattt    1560
gtaccttcgg atcagagttg ccttaagact tcagaggaaa ttcattagtg atgactgttt    1620
aattcttcaa aaataagaaa ataaaaagat gtaataaaga tatcccttgt tgctgtgata    1680
atttatgttt tcaattttta ttgttggtta gaagttataa cttaaaatta tttcaaaatt    1740
aaagggacca acctatatta atatgagaac gtattcagtt gtaaacacac aattcccttta   1800 tactgataaa actaacaggg aaaaaacttg tttggttaac ttattacgag atgccataac    1860
aacaacaagt gcagcattaa tctatcacgg attcttttta gtgtatgttt gttacttttc    1920
accgcagatg gtatatgcat ggtttcattt ttgttcttat ttttattgtt gaatatggac    1980
caattattag aaagataaaa ttgaaatggt caatctatat atagtgatcc catgcttaac    2040
ggtacatgta catataatat aagagttgtt tataacttta tatacgtata cgaacaatat    2100
atacaaatta actagtgcaa gtggaaccct acgcatgatg tcacgaatat aattcggatg    2160
tagcttgttg aaattaaatt cattatttaa aatttcggta atcatatatt aagtgatacc    2220
atatttaatc aaatctattc ttatcagaaa ttaataatat agtaatcaca tcattgtaca    2280
tcatatatat catcgtatat ataagatcgt tagatttcat tatttgttgc ttgtgatttg    2340
atcactcttg caaatctaaa ttcatttcca tatatattta tgatatcgta tgatttattt    2400
ggtgttacct ctcggtaatt gaatttggaa atgctatgta tatggagcgt cgtccatgat    2460
ggacatatat gtgactgcgt atttacacac accgcacgta tgcttatttc acacgttaga    2520
agaagaattc aaagaagtcg gttctatttg tattcttgtg agatcatcaa tatgacaata    2580
tcgttctatt aatatacgta taattcatat gttgtcatgg tttcacatac catgtcgaca    2640
gtcgacgtac gtacaaaagt ataaatagta tgaatctaat aacagcacca agattgaagt    2700
tcatcttcta atcaaaacta tcataaagtg gtttcaaaat agtgtttttt ctgatgaaac    2760
tataactgag ttataatcaa tccgaaatta tataactaat tatatttggg aactagataa    2820
acgcaaaaac atgagcagtt tcttattttt tttgtccaga tttaaaattt ggagtgttaa    2880
aatatacgga gtgttacaca atgaaaacac aagaagtcaa gaacccataa gttattttaa    2940
ttaataatat tgtatttaaa gtgattatta aaaaataatg taaaaactga ttatttgttg    3000
acaaaaaaca gttagttata gttaaatagt attgatgcat atatatacta tctcattatt    3060
ttggtattac tcagtactca catctttaat aaagacaaag atagttagtg tataattcaa    3120
atcgaactca cagaagtcaa taagcgcgta aaaatacaaa aatatctggc agactttagc    3180
aaggtttgtt ttccaacaga aatggtcatt tcagaatcat ttacatatcc atatatatag    3240
ctcttaaatg gtatatattg ggtaatgggt attcgtttaa ataattttgt tttctgtaaa    3300
tttcaaatat taatctgatc agtttatcca tgtgtgtata tttagtgtat tatcatcaat    3360
atatgacata gacagacttt caagttggtg caagagggga tgaaaatttc ttcccagttg    3420
caagagtaag ctgactagca tttttttttt atatataatt tatttctcaa atggttttta    3480
ttattgtttt gttgacttta agtttttgcc ttttatggga ctgcaatcac ccgtgccaac    3540
```

```
ttttaatctc catcgcctaa aaaagaaaga aaaggctacc attatggacc gaaatattta    3600
agaccataat acaaaattat acgaatattt tctgtaactt atatatatga tcatttgaca    3660
aagcaaagtc aatcaaataa acttcaaaga aattatgagc ttataataag tttgatagtg    3720
ttaaatataa tcaaatcatt aaatttagta tttatttcat ctcggtttcc atttgataga    3780
tagataaatg aaagatagca tcgccaataa tgaaaaaact ttatttgatg gcaatacttt    3840
gttacatcat ttctgttttc ttaatttcat gtcgaaatat tgccatgatt gtgttcaaca    3900
taactagttt tgaggtaaca agttaaaaat ttgttatatt ttttgaatat gttattcagt    3960
tgaaagtcat ttagatgtaa gtaaaaacaa acataagaag ttaacatatc aatattaaca    4020
cagcgaataa tcattattac aaaaaaaagc aaaaaaatag aagaagatat tatatattgg    4080
agaatctttc tttagtctta gttgggaaga ttttgtgcta tgggattaaa ggtatccatc    4140
cctattctat gatagaggcg tggggttatt ggaccaatct atatatatta ccacaaggct    4200
taagatgaag tgataataca gtattattaa taccctccca aattattttt aaatatttat    4260
caaaagaagc ttacggtata gatcatactt gcagcattat tctataagtt tatttaattt    4320
cagtggctcg ttacgtgaac acaaggtaag ctaatagact tacgtgcccc attaaacaca    4380
tacataatta tacaagtatc atgaaactag tgacaaaacc tcgatcaaat aaagaaatta    4440
ccatgacgac aaaagataat taaaaaaaaa actactatat gtcatactca tgcatatgca    4500
tgtacaaatg ccgctttaaa tatttaattt agttaaagca atgatattta aattctctct    4560
acttcatata tattccaaaa gacatattgt caaattcctt tttttagtta tatataatca    4620
tatattcata ttgttatatt ttcaatattt aatagtaaga tggactttcc tgaatgttgt    4680
gtatgattta taatttgaga tattttgtcg gagatggata tttgacaagt taatgttact    4740
ttattaaaat tttctaaaca tttaggtacg aattgacttt tcaaaagtc aacacaataa    4800
attttaaaag tttaatgact taacgggttc acatgggaaa cgaaaacacc ctaaaccaca    4860
aacaatctaa tcttatttcc ttctttatat aaaccgctgt ttcccaaaag gcttgttctc    4920
gtcatatgta cttgtacacc aacccaccaa aagagataaa gaggaaaca aaaactcgaa    4980
aagagagaga tatatgggtg                                               5000
```

<210> SEQ ID NO 4
<211> LENGTH: 5132
<212> TYPE: DNA
<213> ORGANISM: Arabidopsis thaliana

<400> SEQUENCE: 4

```
cgatttgctc atttggcaac aagttctaaa tttatatcac ttcaacacaa ttctctaaat      60
ctcttagaac attgtataac caatatagtt ggtgatgtga cacatgaggc cgtcaaaacg     120
tctgaatgtg tgtgagaaaa cattaagacg ttttggcggc ctttggatca aaatgcttgc     180
aattgcatag caaactcata ggtttatatg gacagttcga ggcattacaa agaaagagga     240
agccattagt gaatctgtct catgaatcat atttatatat gtcactagga gttaagatta     300
ttttcttatc aataattagc atgattcaac tctctaaatt actacattct ttcgagatct     360
cgaggatttc aatattatat gccaaaattt aacaatgtat ggaataaaa gtttctgaca     420
acacttggat agtttgaaga gtcagttagt ttaggcgaat tttttttgat aatttggctt     480
ccaatgcaga caactggtgt ggctatatta ccgtgttctc aaagtctta agcagcccaa     540
ttaacttagg catgcaaacg ccattgttaa taggggatgg gcacaatatt tagggcacaa     600
cctatacaca caagtggtta attgagaact tgagattatg gaccagattt tgaaaggtta    660
```

| | |
|---|---|
| tcgttttata cacttcatat caactcatcg tatcatttca ttttgttcac atcattaatt | 720 |
| tcatttttg ggcatttaat ctatgtattt aaccaaaaaa caggaatttt attttaacaa | 780 |
| tatttatgat aatatcattg atccattgat ctattgccgc tttcaccatc accagttggc | 840 |
| aacccatctg ccactaccac tatgattcat ttagtttcca ttacatcaaa ttttcttgta | 900 |
| ataatcactt tttacaaccg aaatcgacat aagtgtatag gtcgaatcaa aacgccaacg | 960 |
| attttatcag tttatgatgg tttagtaagt tcatattctt ggtcatatcg tttaaagcaa | 1020 |
| atttagttgt aaaagttaaa ttgagtggtc acaaatattt ttaaatatta gtagtttctg | 1080 |
| ttagtatcgt aattatgcaa tccttttccgt atattgtacg ttatttaacc aaaaaaagtt | 1140 |
| tcaatagttt attttctctt accctcaata atttggttaa caaatatata atccattaat | 1200 |
| tagtaatgac acgaaaacgc gtacggagac atgtcacatc aaatattcaa atccaaagca | 1260 |
| atttaacaga agatgaataa cgataatttt attggcttta gactttagta ttgaataatc | 1320 |
| aaaatcaata atctgtatat aaacaacaat aactctagtc gaccaaaaat tatattgagt | 1380 |
| atgataatgt catcttatca ccacgttata tacaaaaatg aattcgtgca tcgagacgta | 1440 |
| cgacacagca ttcctttgta cggaactaac tttaattaaa agttaatacc aaaattatat | 1500 |
| caagttactc aacatatgtg tatactaaag tattagaatt tgaatttcaa cagtttatt | 1560 |
| gtaccttcgg atcagagttg ccttaagact tcagaggaaa ttcattagtg atgactgttt | 1620 |
| aattcttcaa aaataagaaa ataaaaagat gtaataaaga tatcccttgt tgctgtgata | 1680 |
| atttatgttt tcaattttta ttgttggtta gaagttataa cttaaaatta tttcaaaatt | 1740 |
| aaagggacca acctatatta atatgagaac gtattcagtt gtaaacacac aattccttta | 1800 |
| tactgataaa actaacaggg aaaaaacttg tttggttaac ttattacgag atgccataac | 1860 |
| aacaacaagt gcagcattaa tctatcacgg attctttta gtgtatgttt gttacttttc | 1920 |
| accgcagatg gtatatgcat ggtttcattt ttgttcttat ttttattgtt gaatatggac | 1980 |
| caattattag aaagataaaa ttgaaatggt caatctatat atagtgatcc catgcttaac | 2040 |
| ggtacatgta catataatat aagagttgtt tataacttta tatacgtata cgaacaatat | 2100 |
| atacaaatta actagtgcaa gtggaaccct acgcatgatg tcacgaatat aattcggatg | 2160 |
| tagcttgttg aaattaaatt cattatttaa aatttcggta atcatatatt aagtgatacc | 2220 |
| atatttaatc aaatctattc ttatcagaaa ttaataatat agtaatcaca tcattgtaca | 2280 |
| tcatatatat catcgtatat ataagatcgt tagatttcat tatttgttgc ttgtgatttg | 2340 |
| atcactcttg caaatctaaa ttcatttcca tatatattta tgatatcgta tgatttattt | 2400 |
| ggtgttacct ctcggtaatt gaatttggaa atgctatgta tatggagcgt cgtccatgat | 2460 |
| ggacatatat gtgactgcgt atttacacac accgcacgta tgcttatttc acacgttaga | 2520 |
| agaagaattc aaagaagtcg gttctatttg tattcttgtg agatcatcaa tatgacaata | 2580 |
| tcgttctatt aatatacgta taattcatat gttgtcatgg tttcacatac catgtcgaca | 2640 |
| gtcgacgtac gtacaaaagt ataaatagta tgaatctaat aacagcacca agattgaagt | 2700 |
| tcatcttcta atcaaaacta tcataaagtg gtttcaaaat agtgtttttt ctgatgaaac | 2760 |
| tataactgag ttataatcaa tccgaaatta tataactaat tatatttggg aactagataa | 2820 |
| acgcaaaaac atgagcagtt tcttattttt tttgtccaga tttaaaattt ggagtgttaa | 2880 |
| aatatacgga gtgttacaca atgaaaacac aagaagtcaa gaacccataa gttatttaa | 2940 |
| ttaataatat tgtatttaaa gtgattatta aaaataatg taaaaactga ttatttgttg | 3000 |

```
acaaaaaaca gttagttata gttaaatagt attgatgcat atatatacta tctcattatt    3060
ttggtattac tcagtactca catctttaat aaagacaaag atagttagtg tataattcaa    3120
atcgaactca cagaagtcaa taagcgcgta aaaatacaaa aatatctggc agactttagc    3180
aaggtttgtt ttccaacaga aatggtcatt tcagaatcat ttacatatcc atatatatag    3240
ctcttaaatg gtatatattg ggtaatgggt attcgtttaa ataattttgt tttctgtaaa    3300
tttcaaatat taatctgatc agtttatcca tgtgtgtata tttagtgtat tatcatcaat    3360
atatgacata gacagacttt caagttggtg caagagggga tgaaaatttc ttcccagttg    3420
caagagtaag ctgactagca ttttttttt atatataatt tatttctcaa atggttttta    3480
ttattgtttt gttgacttta agttttgcc ttttatggga ctgcaatcac ccgtgccaac    3540
ttttaatctc catcgcctaa aaagaaaga aaggctacc attatggacc gaaatattta    3600
agaccataat acaaaattat acgaatattt tctgtaactt atatatatga tcatttgaca    3660
aagcaaagtc aatcaaataa acttcaaaga aattatgagc ttataataag tttgatagtg    3720
ttaaatataa tcaaatcatt aaatttagta tttatttcat ctcggtttcc atttgataga    3780
tagataaatg aaagatagca tcgccaataa tgaaaaaact ttatttgatg caatactttt    3840
gttacatcat ttctgttttc ttaatttcat gtcgaaatat tgccatgatt gtgttcaaca    3900
taactagttt tgaggtaaca agttaaaaat ttgttatatt ttttgaatat gttattcagt    3960
tgaaagtcat ttagatgtaa gtaaaaacaa acataagaag ttaacatatc aatattaaca    4020
cagcgaataa tcattattac aaaaaaaagc aaaaaaatag aagaagatat tatatattgg    4080
agaatctttc tttagtctta gttgggaaga ttttgtgcta tgggattaaa ggtatccatc    4140
cctattctat gatagaggcg tggggttatt ggaccaatct atatatatta ccacaaggct    4200
taagatgaag tgataataca gtattattaa taccctccca aattattttt aaatatttat    4260
caaaagaagc ttacggtata gatcatactt gcagcattat tctataagtt tatttaattt    4320
cagtggctcg ttacgtgaac acaaggtaag ctaatagact tacgtgcccc attaaacaca    4380
tacataatta tacaagtatc atgaaactag tgacaaaacc tcgatcaaat aaagaaatta    4440
ccatgacgac aaaagataat taaaaaaaaa actactatat gtcatactca tgcatatgca    4500
tgtacaaatg ccgcttttaa tatttaattt agttaaagca atgatatttta aattctctct    4560 acttcatata tattccaaaa gacatattgt caaattcctt ttttttagtta tatataatca    4620 tatattcata ttgttatatt ttcaatattt aatagtaaga tggactttcc tgaatgttgt    4680
gtatgattta taatttgaga tattttgtcg gagatggata tttgacaagt taatgttact    4740
ttattaaaat tttctaaaca tttaggtacg aattgacttt tcaaaagtc aacacaataa    4800 atttaaaag tttaatgact taacgggttc acatgggaaa cgaaaacacc ctaaaccaca    4860
aacaatctaa tcttatttcc ttctttatat aaaccgctgt ttcccaaaag gcttgttctc    4920
gtcatatgta cttgtacacc aacccaccaa aagagataaa agaggaaaca aaaactcgaa    4980
aagagagaga tatatgggtg aggtggctta tatggacgaa ggagacctag aagcaatagt    5040
cagaggctac tccggctccg gagacgcgtt ttccggcgaa agttccggta cgttttcacc    5100
ttcgttttgc ctaccgatgg agacgtctag tt                                  5132
```

<210> SEQ ID NO 5
<211> LENGTH: 6110
<212> TYPE: DNA
<213> ORGANISM: Arabidopsis thaliana

<400> SEQUENCE: 5

```
cgatttgctc atttggcaac aagttctaaa tttatatcac ttcaacacaa ttctctaaat      60
ctcttagaac attgtataac caatatagtt ggtgatgtga cacatgaggc cgtcaaaacg     120
tctgaatgtg tgtgagaaaa cattaagacg ttttggcggc ctttggatca aaatgcttgc     180
aattgcatag caaactcata ggtttatatg gacagttcga ggcattacaa agaaagagga     240
agccattagt gaatctgtct catgaatcat atttatatat gtcactagga gttaagatta     300
ttttcttatc aataattagc atgattcaac tctctaaatt actacattct ttcgagatct     360
cgaggatttc aatattatat gccaaaattt aacaatgtat tggaataaaa gtttctgaca     420
acacttggat agtttgaaga gtcagttagt ttaggcgaat ttttttttgat aatttggctt     480 ccaatgcaga caactggtgt ggctatatta ccgtgttctc aaagtcttta agcagcccaa     540
ttaacttagg catgcaaacg ccattgttaa taggggatgg gcacaatatt tagggcacaa     600
cctatacaca caagtggtta attgagaact tgagattatg gaccagattt tgaaaggtta     660 tcgtttata cacttcatat caactcatcg tatcatttca ttttgttcac atcattaatt     720
tcattttttg ggcatttaat ctatgtattt aaccaaaaaa caggaatttt atttaacaa     780 tatttatgat aatatcattg atccattgat ctattgccgc tttcaccatc accagttggc     840
aacccatctg ccactaccac tatgattcat ttagtttcca ttacatcaaa ttttcttgta     900
ataatcactt tttacaaccg aaatcgacat aagtgtatag gtcgaatcaa aacgccaacg     960
attttatcag tttatgatgg tttagtaagt tcatattctt ggtcatatcg tttaaagcaa    1020
atttagttgt aaaagttaaa ttgagtggtc acaaatatt ttaaatatta gtagtttctg    1080
ttagtatcgt aattatgcaa tcctttccgt atattgtacg ttatttaacc aaaaaaagtt    1140
tcaatagttt attttctctt accctcaata atttggttaa caaatatata atccattaat    1200
tagtaatgac acgaaaacgc gtacggagac atgtcacatc aaatattcaa atccaaagca    1260
atttaacaga agatgaataa cgataatttt attggcttta gactttagta ttgaataatc    1320
aaaatcaata atctgtatat aaacaacaat aactctagtc gaccaaaaat tatattgagt    1380
atgataatgt catcttatca ccacgttata tacaaaaatg aattcgtgca tcgagacgta    1440
cgacacagca ttcctttgta cggaactaac tttaattaaa agttaatacc aaaattatat    1500
caagttactc aacatatgtg tatactaaag tattagaatt tgaatttcaa cagtttatt     1560 gtaccttcgg atcagagttg ccttaagact tcagaggaaa ttcattagtg atgactgttt    1620
aattcttcaa aaataagaaa ataaaaagat gtaataaaga tatcccttgt tgctgtgata    1680
atttatgttt tcaattttta ttgttggtta gaagttataa cttaaaatta tttcaaaatt    1740
aaagggacca acctatatta atatgagaac gtattcagtt gtaaacacac aattcccttta   1800 tactgataaa actaacaggg aaaaaacttg tttggttaac ttattacgag atgccataac    1860
aacaacaagt gcagcattaa tctatcacgg attctttta gtgtatgttt gttacttttc     1920
accgcagatg gtatatgcat ggtttcattt ttgttcttat ttttattgtt gaatatggac    1980
caattattag aaagataaaa ttgaaatggt caatctatat atagtgatcc catgcttaac    2040
ggtacatgta catataatat aagagttgtt tataacttta tatacgtata cgaacaatat    2100
atacaaatta actagtgcaa gtggaaccct acgcatgatg tcacgaatat aattcggatg    2160
tagcttgttg aaattaaatt cattatttaa aatttcggta atcatatatt aagtgatacc    2220
atatttaatc aaatctattc ttatcagaaa ttaataatat agtaatcaca tcattgtaca    2280
tcatatatat catcgtatat ataagatcgt tagatttcat tatttgttgc ttgtgatttg    2340
```

```
atcactcttg caaatctaaa ttcatttcca tatatattta tgatatcgta tgatttattt    2400
ggtgttacct ctcggtaatt gaatttggaa atgctatgta tatggagcgt cgtccatgat    2460
ggacatatat gtgactgcgt atttacacac accgcacgta tgcttatttc acacgttaga    2520
agaagaattc aaagaagtcg gttctatttg tattcttgtg agatcatcaa tatgacaata    2580
tcgttctatt aatatacgta taattcatat gttgtcatgg tttcacatac catgtcgaca    2640
gtcgacgtac gtacaaaagt ataaatagta tgaatctaat aacagcacca agattgaagt    2700
tcatcttcta atcaaaacta tcataaagtg gtttcaaaat agtgtttttt ctgatgaaac    2760
tataactgag ttataatcaa tccgaaatta taaactaat tatatttggg aactagataa      2820
acgcaaaaac atgagcagtt tcttattttt tttgtccaga tttaaaattt ggagtgttaa    2880
aatatacgga gtgttacaca atgaaaacac aagaagtcaa gaacccataa gttattttaa    2940
ttaataatat tgtatttaaa gtgattatta aaaataatg taaaaactga ttatttgttg      3000
acaaaaaaca gttagttata gttaaatagt attgatgcat atatatacta tctcattatt    3060
ttggtattac tcagtactca catctttaat aaagacaaag atagttagtg tataattcaa    3120
atcgaactca cagaagtcaa taagcgcgta aaaatacaaa aatatctggc agactttagc    3180
aaggtttgtt ttccaacaga aatggtcatt tcagaatcat ttacatatcc atatatatag    3240
ctcttaaatg gtatatattg ggtaatgggt attcgtttaa ataattttgt tttctgtaaa    3300
tttcaaatat taatctgatc agtttatcca tgtgtgtata tttagtgtat tatcatcaat    3360 atatgcacata gacagacttt caagttggtg caagagggga tgaaaatttc ttcccagttg   3420
caagagtaag ctgactagca tttttttttt atatataatt tatttctcaa atggttttta    3480
ttattgtttt gttgacttta agttttgcc ttttatggga ctgcaatcac ccgtgccaac      3540 tttaatctc catcgcctaa aaagaaaga aaggctacc attatggacc gaaatattta        3600
agaccataat acaaaattat acgaatattt tctgtaactt atatatatga tcatttgaca    3660
aagcaaagtc aatcaaataa acttcaaaga aattatgagc ttataataag tttgatagtg    3720
ttaaatataa tcaaatcatt aaatttagta tttatttcat ctcggtttcc atttgataga    3780
tagataaatg aaagatagca tcgccaataa tgaaaaaact ttatttgatg gcaatacttt    3840
gttacatcat ttctgttttc ttaatttcat gtcgaaatat tgccatgatt gtgttcaaca    3900
taactagttt tgaggtaaca agttaaaaat ttgttatatt ttttgaatat gttattcagt    3960
tgaaagtcat ttagatgtaa gtaaaaacaa acataagaag ttaacatatc aatattaaca    4020
cagcgaataa tcattattac aaaaaaaagc aaaaaaatag aagaagatat tatatattgg    4080
agaatctttc tttagtctta gttgggaaga ttttgtgcta tgggattaaa ggtatccatc    4140
cctattctat gatagaggcg tggggttatt ggaccaatct atatatatta ccacaaggct    4200
taagatgaag tgataataca gtattattaa taccctccca aattattttt aaatatttat    4260
caaaagaagc ttacggtata gatcatactt gcagcattat tctataagtt tatttaatttt  4320 cagtggctcg ttacgtgaac acaaggtaag ctaatagact tacgtgcccc attaaacaca    4380
tacataatta tacaagtatc atgaaactag tgacaaaacc tcgatcaaat aaagaaatta    4440
ccatgacgac aaaagataat taaaaaaaaa actactatat gtcatactca tgcatatgca    4500
tgtacaaatg ccgcttaaa tatttaattt agttaaagca atgatattta aattctctct      4560
acttcatata tattccaaaa gacatattgt caaattcctt tttttagtta tatataatca    4620
tatattcata ttgttatatt ttcaatattt aatagtaaga tggactttcc tgaatgttgt    4680
gtatgattta aatttgaga tattttgtcg gagatggata tttgacaagt taatgttact     4740
```

```
ttattaaaat tttctaaaca tttaggtacg aattgacttt ttcaaaagtc aacacaataa    4800
attttaaaag tttaatgact taacgggttc acatgggaaa cgaaacacc ctaaaccaca     4860 aacaatctaa tcttatttcc ttctttatat aaaccgctgt ttcccaaaag gcttgttctc    4920
gtcatatgta cttgtacacc aacccaccaa aagagataaa agaggaaaca aaaactcgaa    4980
aagagagaga tatatgggtg aggtggctta tatggacgaa ggagacctag aagcaatagt    5040
cagaggctac tccggctccg gagacgcgtt tccggcgaa agttccggta cgttttcacc     5100
ttcgttttgc ctaccgatgg agacgtctag tttctacgaa ccggagatgg agacaagtgg    5160
cttagatgag ctcggtgaac tttacaaacc cttttaccct ttctccacac aaacgatcct    5220
cacaagctcg gtctctctcc ctgaagattc aaaacctttc cgagatgaca agaaacaacg    5280
atcacatggt tgtcttttat ccaacggatc aagagctgat catatccgaa tttcagaatc    5340
caaatcaaag aaaaggtcag tattcttgaa gttctttaag agggttcttt aaaatgcgaa    5400
atttggttct aaaatattct tatcaaatta atcatataag aaaattgggt ttaagttgtc    5460
ttagttacta gtataaatca ttagtaaaat aaatagtaac gcatacgcgt tttgttatat    5520
aattcgtata aatatacata tatatgctcc ttgttgaata attagatcat aaataaataa    5580
tataagtttg aatttggaca gcaagaagaa tcaacagaag agagttgttg agcaagtgaa    5640
agaagagaat ctgttgtcgg acgcatgggc gtggcgtaaa tacgggcaga aacccatcaa    5700
aggatctcca tacccaaggt cttaaccaa tcccggttta atctcatctt cctttctcct     5760
aatcaaacat aaccggttta ctaatctttc aattttggtg tttctttttt ttcaggagtt    5820
attacagatg cagtagctca aaagggtgtt tggcaagaaa acaagtcgaa agaaatcctc    5880
aaaacccgga gaaattcacc ataacataca ctaatgagca caatcatgaa ctaccaaccc    5940
ggagaaactc attagccggt tcgactcgag caaaaacttc ccaacccaaa ccaaccttaa    6000
ccaaaaaatc cgaaaagaa gttgtttctt cccctacaag taatcctatg atcccatccg     6060
ctgatgaatc ttctgttgcg gttcaagaaa tgagcgttgc ggaaacgagt                6110
```

<210> SEQ ID NO 6
<211> LENGTH: 7389
<212> TYPE: DNA
<213> ORGANISM: Arabidopsis thaliana

<400> SEQUENCE: 6

```
ttcagaaaca aacctcgctt gtctacaata caaattagag ttggtagtgt aataatgggc      60
ttaaaattcc aaggttggcc tgatttcatt ctagaaaatt ggcggacaga tctaatagtc     120
cgtcaaggcg attcagatat ggccggattc gatgagcttg ccatttttctt atctaacttt    180 tcatgttggc cacgagccag cctgtggccc gtatattcaa ataatgggaa ggctcgaccg     240
cgtttaaagt tgccgggcta gactaatcga cccggactca aaacaagtcg ggcctgttaa     300
tcaatgttca actatttact tttctctagc gtaatccgaa cctcaaagat tcaaggaaaa     360
ttagacaaga accatatagt atatataacc ttcatttggc catgtggcca aatccatttt     420
gtgatggtta gaaacttaga atacatatat agtctttaag attattgcat gggtgaacag     480
acgttgatat gctctaattg ctcatgtatt cattacattc gtaggttata atgagttaag     540
cattaaagag atgttggtgt agtcatatat agatcatgca cttccactaa caatataagc     600
gtttagaaat ggtatcggtt ttccttttga tgaaaaggat aatacatcat ataagcattg     660
aaaaatgatt aagttcccaa gtctctttga actcgtaatt ttttgctag atctatcgac      720
```

```
tacaaaaaaa aacgcaattg catctttatc gtacattggg tcaaccatat aattttatga    780
aataaattat ttttcatagg ttgatagtat tgttaaggag ttgtgttatg tggtctacct    840
atatttctta cctttttaaa tgcatattta cactttgctg cgattttcaa atttattgac    900
ttatgagaga attattaaga aaccactaaa tcaccctaaa ttgtttgaaa tataaattca    960
aaacaaataa atcataatcc atacatatgc tatatgtagg atatatataa taatgcatgc   1020
cccgcctttt aagaacataa agatcacaat attatttttt atttgaaaaa caaaaaattt   1080
cttaaagtat tgtctttctt tgactcttat tattagacaa aaggctcttt atttagattc   1140
tgacgaaatt gaaatggttc atgcatactt ggactattgt aagaaaggtt tctctaaaag   1200
ttaaaaacac atgctaatta actacttacc aaatttattt tggtcttgca atgtttggtg   1260
agatttggaa taaagttaca tattggtctg ccagacatgt tgttacttgt ttagtacatg   1320
tggggtaaaa ttgaatagga ccccttaat catggtacga tacaaggtct acgagcctca   1380
acaacaacaa gaacattatt tccgaagctt gagctacttg gcacatatca ttcaaagatg   1440
aaatcggaaa atgcagccag gttggagact cgacttatgg aatatctagt agttatatac   1500
tagtctatgt tccatcacac ttccaatgct tatatatatg ctaataaagt ctataaaata   1560
acaaattatt agacaatttt cgaccaaatg attatagttc tctttttct gtacgtggaa    1620 atttctctat aaaacaaatg agagcttctt ctattcttca acatgaagac aggaatcttt   1680
ggccattttc gtaaatggca gtcacaagag acagtcgtaa atggcagacc aattccttga   1740
tatgcacttt ggctctcaaa agaaatttat tattttatc tcttttttgtt tacttttgtt   1800 aattcggtat aaagatggca gacatagtac ggaaccaatg attcttttcg tcaaaccaac   1860
caatgttttt ctctccttca tgtttgaagg tatttgaaat tgattatgac tttcgagaag   1920
ctataataaa taatcaagag ttcccttttc cttcttttc ttcttattta ttaggtaaat    1980
aaaatcaaac ttctcaaaag agaatatgtt gaatcactta ccaaaaaaaa aaaagagaat   2040
atgttaaatc cttaataaat aaacaaactc ttacaaaaag aaaaaaatat tgtatcagag   2100
aaaatacatt gttcattttt tctaagatta cataatatat tttttaatat gacatttaaa   2160
tagacatata tatccctttt taagttaatc tctataattt gttttcagaa gaaaaaaaca   2220
tgtggttcct cttaaccaaa aaataaatat ataaattaat ttctgaaatg gtataatgat   2280
taaaaaaaat aaagaggcct gatgatagta ttttttggata agagtcaaaa tcttcagttt   2340
tatgcaaaac aaatcttctt ggccaaaact aagagacgaa tctcattcag ttgcaatcac   2400
gaggtctaag ttagtcaaaa ttagattgat aagaaagtgt tattgataac gtctatgtta   2460
ccttcttctt ccgtcgttga acttttttggc ctcattgcct tctactagtc atatagatag   2520
acctcttttg gacttatcca ctctttataa aagtcttaat atacaatgac ttagtgcccc   2580
caaaaaatca atgtaaagta tcaataagaa agaccgcaat tgattggtcc cttggttata   2640
ttaaaaacct ttgggtcacc caaaatttaa tatgagttcg aactctcgtg ggaaatcaaa   2700
atgatagtat aaaaccactc tagaagagta tatgaccagg aaagtatcaa taagtacaag   2760
aaaagagaat tttggatgtt ttcactattt tattgatttg attttttaaaa ctttgaaaac   2820 atgggactca aaagcacaag gtttattctt ttcttcgttt cttgttgacc ttattgccaa   2880
agcagcagct agtaaagaaa cttgttcata tacgattcaa tgttctaaaa gatgttagtt   2940
tctagttgga tagaaaattg agtttactaa aaacttagac tattacaatt tgtctaagat   3000
tggtaaagag tggtccatac catatcgtat tactcggcta atcattatga ggtgaacata   3060 tcttttcataa aaagttcaaa tgagcatatc tttcataaaa agttcaagac tctatttcac   3120
```

```
aataaactag tagattaaaa atctagagtc tagtactagt atagagtaga ttatttatag    3180
acaaataaaa gtataagcaa aatctaaaac ttatgaatta cagtttgtta aaactttcac    3240
atatgaggta aagatttatg ataagaagtt tttgatcaag tgatcacata atgtcataat    3300
tttcacatag tatcaaatat ccgaattagc tatgttaccg ttcatttgaa caaaaaaaac    3360
agaagatatg ttaccgttcc taaaacaaga tttagattat acgaaaaaca accataatct    3420
cgaataaatc agaatcctat atctaaatta attttgagaa actcataata gttcgtggca    3480
catatgattc ttctattccc tttgataatt acaccaatca aacctgactt cattttattt    3540
tttaagaaaa ggaaaatata taaaatatta atttaatata aatcttggac ggttgaaaca    3600
ttaaatttca ccgatttgga taaaatcagg ttgctgactg cgtcaaaatt taagaccata    3660
tatgtggtcg gattcaaatc taaacctctc gtacattcat aaaagttgga agatgtctca    3720
catgatctca tctatatact tatatattca tataggggaa aacacaaaag tacataaaga    3780
tgtcataaaa agaagtacaa aactaaatat taaagtgtga aaagcatcaa tagtcagatg    3840
gtttacttgt aaaaccaaaa cttatgtcca caagatttct acgtcatgcg aactcggcca    3900
cgttgtgtag tactatcatg ttggtcaatg caaatctcag acagctctgc agattttctt    3960 ctattttct  tcaactcatt taattgtttt ggggaaaaaa atattttga tcgctaaaaa    4020 cttaattttt tagtggacct gttttttgaca tcttacacgc tttcttggct ccttcctcag    4080
tcttaaatgt aaaatgaatt aaatacataa tcctgcaact taatcgtggc ttaaattaat    4140
caaaattata ctataattca ttgattattt tttcaaataa agtttatcta cggcaagtac    4200
tgtagacttt gaagagttct tgatgatgaa gaaaccttt aaaaataaaa taaccaataa    4260
acagacaaac ttgtaattga agaaaaaatt gacctacatt aacaaactga agcagattag    4320
tggcttataa atcgatctag agtagagtaa taattcgatc aaaatgaaaa ttttctgcag    4380
attaattttc ataaataaac ataaacgcat cgtgagaatc cgtgagctta ttttgaaaat    4440
tatagaggaa aaaattaggt aaaaaaaaaa atataattag ttgcccacaa gacaggtaat    4500
attaacacga gggacggaga aaagtgccaa aaaggtcaga agaaaagaaa atgagatttt    4560
ttgtaacctt attaatacaa ttagtttaac gtgattagag agagatttga aaaggtaaaa    4620
aagtcaaagc taatgactcg gtcgttccgg tagacagtca accgatctac acatctcttt    4680
tgtcaatacg tgggagccct ttaaggcttt tatcactatt attcttatta taacatgata    4740
aaataaaata aacatgatct ctcttttcttt ctgtctattt gtttctctta tttctacgtg    4800
tgtggactca aactaaaatt tagttttat tatcttctcg aattttaaat tataaggtca    4860
tgccaaataa ggtgacacgt ttcttcacta tctagttatt ttagtcattt gacatagcat    4920
atcagttttt ttttgttttt ttcgttggtg gtttttaatca tcaaactttg gcgatgaaaa    4980
cataaaaagg aaatcaacag taaaacaaat atcaaatata attatgatac tataaatttg    5040
taacattact atatgaacaa cataactaat tcaccaacca aattttttt ttctttctaa    5100 taaggtttat tatgggcaac acatgttatc acgataaata aatatagac tatttggata    5160 tgtgttatta gttgtattct ttttctttct tatttttttt tattttttatt tttttctata    5220 ttttcattaa ctattatttt ataaggtaaa aatataaata ttaaaataca ttcgtctgct    5280
aaaattatcc aatgtaatat tgcaattcaa aattaattgt ttcagaaaat aatctcagta    5340
gaatgcgctc ttataaccgc atgtagccaa ccaatgagcg attccaatga ttagtaacac    5400
taaatctctt cgacttttct aaatttgttg aacctgtttc gatttcttta tccggtttgt    5460
```

```
atagtaccat ttttggtta tccttcaaca aatttaacaa aaaaaataaa aaaattgcat    5520
ttacattatg tagtagtcta ataaatata attatagata atagaaaagt caatagttct    5580
aatatgataa caacaaaaga aaatgtatac tttaaaatct gaaaattacc attcttttat    5640
ttgttatccc aaacataagc catgtactat aattaggtta ttgtaattta ttataaaaaa    5700 aaagaaaga atattcctgt acttcatgat ttcttttgt aacgaagtac ataaaatttt    5760
caaatcacat gtggtaacca tgatttaaca aaaattaag tcggtgacaa gcaacgaaac    5820
ataaataatc gactttgtca agatatgtat aaaaatcgac tttgtattta gagaacaagg    5880
tcttcattat ttttcttttt taacattaga gaaagagaac taaaggtcta cttcaagaaa    5940
acaagaaact aggtgcttag ctttaataat atatcaaaga aaaatgggtc aaaaaataaa    6000 ttattcatg agtggggccc ggccggccac ggaagtaaga cctaacgacc agcgcaaccg     6060
gtcaccagtc aagactatta gaagccgggc cgtcaaaatc gttgactcgg ttttgtttc    6120 caactgtttt tgtattttgt taaaaataaa ttaatactaa taaataagct gaaaaaaaag    6180
aaaagagaaa aggtataatc acgtggaacg cgccgcagta acggagcgg tggatcaaac    6240 tttttcgtccg tttgatcaaa cagaagagaa ctagtcaatg ctctttcttc atatcacaat    6300
ttaatagtct caagacgatt acgccacata accattttct cgtgatttcg acatcaaaat    6360
ttaataaaag gaactgattg attggtcatc atgttacaag tgtcaaatga gctaatccgt    6420
tttacagtgg catagtttac gatcaattta caatttttg gttttataac atacttgtag    6480
ttaaaactat ttataagcta tttatagtga gttagcttat aaaaccctat tcttttatct    6540
aaaattatgt tttgactcgt ttcatgataa aattttatcc ttttcatcgg aataaaaaac    6600
tttattattt atttggcaaa ataattggtg taaaaattat gtatatgtta ataacaaaaa    6660
atattaatct gattcataat cttaaaaaag aaaaattct tgaaataaac tttagacatt    6720
gtaaataaaa aaacattatt tttatataat gggatgttta tatgtaattt tttataaaaa    6780
aataaaagtt gttactagt aatccgattg gctttaacta tcgtcgccaa aagaataatg    6840
tagaactgac tttgaggtaa aactaaaaga aatttgtaag ataatagtca cattaaatgc    6900
taaaattaat acatactgat atatcgtata aaatttatga aaactacacc ttaacctgaa    6960
tcatacactg taataaaaaa aacaaattat atataaaccc taaaaactaa tcataaatcc    7020
caaacggtgt actctctatt agctttgaaa ggattgccca attgtttgtt aaaaatttct    7080
aataatagta caatgttttg tttcattttt ccttttcgtc aacctgttac ccaatagcaa    7140
atgaagtttt tatgtgtgtg tgtgtgtgtg aatttccatg aaaatgaaac gggcttagaa    7200
tcccggtgta ttatgggtcg ggtcgtaacc gggcaatgac gcaggatctg acgtaaaact    7260
cccaagaatt ttttaaaaa gtctccggaa aataaaatca aagttcatta acttaaaaag    7320
aaaaaacaaa atcggtccac gtcccaaacc ctttttatag gagagtctta tgttctggca    7380
gaagacttc                                                            7389
```

<210> SEQ ID NO 7
<211> LENGTH: 2000
<212> TYPE: DNA
<213> ORGANISM: Arabidopsis thaliana

<400> SEQUENCE: 7

```
acgctacaga accaactggt ttatcatagt atctcgcata ttaacttagg ctagagagcc      60
aacctttttg aattaatgaa aaagttgaga cacaaccact aaactttacg gcattaataa     120
cggatctcat ttatgaacct gcgtacaaat ttggtctgaa gttaagtggt actatcccgg     180
```

```
aaataactta aatcttatcc taaactatat tctttccatt ttatagtacg agatgttttg      240
gaaaaaaaaa caaatagttt cataataaag taatattttc aagttcttat gcaatatttt      300
atgattagtt attagttata ttatgcattt tctttatgtt tggttgaact ttttaaaaat      360
atgtaatttt taatatacgt gtttttagtt aaacatctta tattttaaaa cggattaagt      420 atcttttag tcataattta tcttatcaca caaaaaagta atactttgtc gattcttaac      480
ccatgcaatt gtttatgtgt tctgaaattg attgatatga tcctagctca actggcgtta      540
atagacttcg tatgaaggga aaaaatttca aaatcattaa tttaaaagtt cgacgtgaaa      600
aaatgtaata atttaacatt ctcttataat gcttccgtaa gataaattta tggactatta      660
tccgactttt tgataatggg tatgcaaaaa cttgtcatat ctaaaaaaaa tatcaccaat      720
gttaatttat acttgggcat aaatgtatca ttaaaaaaac cttggtggct tggtgcatat      780
agaagagagt gaggctgtga gggagcacta tagaccaact agacatctct aagcgaggag      840
aacccatccg catcgcatgt atgcattgag atagctaggg cctaggggcc attgagtcga      900
tcgaccacat acacctcttt aaataatctt ctaatattaa agttttaaat caatgccccg      960
cccaactcta cctttccac gaaaacggaa taaagtgttt ccgggtgaaa gaaaatactt     1020
ttcaacgata gattgtgttg ctatttttat agaatatgtt aaatttaagt ataatataag     1080
ataggttcct ataaaaaaat tgggtagaaa agtttagctt tgatactcca tatagtttat     1140
atattagtgc agcgaggtga tacgtttact agtctaactt aacaaaaaaa aaagagttaa     1200
ttagtttata tattgattct ttcaacgtaa tcaatctgat ttagataatc cgtcccaact     1260
cccaattata tctgtcattc aagtatttga ttacaagggc aattcatttc ggactagttg     1320
attgtaaatt tcgtgtctcg ttatctattt gaaatagtag gtctatttag ggggtataca     1380
tctggattga tagctgataa ggactatata catgtctttt tgaattttg atatataaac     1440 tactattcaa aattatcttc atagaaaaac ggatcatatc atttggatat caaatttaac     1500
tcgagatttc aaataaataa ttcactattc caactgatct tactacatca gtaaaaaaaa     1560
attggtagta caatctcgag gaacaaaaaa gtttacaaat gaaatttaga atcttgttta     1620
atctttaaat ggatagtttt tcataactct tttaattagt ctagttttg atacaaattt     1680 tatccggtta tagaaaacat taaggaccc taagtttgga tttcagcaaa attatatata     1740
ttccattctc acttagggat gaaatgacat cattcatcac tacgtcattt gagcttacgt     1800
caagctcacc ataagcaaaa gaaatgggtg gataagttca agttccatct catttcctca     1860
cacatctctc tttcttcctt ctcatttcct cgcatcttcc tctaaaaaaa aaatcaaag     1920 aaaccaacaa aataaaaagt gcccatcatt acaaatctta tttccacctt atatttacac     1980
acacttctct tctttccttt                                                2000
```

<210> SEQ ID NO 8
<211> LENGTH: 2000
<212> TYPE: DNA
<213> ORGANISM: Arabidopsis thaliana

<400> SEQUENCE: 8

```
atgataaaag ggaaaatcca cgcggagaga ggtttgaaat gtcttcggtc caatcctgtc       60
cttttgaata ttgattttct ttttgatttt tcttgctttt tattaatcaa caaatctgtt      120
ttttggaatt acgttttttc tacgttgaag tgattttttt tcctttgta aaaggcctac      180 gttgaagtaa aattacataa ataaatgtat gttatgaata tcgacccaaa aaacaaatta      240
```

```
tttctacact atactttgcg caaatcaaat ctatcgaaaa cgattttggt aatcccattc        300
ccatgagtga gttttgaccc aaaacaaatt taaaaaagta accatttcat tagtaaaacg        360
gtaaatatgg ttcataaacc ttttagtggt tattggtcct gtacactaca ctcgtgtgtg        420
tcaacttcag ctatgagatt tttgctgtaa cttttttggat aacggttcaa ttattacaaa       480
ggttatttct tacgtatgag aggtccaaat tacaattgaa taatatttga tgacatacaa        540
agttaaaaag gattaatcat aagaaatgaa tgttggaatg gaatgcatct atcgatctga        600
ctactttaga tagcttgatg ttggacttag tcagcaaaga ccttatcata ctcttgttgt        660
attgtatata tcgtatcaca cagtgactgg ttttttctac ttttctcttt ggaacatatc        720
aatcattatg tataaataaa ttttgtccaa attaatggcc atttgtctca accataaata        780
aatatttatt cacacaccta tatgactatt tgagataatt ccatggtgac ttggtcagca        840
aaaaccttgt catactcttg gtgtattatc acataacttt gtagattata ttcttatgga        900
acatatcata tatatttgtc caaattaaac ccatttgtat tattttcccc tctcgagttt        960
aatatttctt atttagaaac agttaacaac ttgacatagc tcacataatc actcacagac       1020
tatatatgta taagcaacta ccatttttaaa tattatttag ttatattgtt agactgcaac      1080
tattatttat tttctttgcc aaacaaattt atatttttttc atgttaatac aatattatat     1140
cttgaacaaa tgtatgctta aatatattga cacaaaacaa aaacatatag gggtttttag       1200
gaagaaattt tgtacagatt aattaatcct catcagattt ttattttata tcttattttt      1260
agaagtgtat gatttttaaaa ctagaacaat caaatcttag taaatttcat tcaacataat     1320
ttttatgtta ttgctaatct attgaatgtt aataagaatt gtattatacc aaattaccaa      1380 tatgtgttt gatacttgta cttaaaacag aatgtggaat atcctttccc ttattaatga       1440
tattaaacat cattacaatt catagttata gcaatgaaat attatccata gaaaggttgt      1500
tgcataatgc atactagtaa agcatcaacc aacatatttt gaaaatattc ttaatcaaat      1560
aaaaaacata tattggaaat tctttaacag tagaaaaaaa catataataa tagagaatct     1620
taatcacatg tacaaagtcg tagttttgaa agtgtacatt gaaagagaca gttgtataac      1680
cctttgttgt ctaattatat aattaaccca ctatagttaa ataaatgata aacttggtta     1740
caactacatt aacaaaattg aaatgttgaa ttggtcagcc tttgacctta tactctttca     1800
ctaccaccac cccacttatc aattcactc tggccctata cttccttata ccaaagactt      1860
ttcttcaatt tgaaagtttt gtctctcttt taaaaagaaa taaaataatt atttatggtt     1920
tggtcatttg gtcaaatttt caaacactga aaatccaatg cctttatata ccaaaccaac    1980
actcatccat ttttatcacc                                                2000
```

<210> SEQ ID NO 9
<211> LENGTH: 2000
<212> TYPE: DNA
<213> ORGANISM: Arabidopsis thaliana

<400> SEQUENCE: 9

```
tttttattag attttgatca agttaaccgc taaaatctca ttttatccgt tcgcattaaa        60
gttaaataga ttgctgacat attttaaatc taatagaaaa tgccatctgg caaataaaca       120
acggacacga ttttaaacta aattttacca aaaagaaaaa acttatacga cttttcttgc      180
ttagaagtct ttgcattgtt aatagattgt tgaaaaggtt tattcattac tttcatgcag      240
agagataaca tatcatcgcg tggggattta ttcaatccaa agaaaagctt ccaaaaactg      300
actttgcttc atgaaacact cactctaatt tgcttcatca atcttaggac tgacttttcc      360
```

```
aaatcaatat gcgaactatc ttctaattta cattggtttc gtgttttttc gaaaggagac    420
aactatcttt ttaaaagctt ttctatagtg tgatgacaaa aaaaaaatgt aattgttagt    480
tgcaaaagaa aagtacaata gtcttttcta gttttgagag tttaaggttt atgatcggaa    540
cttagagttt aaatttaaac tattttgtta attttttggac tgataacagt tttttttttga   600
aaatattgaa acgttgttta cctaatgtaa catgttattc tacttaaatt actttatatt    660
ttaataacat ataatattga ataggatatc ataggatatt attacgtaat aatatcctat    720
ggtgtcattt tataagttag cacaagcttg ttttaactta taaaatgatt ctccctccat    780
ataaaaaagt ttgattttat agaatgttta taccgattaa aaaaataata atgcttagtt    840
ataaattact atttattcat gctaaactat ttctcgtaac tattaaccaa tagtaattca    900
tcaaatttta aaattctcaa ttaattgatt cttgaaattc ataacctttt aatattgatt    960
gataaaaata tacataaact caatcttttt aatacaaaaa aactttaaaa aatcaatttt   1020
tctgattcgg agggagtata tgttattgct tagaatcaca gattcatatc aggattggaa   1080
aattttaaag ccagtgcata tcagtagtca aaattggtaa atgatatacg aaggcggtac   1140
aaaattaggt atactgaaga tagaagaaca caaaagtaga tcggtcacct agagtttttc   1200
aatttaaact gcgtattagt gtttggaaaa aaaaaacaaa gtgtatacaa tgtcaatcgg   1260
tgatcttttt tttttttttt tttttttttt ttcttttttgg ataaatctca atgggtgatc    1320
tattgactgt ttctctacgt cactatttta cttacgtcat agatgtggcg gcatatattc    1380
ttcaggactt ttcagccata ggcaagagtg atagagatac tcatatgcat gaaacactaa   1440
gaaacaaata attcttgact ttttttctttt tatttgaaaa ttgactgtag atataaactt    1500
ttattttttc tgactgtaaa tataatctta attgccaaac tgtccgatac gattttttctg    1560
tattatttac aggaagatat cttcaaaaca ttttgaatga agtaatatat gaaattcaaa   1620
tttgaaatag aagacttaaa ttagaatcat gaagaaaaaa aaaacacaaa acaactgaat   1680
gacatgaaac aactatatac aatgtttctt aataaacttc atttagggta tacttacata   1740
tatactaaaa aaatatatca acaatggcaa agctaccgat acgaaacaat attaggaaaa   1800
atgtgtgtaa ggacaagatt gacaaaaaaa tagttacgaa acaacttct attcatttgg    1860
acaattgcaa tgaatattac taaaatactc acacatggac catgtattta caaaaacgtg   1920
agatctatag ttaacaaaaa aaaaagaaa aaaatagttt tcaaatctct atataagcga   1980
tgtttacgaa ccccaaaatc                                              2000
```

<210> SEQ ID NO 10
<211> LENGTH: 2000
<212> TYPE: DNA
<213> ORGANISM: Arabidopsis thaliana

<400> SEQUENCE: 10

```
ccattcacat tgacccaaat ccaccagcat ttcaaataaa gttacttaat ataattttg      60
tgtttataat atattccgcc cactcttgcc ttcatttgga ccttatccta aaagtcaaaa    120
caggtgaaaa aaatgagaat acaattaaca cgaaaaatgc aaaagactgt taaaccgaaa   180
tcgaattcta gtgtaatcaa tccttttccc aatgatacaa ctataaatca aaagaaaaa    240
atgtactgat aaacgaaact aaacgtataa attaatatat ttcttgacat aaataggagg   300
cttttgcctg ctagtctgct acgatggaag gaaaaatgca tgcacacatg acacatgcaa   360
aatgtttcaa tgaagacgca ttgcccaatt aaccaacaca ccacttcttc cattccaccc   420
```

-continued

| | |
|---|---|
| atattattta tttctaccat tttctttaat ttattgtttt ttctttgatt catacactgt | 480 |
| ttatgactat tacattttcc ctttcgacta atattaacgc gtttaaacca aagaatggat | 540 |
| ttgataatga aattttattt tattagcata tagataatgg atggcttcat gcttggtttc | 600 |
| catgacaagg aatgacacaa gataattatt ttgaataaaa tcataaatat gataatacta | 660 |
| gttgtaaaaa aacttgagtg tttcgtgtgt tattttttcgg tttcttgact ttttatattt | 720 |
| ctcgttttttg taattttagg atggattatt tagcttgctt ttctctttta ttactttcta | 780 |
| aaattttatt tataaactca tttttaatat attgacaatc aataaatgag ttatcttttta | 840 |
| attaataaaa aatttgtaaa ctcttgtaaa cagatcatag tcactaaaag ctattataag | 900 |
| ttatttgtag ctatattttt ttatttcatg aacttaggat aagatacgaa aatggaggtt | 960 |
| atatttacat aaatgtcacc acattgcctt tgtcatgcaa acggcgtgtt gcgtcactcg | 1020 |
| cctcctattg ggaatcttat aatcgcgtga atattattag agtttgcgat atttccacgt | 1080 |
| aatagttatc tttcacaaat tttatactca attacaaaat caacgaaaat gtacatttgt | 1140 |
| atctttaact atttacgttt tttttacgta tcaactttca gttatatgtt ttggataata | 1200 |
| tatttttta cttttgactt ttcagttttc acctaatgat tgggatatac atatgcatgc | 1260 |
| atagttccca ttatttaaat gtaagctaag tgcatatgaa ctgttagtca aaattacgaa | 1320 |
| gtttatttgt acatatatat agttataaca aaatggtaca gtaaattaaa cagaacatca | 1380 |
| agaaagtaca aaagactgaa cacaataatt tacatgaaaa caaaacactt aaaaaatcat | 1440 |
| ccgataaaat cgaaatgata tcccaaatga caaaataac aatatagaaa atacaaaaac | 1500 |
| aaaaacaaaa tatgaaagag tgttatggtg gggacgttaa ttgactcaat tacgttcata | 1560 |
| cattatacac acctactccc atcacaatga aacgctttac tccaaaaaaa aaaaaaaaac | 1620 |
| cactcttcaa aaaatctcgt agtctcacca accgcgaaat gcaactatcg tcagccacca | 1680 |
| gccacgacca cttttaccac cgtgacgttg acgaaaacca aagaaattca ccaccgtgtt | 1740 |
| aaaatcaaat taaaaataac tctcttttg cgacttaaac caaatccacg aattataatc | 1800 |
| tccaccacta aaatccatca ctcactctcc atctaacggt catcattaat tctcaaccaa | 1860 |
| ctccttcttt ctcactaatt ttcattttt ctataatctt tatatggaag aaaaaaagaa | 1920 |
| actagctatc tctatacgct tacctaccaa caaacactac caccttattt aaaccaccct | 1980 |
| tcattcatct aattttcctc | 2000 |

<210> SEQ ID NO 11
<211> LENGTH: 2000
<212> TYPE: DNA
<213> ORGANISM: Arabidopsis thaliana

<400> SEQUENCE: 11

| | |
|---|---|
| accatcgaac tctcctttag atattttcta tataaaacca aacaaaaaca aaaaaattgg | 60 |
| tccgatcatc taatatacaa gttagacgat ttcacgttat gttattacaa cctacaacaa | 120 |
| aatagactat gatcgaaatc atattgaatc tttttacctttt caacgtaata caaatctggc | 180 |
| tttacaaagc aataattcat gtttgtttgt ctaatttaaa tttccctgtt ttttttcccc | 240 |
| tctttctgtt tccatttga aagtaaaaga tcatttaagc acctaactca attttatttt | 300 |
| attttaaaca cctaatgtca tgctccttgg ctccttgtaa ttagttgatc gtttcaattt | 360 |
| agaccagcaa aacattttag tatgttcgta aatattgcgt acatgccatt tcgtttgtca | 420 |
| tgcaaacggt gtgtgtttct ttacttagct tctagttggt gtatattgcg tcgcattaat | 480 |
| atcggtttac cttcctcctg tctacgtaat gatatattct ccaccacaaa tttaaattct | 540 |

```
tattgaaatt tcctaatttt ttaggtagct caaggtctca agtatactac gtaccctatt      600
tttttgaata tctatctata ttataacaag agtttttctg agctagttaa tgagatgaca      660
atattctaca taaataaatg accctcgaaa gtttcaagta ctttaggatc tgaccaaatc      720
ggggtaaaac atttttgaaac taattacgtt cacatctacc atcgatgatt gacaagctta     780
ttgtcacctt ttatgttaaa gtgacatggt cttgacgtta atttgcatgt tattctacat     840
ctatagtcca aagatagcaa accaaagaaa aaaattgtca cagagggttc aatgttactt     900
agatagaaat ggttctttac aataataaat ttatgttcca ttcttcatgg accgatggta     960
tatatatgac tatatatatg ttacaagaaa acaaaaaact tatattttct aaatatgtct     1020
tcatccatgt cactagctca ttgtgtatac atttacttgc ttcttttgt tctatttcat      1080 ttcctctaac aaattattcc ttatattttg tgatgtactg aattattatg aaaaaaaacc     1140
tttacacttg atagagaagc atatttggaa acgtatataa tttgtttaat tggagtcacc     1200
aaaattatac aaatcttgta atatcattaa cataatagca aactaattaa atatatgttt     1260
tgaggtcaaa tgttcggttt agtgttgaaa ctgaaaaaaa ttattggtta ataaaatttc     1320
aaataaaagg acaggtcttt ctcaccaaaa caaatttcaa gtagataaa gaaaatata      1380 ataagataaa caattcatgc tggtttggtt cgacttcaac tagttagttg tataagaata     1440
tattttttta atacattttt ttagcaactt ttgttttttga tacatataaa caaatattca    1500
caataaaacc aaactacaaa tagcaactaa aataattttt tgaaaacgaa attagtgggg     1560
acgaccttga attgactgaa ctacattcct acgttccaca actactccca tttcattccc     1620
aaaccataat caatcactcg tataaacatt tttgtctcca aaaagtctca ccaaccgcaa     1680
aacgcttatt agttattacc ttctcaattc ctcagccacc agccacgact acctttttcga    1740 tgcttgaggt tgatatttga cggaacacac aaatttaacc aaaccaaacc aaaaccaaac     1800 gcgtttttaaa tctaaaaact aattgacaaa ctcttttttgc gactcaaacc aaattcacgt    1860
tttccattat ccaccattag atcaccaatc ttcatccaac ggtcatcatt aaactctcac     1920 ccaccccctca tacttcactt ttttttctcca aaaaatcaaa acttgtgttc tctcttctct   1980
cttctcttgt ccttacctaa                                                 2000
```

<210> SEQ ID NO 12
<211> LENGTH: 2000
<212> TYPE: DNA
<213> ORGANISM: Arabidopsis thaliana

<400> SEQUENCE: 12

```
tttgcataaa tagtctttta ctaattacta tgtaaataat tcctaagact ggtttcatgg      60
tacatattat cgttttatcc ttgttttaag aatattcaga tgtttggtct atggaatata     120
gtctattctt catgtttaaa actattattt gataagaaaa tatgtactaa tatgtttttg     180
catacaaatg ttgatcagtt cgtagcattt gaattaatac attctcaatc actttcaagc    240
attattatgt aataaatgat tcatgtcgaa aagtaatagt atcactgtcc attacatttg    300
gcatatatat ttttttgtca aagccttaca tttggcatat tgacgaagca gttttgtatt    360
cacttatatt ttgacatcgc tttcacaaaa ataaatagct atatatgatt attatccatt    420
aattgtctct tttcttttgc tgacacaatt ggttgtaaat gcaatgccaa tatccatagc    480
atttgtgtgg tgaatctttt tctaagccta atagtaaata aatctcaata caagaaccca    540
tttacgaaca aatcaaacca agttgtgatg ggttagtact tagtagcccg tttgaaatgt    600
```

```
agaattttg   atgagatttt   acgttttata   tagatttttc   tcagaaaaca   aaaaattctt    660
gcatcttgca   ttttggtcat   ttgtaaatat   ttttttagtc   ttaaaaaaga   cccaaattct    720
tattaatttc   aaaattttcg   gtctctaata   cctccggttt   taaaaaaaaa   catatcagtt    780
gaaggatgag   tttggtgaag   gctatattgt   ccattgattt   tggagatata   tgtattatgg    840
tcatgattat   tacgattttt   ataaaaaga    atattaaaaa   tggtggggtt   ggtgaagaaa    900
tgaagattta   tcgtcaaata   tttcaatttt   tacttggact   attgcttcgg   ttatatcgtc    960
aacatgggcc   cactcttcca   ccaaagccca   atcaatatat   ctctcgctat   cttcaccaac   1020
ccactcttct   tctcttacca   aacccatttc   ctttatttcc   aaccctaccc   ctttatttct   1080
caagctttac   acttttagcc   cataactttc   tttttatcca   aatggatttg   actggtctcc   1140
aaagttgaat   taaatggttg   tagaaataaa   ataaaattat   acgggttcaa   ttgttcaatt   1200
gttcatatac   cgttgacgtt   caattgttca   tatacgggtt   ccgtggtcgt   tggtaatata   1260
tatgtctttt   atggaaccaa   aatagaccaa   atcaacaaca   aatgaagaaa   ttgttagagt   1320
atgatacact   catatatacc   caaatatagc   atatatttat   aatataactt   ttggctatgt   1380
cattttacat   gatttttttg   gcttatctat   taaaagtatc   atacaaactg   tttttacttc   1440
tttttttct   tagaatatat   atgcccaaaa   tggaaaagaa   catatgccaa   ggttgatttt   1500
atcgcttata   tggtaaaaat   tggaaaaaca   tacaaatcat   tactttattt   aattaaatca   1560
tgtgaagaaa   catattcaat   tacggtaata   cgttatcaaa   acattttttt   ttacattaat   1620
tgttacattt   tttttttttg   caaatattct   taaataacca   ttctttttt    atttactata   1680
attaacataa   aaataaataa   aatataacat   ttcaacaaag   aaatttgctt   atgaaaaata   1740
caaaatccag   ttaattttc    agaaaaatac   aaatttgctt   ataaatatat   taccactagt   1800
ttatgtgatt   ttaaaagaaa   gaaatgcagc   ttaccaaacg   caacgtgaaa   atttgagaaa   1860
cccatactca   aaaaagatta   aatgacaaaa   tcaccctcag   caaaatcatg   aaacaacaac   1920
actaacattt   tcaccaaccc   caccgtctac   tccggtgaat   tgtctatatg   aactcctccg   1980
atacaactcc   tgtttccttc                                                      2000
```

```
<210> SEQ ID NO 13
<211> LENGTH: 2000
<212> TYPE: DNA
<213> ORGANISM: Arabidopsis thaliana

<400> SEQUENCE: 13
```

```
tcgtggtaat   ggtaggtgtg   tctctcttta   tattatttat   tactactcat   tgtaaatttc    60
ttttttctac   aatttgtttc   tgactccaaa   atacgtcaca   aatataatac   taggcaaata   120
attattttat   tataagtcaa   tagagtggtt   gttgtaaaat   tgattttttg   atattgaaag   180
agttcatgga   cggatgtgta   tgcgccaaat   ggtaagccct   tgtactgtgc   cgcgcgtata   240
ttttaaccac   cactagttgt   ttctcttttt   caaaaaacac   aaaaaaaaaa   taatttgttt   300
tcttaacggc   gtcaaatctg   acggcgtctc   aatacgttca   atttttttct   ttcttttcaca  360
tggtttctca   tagctttgca   ttgaccatag   gtaaagggat   aaggataatg   gttttttctc   420
ttgtttgttt   tatccttatt   attcaaaaag   gataaaaaaa   cagtgatatt   tagatttctt   480
tgattaaaaa   agtcattgaa   attcatattt   gattttttgc   taaatgtcaa   cacagagaca   540
caaacgtaat   gcactgtcgc   caatattcat   ggatcatgac   aataaatatc   actagaataa   600
ttaaaaatca   gtagaatgca   aacaaagcat   tttctaagta   aaacagtctt   ttatattcac   660
gtaattggaa   tttccttttt   tttttttgt   cgtaattgga   atttccttta   tcaaacccaa   720
```

```
agtccaaaac aatcggcaat gttttgcaaa atgttcaaaa ctattggcgg gttggtctat        780
ccgaattgaa gatcttttct ccatatgata gaccaacgaa attcggcata cgtgtttttt        840
tttttgtttt gaaaacccct taaacaacct taattcaaaa tactaatgta actttattga        900
acgtgcatct aaaaattttg aactttgctt ttgagaaata atcaatgtac caataaagaa        960
gatgtagtac atacattata attaaataca aaaaggaat caccatatag tacatggtag        1020
acaatgaaaa actttaaaac atatacaatc aataatactc tttgtgcata actttttttg        1080
tcgtctcgag tttatatttg agtacttata caaactatta gattacaaac tgtgctcaga        1140
tacattaagt taatcttata tacaagagca ctcgagtgtt gtccttaagt taatcttaag        1200
atatcttgag gtaaatagaa atagttgact cgttttatc ttcttctttt tttaccatga         1260
gcaaaaaaga tgaaataagt tcaaaacgtg acgaatctat atgttactac ttagtatgtg        1320
tcaatcatta aatcgggaaa acttcatcat ttcaggagta ttacaaaact cctaagagtg        1380
agaacgacta catagtacat attttgataa aagacttgaa aacttgctaa aacgaatttg        1440
cgaaaatata atcatacaag tgccagtgat tttgatcgaa ttattcatag ctttgtagga        1500
tgaacttaat taaataatat ctcacaaaag tattgacagt aacctagtac tatactatct        1560
atgttagaat atgattatga tataatttat ccctcactt attcatatga ttttttgaagc        1620 aactactttc gttttttttaa catttttcttt tgttggttat tgttaatgag catatttagt        1680
cgtttcttaa ttccactgaa atagaaaata caaagagaac tttagttaat agatatgaac        1740
ataatctcac atcctcctcc taccttcacc aaacacttt acatacactt tgtggtcttt         1800
ctttacctac caccatcaac aacaacacca agccccactc acacacacgc aatcacgtta        1860 aattaacgc cgtttattat ctcatcattc accaactccc acgtacctaa cgccgtttac         1920
cttttgccgt tggtcctcat ttctcaaacc aaccaaacct ctccctctta taaaaatcctc       1980 tctcccttct ttatttcttc                                                    2000
```

<210> SEQ ID NO 14
<211> LENGTH: 2100
<212> TYPE: DNA
<213> ORGANISM: Arabidopsis thaliana

<400> SEQUENCE: 14

```
ggcaaagact tgaaggcatc atctgtgaag gcaagttcgg aactgacaac taattcatcg         60
aaatccttga agttcatctc tttactgaac ataccgtaac agatttctgg ttcaatggct        120
ttttgaagac aaaggaagat atcaaaaaca tcagagatat ccacatccag gatctggaat        180
tcctcataag ttactggtac agccacctt ccctgaaatt cctcagcatt tgatatttcc         240
aggatagtca ctatatccat ttcagaaaat tcatcctctg gtaccacatc agattggcca        300
ctcttgttca aatagcaatc cgtagagagt acatccaata gatcataatc ctttgagcct        360
ataagctcct tagaattgat aatgagagaa ctccctgcat tagtgtcttg gggttcaatc        420
gtctcaagaa cagtaaatac tttatcaagc acagataagc ttgatagttc gctcaagttt        480
acttcatcca cttctagaag gggaaatctg gcatctttga accatggttg aatcttgcgg        540
aagcattcat tttctgctac agaagtgttg ttctctgtaa agtaatcaga aggaatgtaa        600
tcaacagaat aaatctgctc ttgaatgtcc tttgagttct gcaggataat atctgacccc        660
tcatatttaa cctgcaataa gaagactagc taaaatcaga tgatgccaag aacaggaacc        720
agctctacca ctctacagca aaagcaaaaa ctactgttgt gtgtgccaac taaaatcaac        780
```

-continued

```
tcagggattt accgggtcat ttttgatctc tagaacttca gagaaacatt ggagatgatc      840
ctcactcgtg cataagagct tgttctcctg tatatcaaaa gatgctttat ctcgcaatga      900
aaagaaaaa gctgaactag ttcaattagt acaatgctta cacagcttga gcaataccat       960
ctcaaaatcc aactctggag tctccaactc aataatttta ggtgtagctt tatccgcaat     1020
ggcatctccg tcatccttct gcaaatagat cataacttcg gttttcaaac tccggtaaga     1080
ttcgcttaag ctaccaaaat ttccaaccca agtatgaata aagatctaa gcaacaatca      1140
gaaatggaaa ctgagaaaac acaccacaaa tttcgaaaaa tctacaacca atctcactat     1200
aagaaacaaa ggaccgttga cagaaacagt cagcgagact caggaaattc gaaatttcac     1260
ctccaggaac tgataatatc tagatcgaag gaactttacc tcgtctgagt aataaactcc     1320
gagcgaagag tcgtcgattt caaaaactcg atagtccaca ctgacgcggt cgggaaccac     1380
gtcggaaagg aacttcgaca aagcagcttc aataggcaaa tttccgatag ggatactaac     1440
attttcgatc gagccaaatc ggagacggtc ttcttctccg ttgtagacga tgggtgccgg     1500
gaaattatca ggagccggaa gattgaggaa gcctagggtt tcaaatacgt gagaaggtgg     1560
agtagagaag taatcgatgt tgagaaatcg agttcgcatc gtaattttct agatccgtct     1620
tgggagctca gactgtatca gtgatgatga tgatgatgaa gaagagaacg aattttgaaa     1680
ttggcggttt tgaattttta agaaattaaa aaatatcccc cgtcgatttc aagagggaga     1740
tggagatacc aaagcaactc tcgccacttg tcgtcttttta attttaattg agtacgttat     1800
gccgttttaa atgttcaaaa cagcacacag ttgatagctg aattgatttt ttcttttgcc     1860
gttttgttat atttaaacaa cacacagtgc atttgccaaa taactacatg atgggccaat     1920
aaacgtggac cgactaaaac taaataatag aagatacatc gataggcttc tctaaagatc     1980
ggataaaaga taatgtcgca tagccacgta gagagcaact ggctgagacg tggcaggacg     2040
aaacggacgc atcgtacgtg tcagaatcct acagaagtaa agagacagaa gccagagaga     2100
```

<210> SEQ ID NO 15
<211> LENGTH: 2000
<212> TYPE: DNA
<213> ORGANISM: Arabidopsis thaliana

<400> SEQUENCE: 15

```
tcgtcgtgga gaaatcgtcc ttggcaccta gatcttgaaa cccgacaagc ctatccatcg       60
cgattccctt gctgaagaat aatgatttca acattcgtgt tttcgttagt ttaaacacat      120
aaagacctaa ctgcgctaag aaataatgag tgaaaaatgt aggagtgacc taaaaaggat      180
aacacacggc aaagtcttga ttgcaagctt ggtgacgaag aagggagcgt tctacatgaa      240
gtgtctccca agtattagaa gatggcaaaa tggagtttca agaagagtt aaggaagtgg       300
attactgacc tcagcgtcca tcttaatgaa ctttgtgtcc acatgtctag gagcaagggt      360
cttcaaatgc ttgtccatta tcctagaatg ttcaaacgca taagcttcaa attctgaata      420
ttcacatatc aaaaaagtga tgcgagggag agaagggtat ttcatcttac ttgcagcgat      480
agaactcctt gtggtagaag tgacatataa cttttttcact ccttgtgact tctcccaaga     540
agtcgccttc gctaacttct cggtattcac catgtccttg tcttttgaat gcttctctct      600
tttccacttc tctctgtcca gacacatctt gggattagat catagtccat actaatgaag      660
acaaagtgt taaccaaata tagataatga gagaatgtgg ggggtgaagt tgaaccctga      720
gtgctgcaat cctatctgcg tgcaacttttt ctagctctgg atcctacaga acaagagcaa     780
gtcagtctcc catagagaca gaagagaaac ataacatttc attgtacaga ttataaaaga    840
```

```
acaattcaaa gagagccccc attgaactta catccatcaa ttcgtcaaga tcaacttcct    900
cgttgacagg tcttgatcct tgtgcctttt catttgcaag aacttcctgc acaacaaaaa    960
tacggaaatg tttttgatcc aagaacatca aactctaatt gcaattgtaa ccaacaaaaa   1020
aacacttaaa attcgctata cactatcaaa tttcctgaca cgtagacctc atgtcagcac   1080
aaatagaatc tagcctatct ctgttaattg ggttaccaaa caacatgaga ttgattatgt   1140
ggaaaaccaa gcacattatt tacccttga aaatacgcga atcaagatc caagaagaat    1200
ttatggagaa cagcttcgaa gtacgaaata acaatgaag attaaattac cttttatatt    1260
tctctagcag ctgccgccaa tacattcccg aatgccagat cgagagggt cgacttcacc    1320
gtatccggat ccatctcttt accaaccaac taatccaact cagaaaattt taaaatctca   1380
atcaaaaatc cctctaagat agccagagaa gagattgtaa acaaggattt gaatctggt    1440
gcagagagga gaaactcccc gacaatgaac accaacgatc taaacgcggc gtttggtaaa   1500
agttgagtaa attttgttag ggcttagttt tagtccatgg gctaattagt aagtgattta   1560
cggcccacac atgagcccaa atgtttcaga cccagccaag tttcttcaaa ttcacccaat   1620
caacgacgat gtacgtgtgt atgaaaatca ttaaacgac gcatcgcttt cgaggaggag    1680
cattacgtgt cctgttagct acgataatgt tagtaccgcc acaaagaaaa ggatagatat   1740
tttgctttcc agcaccctgt catgggattg atatgaacac gtacttggta tcgacatgaa   1800
agctcaaaaa taaattcaat ccgattcctt tagtgatatc agaagttcat tttaaatacg   1860
aacacgtatg gcgaaacacc acgccgacat tttctgctgc tgccacgcgt cactttccaa   1920
atattgattc attaaactaa tagttgatcc atatccgaaa ccggactata aaactatctt   1980
caatgcgtta acgaatcttc                                              2000

<210> SEQ ID NO 16
<211> LENGTH: 2000
<212> TYPE: DNA
<213> ORGANISM: Arabidopsis thaliana

<400> SEQUENCE: 16
tttacgtacc aatcaaaatc gcatctttct tttcaaatat aattatgtat atatacgcat     60
gtgcagctgc tgcgtgtcta tgcatacttg agtctaaata actatccctg actatgatat    120
gtcgttggtt acgaatgtga tctttagtta aaataacaag aataatatca cacagacaaa    180
aacaaataag tgcatattat ttcaacaaga ttggagtggg tgggcctaaa ggcttaaaaa    240
aatagagcac atgcacagag gaccattgat tccccagaga caatcagaca tctgagaccc    300
taatcgcatc aagccgcgtg cccttcttcc attaactaat tttgtgtgtt tgttttggct    360
taaacctgag aattacattg attactttat ttgtttcatt ttctccatga aggagataaa    420
aagagtaaaa attagagatt gatgaaaact gaaaagaaa ctgaagtcgg taagataggt     480
gttggaactt ggaataatgg cttggctttg aacaaaacgc atgcaccatt cattgccttc    540
aagttttttg caattagctt tgttttttgtt tttgttttg ttttgggag aggttctaat     600
gaccaagaat caagagcgtt gtctaaaatc taaaccatat gatacggttt ttaatattct    660
catgcattaa aatgtactat ttctatatat gatcttatat acccaacatc ttggaattaa    720
tagtttgatt cgttatcatt tgaagaagct ctcaacagct tcaaaaagcg aaatgtagca    780
tcatgaagcg gtatccaatt tcaagaagct accagtagct tgtggaagtt tcaagaagt    840
tttccggaag atccaacgat tgtggaagcc cctcatagtt tttggaagtt ttcaatgata    900
```

```
ttagcagcgt tgagcgtggc atggctagac aatgtaagag atttgatttg caacacattt    960
gatgtatttt tttacttttg agttacaatt gtaatgtatt attgatttg cccagttatg   1020
atttataaac cctacaattt agtatcaaag tttttattta aaattctgaa tctgacatta   1080
atgatatctg gctcatttac agagccaatg agatggatga tgttcgaaac tggattggcc   1140
attatttatc ttttttttat ctggagaatc tcgaggttgg cacaaacatt atcatattag   1200
cctttagaaa ttggattggc taatcacaca tttatatata ttcttaccaa aataaatcac   1260
ctctcccgta attgaaaaat atctaaatac tgtaagtctg aaaaaattca caagggttcg   1320
aagaaagaag gaaatatcta agcatcatta ataaactatc tgtaacctga gggaaaatca   1380
tttcatgttg aaatatgtgg atttggaagt tttataatct atctgaattt gtgaaatttg   1440
ataacaagta agatttgttt cttaacacaa atctaaaatt tgttttctaa ttaggtttga   1500
gagagagaga gaaagaaacg ctttgtatga tacacatcta ggctatgaat gaaggcagcg   1560
gacaaagcgg tctaatttgt ctgcggttta gtccatctca ttttgggt ggacaataaa   1620
ccgctgcgga ccaagtttat ttgtatgtaa aaacggtccg cagatggtcc gcaacgattt   1680
tcttctatt ttttaagtcc agaccactgc ggactataat tgatgaatga taaataaaaa   1740
acggtctgat ccgttgacgg ttttgtccgc cccaaccgcc ataaccattc aaaccccctaa  1800
ttatttcatc agataacatt atacactaat aatcattgca ctcaaatatg tcacacaatc   1860
atataataaa ataataacaa tgattaaaat gaaaaaattg ttgtggcgcc gcataaaata   1920
gaaatcgtga gagacgacgt catctaaaaa ttgccttgct gtccacttt cactttgtcc    1980
tctcttctca tctccgttca                                              2000

<210> SEQ ID NO 17
<211> LENGTH: 2000
<212> TYPE: DNA
<213> ORGANISM: Arabidopsis thaliana

<400> SEQUENCE: 17
cgtcaagcaa catcgtacaa gattgataaa tgtctcacat gtgtagtact taatagtcac     60
aatttgacta cacaaacctc taccgacact aatgtagcaa ttatatcatg ttatatgctc   120
ttaaggtata gtatgtataa caacatttca ttctgtaaaa tatcatcatt tatatcaaat    180
ttatgatata taaatatca ttatcatttt aaataacac taaataatc agtgcaattc     240
cgtataatct tcatatgaaa ctgcaagaat ccttggtgtt ccaaagatta tgatgattat    300
tgtgagcttt gatttatggt ttccatcttg tcaaaaaatg gcttttataa atggtagagc    360
tttcttagtt ttccttaaga tatacacaac aggttacaaa tataatttat ttttgctaaa   420
agaaatagtt atagtaaact tgtaaaaact actacaacta ttttatggaa aatgtcttaa    480
agctgtttca acttttatac acattactgc atttactatt ctgaaatcaa ttttttaatta   540
aggtccttgt actataagga atcctttaaa taaatataaa tattaacaat aaaaaaatcc    600
aaaatttcag aatgcaatgg tcttacaatt acaataataa tgtatttgat tgtactaaaa   660
atataccta aatactcacc aattatcttt tataatataa tccacaaatt tctggaagag    720
gaaaaacaag taaatgcaag tcacatttca catttcaaat taccaactac caactacaaa   780
ctacttccgc gtctcaaatt gaaccactaa ttaatcacta ctttatatgc tcatcattct    840
tttctttca ttacaattct agaataatga cttaaccaaa attcatacaa ataaaacaat    900
attttggctt cctccaccag gctaagaatt ttggtattga aaatctaagt acttcataag    960
aaactgttgg aatcatttaa aatttgtgat catatataaa aaaatttatt catctttata  1020
```

```
tttaagagtt taaaaactgc aactttgtt tttctttcac taagtcttat ggccacagtt    1080
aattaaaagc agatgaaagg tggtccaatg gaaaaggaga atgtgattgg gctagttggg    1140
agagttctga tgtctagtgt tgggtacacg tgtccgtcag ttacacatag cattaaatca    1200
gacggcatgt cattattcaa atctagttca catagtacga ctaatagctg ataaattaat    1260
gattatacag catatgaatt atgaattcaa aaaaaaaaaa aaattgaaaa tgttaaggag    1320
atgctatatt ttacaaaatt catcgcaatg ctttctacta atttgctaag tggtcttctc    1380
cagttagtct tgtcgattcc aagcgatatt attaaatctt gaagcatcgc tcaaagcatt    1440
atagcttaag ataaccaaat tgttattaaa acacctagt gaaatttta aattaaaaca     1500 attttgatat ctttgtaata tctaatacta ctctttctgt gtctaaaagg attaattttc    1560
aaaaatttca cacatattaa aaaaaaaaaa aaattactag ctaaacaatt ttcaataatc    1620
ataaaacaat agtaacttaa taattttttt ttattttcaa aatagtcctt caagtttaca    1680
attcatttta gtattataat caacaaaatt tgtattaaaa agttggaaaa ttaatctttg    1740
tggaacaaaa aaatctagaa atcattttt agaattagag agaggtttga taaaaaaaaa     1800
taaaaaaaaa tagagagagg tagtacatac taaacgatgt gatactacta ttgacaaaat    1860
cttaattctc agtttagtag aataaactag aaggaatgaa tgaagtaaat gcgaatccaa    1920
ctactaacaa accctactta gtcatcatat tttcccatat gaaatcccta tataaaccca    1980
tcatcatctc ccactttttt                                                 2000

<210> SEQ ID NO 18
<211> LENGTH: 2000
<212> TYPE: DNA
<213> ORGANISM: Arabidopsis thaliana

<400> SEQUENCE: 18
attttggtta agtcattatt ctagaattgt aatgaaagaa aaagaatgat gagcatataa      60
agtagtgatt aattagtggt tcaatttgag acgcggaagt agtttgtagt tggtagttgg     120
taatttgaaa tgtgaaatgt gacttgcatt tacttgtttt tcctcttcca gaaatttgtg     180
gattatatta taaagataa ttggtgagta tttaaggtat attttagta caatcaaata      240 cattattatt gtaattgtaa gaccattgca ttctgaaatt ttggattttt ttattgttaa     300
tatttatatt tatttaaagg attccttata gtacaaggac cttaattaaa aattgatttc     360
agaatagtaa atgcagtaat gtgtataaaa gttgaaacag ctttaagaca ttttccataa     420
aatagttgta gtagttttta caagtttact ataactattt cttttagcaa aaataaatta     480
tatttgtaac ctgttgtgta tatcttaagg aaaactaaga aagctctacc atttataaaa     540
gccatttttt gacaagatgg aaaccataaa tcaaagctca caataatcat cataatcttt     600
ggaacaccaa ggattcttgc agtttcatat gaagattata cggaattgca ctgattattt     660
tagtgttatt ttaaaatgat aatgatatt tatatatcat aaatttgata taaatgatga     720
tattttacag aatgaaatgt tgttatacat actatacctt aagagcatat aacatgatat     780
aattgctaca ttagtgtcgg tagaggtttg tgtagtcaaa ttgtgactat taagtactac     840
acatgtgaga cattatcaa tcttgtacga tgttgcttga cggttttgg ctgatagtat      900 ccaacaccat acatcaacct ttcacgtccc aagctctcta agacatcgga gaagcatcat     960
cacatgcgta cgtagaaagg aaacacaaaa gttaaagaca ttttgtaata tgtgtaacta    1020
tgagacatat atgagactgc atgtgactat gagttatata tggcttatag agcgatagtg    1080
```

| | |
|---|---|
| ttatggagat tatattgcat tcatgctatg tactgcataa gacgaattcg gtttcgtgta | 1140 |
| tttattcccg cttgagtcta gaattggttt caagtatagt tagaaaaaga ctgtttttt | 1200 |
| cgtcctatta tggttcgtat acaaaattat gcattgaatt gatgtggcat tcacgtaaaa | 1260 |
| atcttcctgc agggctataa aacgtatttt tggcgtacga ttataataaa ttttgttatt | 1320 |
| attcagatta tttattaaat cttttttgtt gttgacaaac gcatttatgt taatgattat | 1380 |
| acgaaatatc gagaaaaact ccatatagca cctctatcat tcaattatgt agtaagtcat | 1440 |
| aaaatgtgaa ctttgctaat tataatggcc ataattagta aacgtgatgg gagaattgtg | 1500 |
| atgtttagtg ttggatacac gtgtctatca gctgcacatc gcatttaatt ggacggtatt | 1560 |
| acatatatag tacacataat agctgacatt tcatctacaa cgaagataca aattttaaa | 1620 |
| cgattttctc ttgtctacta cagtataaca tcgctctaaa catgctaatt aaaaaaacaa | 1680 |
| gtttaattaa ctgcagataa atgaatatat attttttaac agtatagctg tatatatatt | 1740 |
| gacgtattgg tctttgtaca ttctgaaaac tgatactatt gtttacataa ttacatatga | 1800 |
| ctggagaaac taattatttt ggttagtaga agaaacataa ctacatatga ctggagaaac | 1860 |
| taattatttt cgttagtaga agaaactaga agaatgcat gaagtaaatg caaaaccaac | 1920 |
| tactaacaaa ccctacttag tcatcatttt tcccccatac gaaatcccta tataaaccca | 1980 |
| tcatcatctc ccactttct | 2000 |

<210> SEQ ID NO 19
<211> LENGTH: 2000
<212> TYPE: DNA
<213> ORGANISM: Arabidopsis thaliana

<400> SEQUENCE: 19

| | |
|---|---|
| catgagatta acgattgtga catatactag acacagtagg agtgtaggac tacataatga | 60 |
| aggtagtact caaaccttac aaaaccagcc tatgaagaaa gaagccttat gagtattaga | 120 |
| gtacaggatt gctacggct tatgtctttc tgatcaccct tttttaactc atgctcacca | 180 |
| taagcggcta ttgatgtttc agttccttta cttgttatct ctgcacgcta atctcatgaa | 240 |
| aaaaaaaaac atgtatcata ggacagtagg actataatct tgcataacca ttaaggggta | 300 |
| gtatgactac aaacatttta gaaaccagct tattaaggaa gaaggcttct ctgtaattga | 360 |
| gtattaaggg aacattaaaa cgtttggttt acgttaaaaa taattaagct atttgtgtgg | 420 |
| tgtgtagcat tgtaacttat gagctataaa ctaattttct caagcagaat gattactttg | 480 |
| gttaatcttc attttaggat ttgctggatc tgtgtcccga gaaagtcagc aactacgaag | 540 |
| aaaagctgaa gaacttttc acagaacaca ttcacaagga cgaagagatt cggtactgcc | 600 |
| tagcaggaag tggctacttt gatgttaggg acaaggatga tcgttggatc cgtatctgga | 660 |
| tgcaacctgg cgatctcatt gtccttcctg ccggaatcta ccaccggttc acactcgacg | 720 |
| ccagcaacta catcaaggta caaaaagcca aactcagtct ctatactaat ttactaattt | 780 |
| atatgaatac gcaaatgaaa tattacatct taatatctta tgttaaaaga tttgattgtt | 840 |
| ggtttgtgat gtatggtggt ttggttttgc agctaatgag gctgttcgtg ggggaaccgg | 900 |
| tttggacacc atataaccgg ccacaggaag aacatcctgt taggaaaaag tatatccacg | 960 |
| gcttaaccta caagtttgga gaaaccgtta agcacattaa caatattaa tatatgcttg | 1020 |
| ttgtgtaatt tgtatgtatt gtttactctt tagtcttaag cagtaaaata aaaacagcgg | 1080 |
| ctccttctgg atagttgttc ttgtaacata cttttgcgat gtatgctttt atacataaaa | 1140 |
| aaaatagtgt gtatttatct aataagtatc attaaaaaac aaatgtcagc tgcgaacgtg | 1200 |

```
aaatttataa ctaaaaaaac cctacgattt tcgaataaat tatttgagct ttccaaactg    1260
taattcaagt attattactt atatagtgtt agtgtacttc aaaagttaaa gcataaattt    1320
tcttatattt gaaatgacct cttctttaca aaatcttctt aaaattatgc attatcaata    1380
tattaattgt atatatatat ataatgtata attctgcttg tgtcgtgctt aaccgtttga    1440
tttggtgtgg ttagatctgg ttttccccca acccaattca attgaatcaa ggatcaatca    1500
aattttcaaa ggatactctt gttctctaca caaatctttc aaagggttcc accaaaaatc    1560
ccatcattct gacttcagaa taaacaaaca aaccacgaaa cgtatctcta tgcattcact    1620
acaacgtgtc atgggcgaaa acgaagctta taaatgttgg agcatagtca ctaaattat     1680 aatgattaat taaattttag attttctgat attcatagaa gacaaaagaa cacaaaagta    1740
gcatcttcca atgaatgtat gacactatga tctctcattt ccatttatag caaatcggct    1800
ttgtccacat caaagataac taataaatag acttatccaa aacactcaaa agcaatacat    1860
ttctatccaa aaatattaaa ccccaaaaat atagacagca taaagcatc ctcaagcttc      1920 agctattcat cacaactatt ctctcctctc tcttttttta ttaaaaaagc tcaaatttat    1980
ataggttttt tgttcacaaa                                                2000

<210> SEQ ID NO 20
<211> LENGTH: 2000
<212> TYPE: DNA
<213> ORGANISM: Arabidopsis thaliana

<400> SEQUENCE: 20
atgcatatga tatgactgaa ttatttatta ttcgcctcca caagttacag gactataaat      60
tattcatctc cagaagttgc gttgcaccac taaatatgaa gagaagataa aaccgaacag     120
gtaaaaggga cgtttaccaa aatatcaacc taatcttccc ctaaaccaaa ttttttccaat    180 taagtttatt cttaagcaca atcaactctc tgttactttta aagtattctc gtgaccactg    240 attgttttc ctggtgtata agtaagtacc acaaaatata agaacatgac ataagactct      300
ataaaatatg tataactaaa cattttttcat ttgtagccag ataaaagaaa tctatgggcc    360
ggaagtcgta ttatttgaca cggcactttt ggttaacgta taaactatct gattttataa    420
gctgtcaaaa caaaaaaatg gtaaatttaa cattcataaa atatcatgat gttccacagg    480
tcacatcagt gaaagactaa actttctgat tttttgtaaa attgactatg aggacatgca    540
tgaattaata ttctacgacc acaattactt ctctaatctg gattgaaaaa tggccaccgt    600
atacatttct ttaaataacg ttttttcaaat tttattataa aatctagggg actaccatat    660
tatatgtata aacgtccata tccatcttag aaatgttatc aataataggt ctgaaaaatt    720
tcatagaacc acacttattt tggagctgaa ttcaatcccc caacgtactt tctcgttctt    780
gttatgtttc gttgtcgctt tgtttatatt tcttcttatt ttaggggttt tttcagttcg    840
attttgtttt gttttttagtt agcggacgaa aatatacaga tggtagtact aacttttctc    900
ctagcattct catctatgtg tgtgtgttat acatttatat cggtgctctt ggttgacctt    960
agaaggtact ttatatatgg ttcgagggtc catatggata agttcagatt aaacatctaa    1020
aagtgcatct tgtgaccaaa aaaaaaaaac tatccatatt taaatgcaaa aagatctttg    1080
gatgaattat tatgacacaa gcaatcgcga tagaatagga aaataataaa atgcatgcat    1140
cctcagcatt ggttgctaaa tttccagttc gattttcaat ttcgaaaggt gggctccatt    1200
tgtttactag atgtgttttt ttcttctctt ttgttgtgaa tgtttactag atatgttat    1260
```

| | |
|---|---|
| tttcaattat tgtatacgt gtgggtcgca aatgccgctt gcgtggtaca caaataata | 1320 |
| tcaatccttt gagaaaatta aaagtcaaag tgcataataa tatactcagt atgtttttt | 1380 |
| cctttgcaga tattccatgc atatgctaaa taacatcatt tatatatcat taaaaatgta | 1440 |
| caacaagaaa ccaaatgcat atgctaaacc aatccatata atatgttttg caggttcatt | 1500 |
| taaatcgact aattatatta tggttttttt tttttgcttc tgatattgca tctaaattgt | 1560 |
| tgttgaactc ttttccgcca atagaaacaa tatttcaaat tgtagcatc gctaaataaa | 1620 |
| atacataata agttgaaaca atatagttgt tgagtaaatt atataatcat ctttgctatt | 1680 |
| gttaattcta aatttattta acacaaaaag ctaaccatta agcaaagaag aaagtgacat | 1740 |
| gatgatcgaa aggaacatta gaaacgtcct cattgtccgc cgggaaatat tttggagaag | 1800 |
| gacatcgatt aatctataga ttagaggaca cctcttagtt taaataatga tatcgttata | 1860 |
| cacctaatga aattaaataa atgctcaatt catcaataaa taatttaatg tgtgtttcct | 1920 |
| aatactcgga acattataac caccaatcac cacctccaaa cttccctata taagacacga | 1980 |
| cacccattct aagcatcact | 2000 |

<210> SEQ ID NO 21
<211> LENGTH: 5000
<212> TYPE: DNA
<213> ORGANISM: Arabidopsis thaliana

<400> SEQUENCE: 21

| | |
|---|---|
| aactattcac actctatata tttataggat tgaaatatct gaagagctca acacatttat | 60 |
| atcaaacata tattttgttc atttactaaa cactagtaat gctgttctag ccttacctat | 120 |
| taaatcgtat cccaaaacag aagtgatgtt tttcgaaaca ttattgcgtt tttaaaagat | 180 |
| aagtgaaata ttgtgtccaa ttggtaacac aacaaagttg taaactgtaa tgataaattg | 240 |
| ttacgaaata gtataaaacg gtaaaaaacc tcgtacctct agaatgataa ttgtaattgt | 300 |
| taattatcaa aacggtatac ctcgtaccac aacagtacgt agttatcgtt caaaaccatt | 360 |
| tatttttgt tataagtaag gaaaaaaata tcaacgtggt ttagtctcac attcgatgtg | 420 |
| attgatatac aaattttttt tcttttccg agttctcttt gattttaaa aacgttgtat | 480 |
| agctgatttt ccctaccgaa taatcttgag gtaagctctt accattagaa aattagtact | 540 |
| gttaatctct cttatcgatg gtgacaaaaa aattagcacg tgataggttg gtttcatact | 600 |
| tccatcgttg tctatcacca tgtattgtta tctttaattt atttggaaac atattaaaga | 660 |
| ttatggcgac ataaatattg ctcacggtga tggtattatt tattttctta tagtatgtat | 720 |
| gtgaagaaga gaaatgattc attcaggtac tctcaagtcc catttgagtt gccctacaat | 780 |
| gtgtacccac aagaactgaa ataaccctca catttgtttg gttgttgta attttctcca | 840 |
| tattcatgca tgtactcgat caaatcgata tgattatatc aatctttaac gggtgggcgg | 900 |
| atttcgtctt ataaaattaa ctggcctata ataaaatgag gtagttatac ttatatcaaa | 960 |
| atcaaaatga tggaaaattt tggattaatt aacatttttcc tcgaccaaaa acgtgaataa | 1020 |
| attcaataga atatattgat ccaaaggaaa ctacaggagt aactaatcct attttaaggt | 1080 |
| ttttacaatt caaatcaatt ttccctgatt tgacagaacc aaactgaaat cataccaaag | 1140 |
| tggattcagt tgacctggta gttaatttct ttcatttcaa gttagattca ttttagggaa | 1200 |
| acattttgt cttgcatcat gatgtcttct accattagca atggttgcct tgatgatttg | 1260 |
| gtgcaagaag gtggtgtgct tccatatttt tttaatcctt ttttggcatg tgatgcttaa | 1320 |
| ttgtgtaaca acttttcatt gtaaaatgaa gatttacatt cttataaaaa aaagagtta | 1380 |

```
gatttgaata tgctaatcac tcaaccctaa ttaatcaaag gtataaaaat ctttctttt    1440 atgtgaacaa gatctgagag acataaaaaa tccaatggaa agaaaaacat ggtgcatgga    1500
tatgtgtcag ctcaacatct tttgtgaacc ccttttacaa aaaagtttga ttcagccata    1560
ctatttattt tctatgatcc ttcttgcact ccttcattct tctccagtca tatgaaactt    1620
ggacccatca atttttttt cttcattatt tcccttttaa agatatgatt aaagcagcat    1680
gcatgtggcc atgctcttaa ataattccca ctgaaaatga cattatatcg acccgatgcc    1740
taacattatt ggtactattt tttcgagatt tcaaatggaa tgtggttaaa agaaattgat    1800
tatgtggtaa atttcatagt ttttccaccat ttttatctgt atgtataaaa cttattttca    1860
atgtgttaac catgtgtggt aacttattgt ttattttttg tcaaagtatt aacatatttg    1920
ccatgacttt tttgttgatt agaggataaa ctatcaagag ggtaataaaa actggtatgt    1980
gcgttgcaaa ctatagagcc aagttgtgag ataggtcttc tggatgagat cagagtgttt    2040
cgatgcctat gtcttcgtct tcaagagttg atcgggtggc cgttccgacc tactgtactg    2100
tcatgatacg aggtatattt ttgttatata taaaaacaac gataaccttt agaagtcatt    2160
aaaagaacaa tgactaatag gtctttattt tgttgggctt acttaatttt gagttgtgac    2220
aactatactt tccagcccat ttgttttttc attagaaaaa tgttttgcta ctttgcattt    2280
tacaaaccca caatgaaaaa gaaggtagct ggatcatgtg ttttttttc tacaagtctg    2340 ttgaaaggtg gttcaaggaa accgtagtcc actaactatc cttagttagt tttgagttca    2400
ctcaacctga gtcttcattt gcaaaaattg actatcaata accgactccg attataacaa    2460
agttcaagca tttcaaatgg ccttattgaa agggcgaaac aatttcctgt catcctggtc    2520
taataaaatc cttaattata taaccaaaaa gcgatatatt gtctcaatgt tgttgctaat    2580
tattttcttt ctaggatgta gcctgtcctt ttgtatagat aaatgtggtt aagaaattta    2640
agttggggag gtcatctatt agttaagtag gaaaaatgta agatcacgag caagcacgat    2700 ggatctttt tttccttatt tggaaaaatc aggacgtcaa agtatatat ttgactaaag    2760 ctggaagcac gaatccaaag ataaatatct tgaattgaaa agtcctgaag aagttaatat    2820
aaagataagt tttaaagttc tgtaggatta ttgaaaatgg ggaattttgt tgaagtcgtc    2880
gtcagattaa agaagacatg gaagctacgt tccaactact tggtttaatt agctaataaa    2940
taaaattatt aaaaaaatgt atcaccatta ttgtcatgta agtcatgttc acattcactt    3000
tcctttcgca ccataaaata atgtgacttg acccatagct ttgcttgact tgtacatatg    3060
tgacccctta ctcaatatag tactaatacc tatacaatat ttaacaattt gctaataaca    3120
agaacaaaat acatgtgggc aacgtttcac agatcagatc aaagtcacgt gcgaaagttt    3180
atatatatat atatatatat atatatatat atatatatct cttatgtgtt gatatctatc    3240
aatttacatt aaccacccgc agaagaagat agggttgtta aattgatggg tagatagaac    3300
ttaacattct ttacaaactt tgtaatttgt tgtatagttt catgaatggt gttaattcat    3360
ggcctgaaaa taccatcgat gtatacaatc tgataaggat aaattgtttt ggattgacca    3420
tctattagtt ttaaaatatg attgtataac ttggattggt tagctttcag attatactat    3480
atattcaaaa caagcttttg tacgtatatt atatcatttt atccgcttaa aatgtaatta    3540 ctaattttc tttcatataa gattcaagtt tacctaaaga aaaggattc aagattacca    3600 gttatctttt gcaaagctta ttaattataa attcttaaaa ttttagatta aattaaaata    3660
tggaccgagt agccaacgaa tgaatctcac atcacggcat agttgactag ttgttgttag    3720
```

| | |
|---|---:|
| tatataatat aatcaacatt gctgcttcgt tctgacgtca atctgctgaa tcagcccctt | 3780 |
| caacaaaaac tacgtcatgg ggctgacgtc gagtgtccga cgaaactaat gccgttttca | 3840 |
| ttggtgcatt agtcgccact cgccagctac atcgcaatta tttctctctt taagcgttga | 3900 |
| aaaattgtct agatcttact tgttaatgtt attctattac ctaataatta tcttttgtct | 3960 |
| ggtctaaata cttacatttt tatttaaaat ctgaaccaaa actcaccaaa aaattagata | 4020 |
| attttaccat taaagatatc cacgactagt ggagtatttt cattacaaaa aaatgaattg | 4080 |
| atcatatcat atgtgttcga agcttattat attgagcaaa aaaacattat ttgtacacgt | 4140 |
| ttcatctttg atgaggtaaa cattgcgatg gacgtgtaaa atatgttata cttttttttt | 4200 |
| ttgtgaacat ccaatctatt acatacatttt gttttttttt gtcatatgaa cgtaaaatat | 4260 |
| attatttttca aaactctata ttattagtta ccgtataaat tataattaaa accacctatc | 4320 |
| aaaatattaa ataaaaaata tttaacgata tacaatcaac aaaattaagc aaacaaattt | 4380 |
| attcttaaat ttcatctgct atatattttc aaaaaaaaaa taaaaaaaat tgcgacacat | 4440 |
| attgaaatgg aaagattaca aagaaaatt ttaaaatcat tgctaatttg gggtttatca | 4500 |
| tagctcatat ctctctctaa tatatctgac tttgtagaac acagttttct attagattcc | 4560 |
| tcctatcttg aaacctttta gtgttctgaa aggagtagtt tttaattttt aatctttaat | 4620 |
| tattaagcga accgcgtaga ttagtgtaat aagagaaaca gataaattct gaaacaatta | 4680 |
| aaaacagatt gtatataatt aagtgagccg cgtactggga aaggtatata aaataaactc | 4740 |
| tgtttcctat acatcatgac agatcatatg ctaatgtcaa cacctaatct atctttttgt | 4800 |
| ctctctttat ttagattcac gcatataagt ctagcagagc acatgtccta tcgaaattt | 4860 |
| ataatttatc attggcttct taaaatataa cctagtgtat gtaaattata tttggtaaac | 4920 |
| ccaaattggc aaagtcattt gggaacgtgt atgtacgact agtcctataa attctgatct | 4980 |
| ccctatccgt tcaaaagttt | 5000 |

<210> SEQ ID NO 22
<211> LENGTH: 2300
<212> TYPE: DNA
<213> ORGANISM: Arabidopsis thaliana

<400> SEQUENCE: 22

| | |
|---|---:|
| tacacacaca cacacccatc tcatttgcaa atttgcaatg ttgctttgat tagcacaata | 60 |
| gtatattgag actaacatat caatatctgg attactaaag acagatgaat gcttcattag | 120 |
| ggggttaata attgtgtgtt tcaggtcatt ggttctcttc ttcttgatat acttactaac | 180 |
| atgagagagc aataaaaact tttagttcac ccaaaagaga cagagctaaa tacattttca | 240 |
| gccacggaat ggttaaaata tgtgacccgc gcacagattc gataaagtct acaagacagc | 300 |
| ttgttaatttt cttaaggaga tcgtactaat gcagttaata tatcactagt gtttattgct | 360 |
| tattttggtt tccacttgta agctttcttt attcctgtgg cagcctaaac gaatcctaca | 420 |
| atagcctgaa gctcatccat tttctgtaaa ccagagaatg tctcataatt cacaccactg | 480 |
| ggcattgtct tgcaaatatg gatagaccag taaccctcat tttgctaatt agcaatgcat | 540 |
| ggatgtatga atgtttatt gaatcaggtt agatggttca aagtaggttg tattgtcggt | 600 |
| cttagtggaa cttggttcga gatagacata agaaccatta tatatttatc tcggaggtgt | 660 |
| attatattag aattagaatc tcactctaaa agttcttgga cggagctaaa ataacatata | 720 |
| agagacatgt gcaaatccat tcaaaaccaa taaactcttc aactgtatta taaatcttac | 780 |
| aactattaat gtctaatttt agctattgcc actacggtct aaaatcttcg aaaccgtgtg | 840 |

```
gaccatataa ccctgatgag tgggactaat aagattttta acattacccc ttagaataga        900
aaggtcctat gctatgtatt agtacaagga aatttcagca gccacgtttt tttaccacac        960
cactgcttat actaattagg aggattactt agcttggttt aagggtttag taagaaaagt       1020
ccatcttctt cctctctgta cgcccttTga atctcatctc ataaagagac aattcttTct       1080
agctcccatc acccttttgc tgattgctga ttagtttTcc ctttTcatat cagatattat       1140
atttcgagat ttgacatata taatacaatg ttttcgataa actacaaaac caatttcgaa       1200
aaacatataa gtttTgctgg aaaaagccgt cgttgatcaa agccacacga caggtttTat       1260
gcctaacaac gttgacccat taatgaaagg actcaaaagc aaccctcata gtcacggcaa       1320
gattcaatta ctttTcctcg gacccaaagt tggttcaatt tatgaaccag tttctacgtc       1380
taagtcagtc gtctcacctt ataatcttta aagtctcccg ctgcactaat cactccgttt       1440
catcgtttta tatatcactt gattttattt tatttcataa aatatttttt tttaaataca       1500
gattttTctt caactatgtt ctagacttct agaagccata aaagattaca atattattaa       1560
aatgcgggac aaaactacat aacgatacca tttaacgtac gaaatatttc taatttacct       1620
attcgtttat aaccagattt tatacctgtt tagatgttta ctgttTtaaa aactacacat       1680
tcatggtcat ggaggatatg atatctaaaa ccttaggatt caagctttcg cgttcaagta       1740
gcaaatcagg cctcttatgt atgcatctgt tccggtctta taatcgagga ttcacaccaa       1800
attaaaaagc atcgatctat tcgggtttca tacaatcata ctcatgggtt acaacagtca       1860
acaaacacat ctatctggtc atctggatct caaactcgca cctcacaaca caatatctaa       1920
ccgatccgga tctcatattc aattcgtgga tcacaattag acacatctaa ttggatctca       1980
tagtcgcgga tcacaattaa attcatctat acagatatca tactcgcgga ccacacatca       2040
catgacataa acatcacac tgaaccctaa ggtttagtgt agtgtgcatc agccatggcc       2100
gagtcaaaat gttaagattt tttttttacc atttatagta aactaatgga agtaaaaacc       2160
agtaatgcaa agaaaattca gagaaccaaa ggaaatatct atcaagacac caaaaattct       2220
aattgattaa tcatgacaac attacgtcgc taccctcga accaacatct ataaatagag       2280
gatcggtgcc attaacattc                                                   2300

<210> SEQ ID NO 23
<211> LENGTH: 3000
<212> TYPE: DNA
<213> ORGANISM: Arabidopsis thaliana

<400> SEQUENCE: 23
atctcatggg atcccaaatc ttattattTc cctgcaacaa gattgttatg taaatcattg         60
gttTtgaaaa tcaattttct gtgtaacaag accatctccc aagattgcta tgtaaattat        120
tgactgcaga gatcaatttt cttTtattTt attaaaagaa attaatcatg aatacaggat        180
attatattgt tagaaaaata aagaaaattg atttctgcag aagaatgata ttcgttatag        240
ttttacaaac aaaatcatat tttaataatt agatttagcc agaacggact tggggtttTc        300
atatcacctt gcaaccagaa gttattaaaa aaaagaagc aaatttgctt tgtaaactca        360
tacgtattac ttttTgtcgc atatgatata tgattgatcg ccactccaaa ttattttTgt        420
ctgaattgca gcttctgccg cgtaaggtaa gataatcaat ctagcattgc ctatTtgttg        480 tatttttat tctgaccagt gaccagcgat caaaagtatg ggatttgggc aacttgtata        540
gtagtttaat tggacttatt tcgcaagttg tcaaacaatg tctcgagttc aacccttgta        600
```

```
gtcgatcctc cttgtgatag aagtttattg gtcttatgtc ttaagttgtc aaataaatat    660
ggagtgtgaa catttgaatt ataggtttag tcgtagagta attatatttt aacctcattt    720
tctaacttgt gtgtactttc tgttaactct tgatttatgt gtttatcatt tttttaagtt    780
atgtgttttc cattatgctc tgtttatcta caaatagtag tagctgaata accattttg     840 tttttaaaaa aaatcaaag ttggacttcc aagtcccaac taaagattaa aacatgcatg    900
caaataattt ttgcaagtag gatttttcttt cttaggaact cagactccag aagacgactt    960
tatttttccc aaattgtttt atactcaaag gaataaatta tccacgcttt gtcacacaaa   1020
aaaaaataaa aattatatag atatatagat atatacatgc aggaatttaa ataaaattat   1080
taatcttacg taattaagaa ctttttttatt tttttttaaa aatcgtaatt aagaacttga   1140
atggtaaaat actagaagaa aattgttagc gtcagtgtga aagcaaatta tactgtaggt   1200
taacttttct atagtgagca aaatacatta ggttatctaa attcaactaa cgtcctattt   1260
ctagttattt gactaaccaa atcgatttt tcgtgaagga aaaaaaagt gtttagtaca     1320 ctcatatagt catattctta catatagaat tcaagatttc gaactaaagc atacgacact   1380
agacttaagt ctagaaggat gacggaaatg agaataagct aaaacgtttc tacgaaatta   1440
agaaattcgt agcatccaca acacacatat tcaaagtctt gaataacaat aaaattatgt   1500
tcagctgaga gtctgagacc gcgtccaaca tttaaaaca cttttaaaag tcatactata    1560
atatctgagg accgtgtcta gtttcagttt attcggtttt acaacagcaa tgatgcttgt   1620
tgaattatgg tttcattcta ttggattatc tgcaagactt cttaattttta atatatagct   1680 cgtgatgata aataacaat ttgacttcta aagtctagtc ctttatagtc ttaacaatat    1740
tcattttgac caggttgagt aaatcagaca aaaatctaaa gacaaagaat aatcgtttcc   1800
tcaaatatgt acttggtgag ccgtcttaat caccatatgt acatgagaat aaatgtgtaa   1860
tttggtggtt atttcataga aattttgggg aaattgttgc acctctccac tctttgccag   1920
tctcgtgtga tcttaattga ctcaaaatga aagaaaaaaa aacatgaaat taaagcaaat   1980 attcctatt tgaattatgtt cctttaagat ttttaacaat atttttttaaa tgataaaaac    2040 tggtctcaaa gagcctaagt gggtttccta gcaaaaaaag atactcaaag taatttactc   2100
ctcaaaataa tgcaatgatc taatgaagat ctgttcaaat agtattgatt ttccaaattt   2160
aattatactc aaagagttttt aaaatctgtt cttgttattc tatgctttgt tttacatgta   2220
aagtacttaa attcacttga tatttgttat tactataatt ttagaaatgt gtcaaaattt   2280
aaaggagcat gcgtgtaatg ccatatgcct tatgtacgag aacttgtaat gcgtttgcaa   2340
tttgtagtga catgtaatgt ttttttacgat agtttaaagt gcaaaccgct tccgtatcaa   2400
acgagaagag tcgtctagca tacaacaccc acacgagagg aaccgcttag aaagagaatc   2460
cacttgaaat tgctgtccat gcattgctca aattcattga tacttggtct atgcaatttt   2520
acactacctc atttctgact atttcaattt gtcaagatat tataacatgc atttataact   2580
tttttgtcga cgataaatca accaaacgaa tccggtctgt atgtttgata acatgcattc   2640
atacaaaacg attatctgtt ttttagtcta tttaatttgg tttctacttt ttactttttgt   2700 gaaactaata ataatagatc aaacaattaa ctgatataat ttattaatttt aattcttaga   2760 ccaagtaaat gattcatgaa atattaaatg cacgactaac tttagaaaaa tgtttctttg   2820
tatacataaa gatagaatag aagaaaagta ggattagaag aaaaaaacga aaatttcaga   2880
gtagtttact aaagaaattc tgagaaattt tgtgtgaaaa tgaaatgaaa atcttcaatt   2940
ttagtgggcc cctgctacat cagtcccta tttatatctc ttctcaactc taaacccaaa    3000
```

<210> SEQ ID NO 24
<211> LENGTH: 6100
<212> TYPE: DNA
<213> ORGANISM: Arabidopsis thaliana

<400> SEQUENCE: 24

```
attttgtttt tctttgcaag aaaagtaaaa tcccttatca attggactga cccgactctt      60
atgtacttac caacaactta ccagctttat tttttggtaa aaacaaagtg tttctgagca     120
gcttgttttg ctatggggta tttagagcac ctccaatggg aggctgtaat gcaattttg      180
tgaggctctc ttgatatttt cgatgaaaaa ttaatcaaaa ctaaattaaa atgagagagg     240
cggacacgtg tccaaagcaa acaaattctc aatatttcgt ttttcacttt ttcaatggcg     300
ttaatacatg gttcgattcc tggtacgtct gcggttcgat tgggttttc aacctcagtg      360
tcaccgagaa tatttctcaa tgttccggtg gtgaagcagg gttggaggga ttcgtgtcgg     420
agagaggttt taagagcaat ggtgcaggag acagttcggg ttgtttgttt tttctgttga     480
aggggagaga gatgatgtgt accgtatatg ggacttgtgc aagatcacaa agagaagaac     540
aatgaaggat tttgacatgg tcaaactcga catggtccgt ggctacttat gtgtgtgact     600
tgagttctcc atgttttgca attaagaacc gttggtgaca aatggattag aggcactcag     660
ttttggcacc acaagtagta catcttgttt caaacataaa gtcttgtact atattgaaag     720
atacttcatt ttgaatgtct tgtatcaaac ataaccatat attgaatgat tgtacatctt     780
gtttcaaaca aaacctcttc ttcttgtttt atacagagac acaaacaaca cttctacaca     840
acacttcttg ttttacaaag acacaaccaa catttattct tgtttttaca aagacaaaac     900
acttcttgtt ttacaaagac acaaacaaca ctagttcttg tttttacaga acaaaacat     960
atttttaat ttccacatct tttaaataat atttttactt atgtatgttt aatgtttaat    1020
attttatgaa ttacaataat tattaaattt tatgaaataa ataattttta aataatatt    1080
ttttttcag agaacctcta taagagagac taccattgaa gtatgaaaac ctagaaaaaa    1140
taatcaaaag ctctttata atttttcaaa agtttaat cataaaaat ggagagagcc        1200
cctccataag gtctctccat tggagatgct tttagttctt gccataaaac ttacatctat    1260
ttgtgaatat tttagtttaa aaaacttata ttatttgtga atattttatt tcggatatcg    1320
atagactttg actttggttg attatgatt atgaactatg gactattaac atgacaaaca    1380
aaaactgaag actttaagt gttctcttta aataatctaa attttgcaag ctctatcctg    1440
cccatccttt atgtttctgt ctaatttatt agtgttttta caattaaact ttcctacata    1500
ttagaaaact aaaatttat aatttgtgaa ttcatgttag ctacttagct ctaactttat     1560
ttatactcaa attaagtatc gttccaaatt ctccatgttt attatcatat aaattctgcc    1620
taagtgcttc agttttctat ttgccacagt caattaaaac ttcaactaaa tgatgaaatt    1680
caatttttg aaatttgaag tgttattctt ttcacaataa agatcggcat ttttttcttg    1740
ttttatatca acaaaaccgg cacttttttc ttttttcaag actggcaatt ataacgggg    1800
tataaaattg aacaaattat agactctaaa ttatttcata tgtatatttt cagtttaggc    1860
actcggttga ctaagacttg tatcccaaga tgcacgttag cttattgcat cctagctgac    1920
gtataagcta gagaatcaaa cacacattgg tcaatgcagc tgcactaatt taataaaaaa    1980
tctgtgtaat gtagttcgat ttgttccgtt atgtgtgata catttatat tctctgattt     2040
ttttttttct tttctctttt ggataattca aagtacataa catgaatttt gacatattct    2100
```

```
gtcagtaact aaaagttagc ggtgatgaaa atcactattt actgcagttc tatctatgac    2160
catgatgtct tgaaccatgt aatgaatgac acaacttagt tcttgattag acattaatta    2220
tattattttt tggtttcttg ccacaagata gttcttgaat agttttttaat tttcttttta    2280 tatatgcagt ctacagatat agctgtatag tagtggaata gggcacacat gttataaata    2340
tggccatttg aggtgtcaaa cattggtaag acgatgaaaa agaactgaga gtgttttgtt    2400
tttttggaga gaaccgtcag ttcattgatt tcaccttcga aatgatcatt gcaaaagatt    2460
tcaacatcct tttgaatttc actttgtact taataaaatt gttttaagaa tgtcaacttg    2520
taagctatac tagttataat gacttaaaaa caagttatgg acgggttggt tttctatcaa    2580
aatttggact atttctcaac tgtgtatgtc atattgacac tttctgaatt ttagttaatt    2640
atattggata tatcaaagag actgaatggg ttgattttca ctcaattcaa cttctcattt    2700
aaaaactaaa aagttggtac gccattattg taagatagcg aaacatgcat ttagactaca    2760
agaaattcgt aatattgtat agcagcaaaa gaagacttgg aacctctgat atcgttgagt    2820
aatatgggtt gtatgaattc ttttttgaagt cagtgttagt aattaacttt gtaatgtttc    2880
ctttgatatc gtgttaaaca tataaagaag aaaactcaca aatcatctct ctaattacta    2940
tatatgtata gttagaaaat atatatttta gcaacttcat gtaattaaaa tatatgttttt    3000 gtgctccaag agaggactaa ttagtattaa attgatggta ttgatactta atgattgcct    3060
ctatctctta ttttatgttt taaatcctca ataccatga tgaatcccta ttgacaaatg    3120
cttgtttaat ttgatttta agtatataaa ccgtctcgtt tctctttagg gcatatttga    3180
ttaggttttt tagttaatca tcatgtattt tatttgcaat tacaagtttc ttggttcgct    3240
attaattatt ttaattattt tttgtttaac ctttgtaaaa atctaaaatc tatattaccc    3300
atcttagatt agaaggattc atttcccgta tctttagcat gtgagaacta gtccttatgg    3360
ttcactacta tatataatgt ttacacttca cggtgcactt gcatattagt aaaactcgat    3420
cagatcaata cgggaaatgt aaaattaaac gcactccaaa acagtaattt atttttaata    3480
aacatgaatc agtactggtt atacttatta cccaagatag tctgactact acttgaatct    3540
tcaagccaaa tgattaccaa agagaacaga gaacaaaacg ctgaaatctt tctttaagta    3600
gtcattggtc taggaactgt ttatgttttc tcttcttttt ttctttcagt aatttaatat    3660
tccaagaaat tgaagataat caatcactcg atacaaatta tttatacaaa actaagaaaa    3720
gaaagtcaaa ggaagtgatc gggttctacg gtatgaatgt caacaaatca tatatatgaa    3780
agttagtaaa ttttttttat atgattgaca catcatcatt ttaacatttg tcatatgttt    3840
attaaataat taatgtaatg aattattaat tataggttag tgatacattt attattcaat    3900
tttatatatt attttattat atattcaata tactattact gaatttattt taatattaaa    3960 agattttttca ataaaatcat tttaatagtt ttttatact taaagatttt tttgtaatcc    4020
aaactcaaag tatgattata taataatcgt ggattagcta atgatttgag taggttattc    4080
tcttaaattg atatttatat aataaatcac taagagtgca taatacgtac gaagctccat    4140
catcaaattc ttaggattgt agaatcgaac actaccctct gctagatgaa cgttgtttaa    4200
accgcgacgt agcgcggatg atcacctagt ataagttaat tcttggaact actttgaggg    4260
acacagtggg gaagcctatt aggcactctt acctgtaaac gaagccaacc tcattttgtt    4320
gattttgact ttatatgttt tcttttattt ttattatttt tcttatgtta aaatatatca    4380
aaaaagttac gcagttaaaa caattaattt cttatttag caagacaaga aattaacata    4440
cgttaagaaa aaatagcgat atacttaaaa ttttctctaa actatagttt ctgcatatag    4500
```

```
tgagacatta tccaatatat atatttatat atataaatatg atcgggactt tatattcttc    4560
tatatatttt aaacattatg aaatttcccc aaaaatagta ctattcatta gatgtttgtg    4620
catataacaa agtgaaacca acaatggtta catattttg tgttaatatc ttttattttt     4680
tttgtgcgtt tatacttgtt agttttagta catgacttct tataataatc acgaaaatcc    4740
ttttaaagtg ccatttatga gatatgcttc tatgataaat cggaaggatg agattcttta    4800
tgtgaaagtt caaactctta ttttcttct taccgaaatc tacaaaacct gaacaatgga     4860
atatatgata ggatgagaag gtacttgttt gaaatacctc gttattcaat attacttgtt    4920
tagggttcac tttctaatta gtttgctcga cgtacgtcgg tttaaagttt atttcctcca    4980
aactaaaagg tttcacacac acgaacacaa ctatatgcac atgtgcgtac ggcttacgtt    5040
atgtatcaat acatactagt taaaaaaaaa aaactagtaa tgcactgtac cgtctattaa    5100
acgagtctca acaaaattaa gaattggttg taagaatatt cttttgccat aaaaacgtat    5160
ttttaatcac gtgaaaggtg ccgatctagt tgctagcggt gtcttttttt tccaatcctt    5220
tgatctaata ttagaaatag tcaaaaatat ttcttaaaat gaggaaaaac taaacctgaa    5280
taagatccat taataactga tttccaattt gtataaaaat agcttttcta gaaatcacct    5340
acttttcgcc gcatttcaat ttctttgtgt gtatattgac atgttcaatg agattttcaa    5400
atttagttaa gaaaatccaa aaacattcat aaatattttc ttaagaagag aaatttgact    5460
ttttaatatc ttaagaaaat tatctagata tattagtgta atggatttga tttatctaaa    5520
atcacacacg tctatgagtt ccgtaccaat atagctaaaa cttaattaaa tcaatagaca    5580
tagagcatgg agttgaaata tataaaacaa aagcaatatg gagtcttta  gttttcattt     5640 gaaacaccac gcagttttat cattactcga atcataaaac agcagcatgt ttgttaagac    5700
aatagaaaga ccaaatgtaa acgtgcaata tgtctattag attatgggac ccatgttcct    5760
cctataatgt caggtggcag acacatgacg cagactctga cgcttttaa caaaaccaaa     5820 agtctccacg aaacttccta caagattctt ctatcttaaa cctaaatata catttatata    5880
atctatataa ttgataaatg ataaaataca atttggagag atatttgagt cgacgccaaa    5940 acccttttg taggcgaatc atctggaccg gtaagagact ctctcatcga taataaccac     6000
ataatttaat caaactcttt ctctctcttt ctaagatctt ttgctttgct cttttccttt    6060
ttgatcttcc tatatatgga gaagcaccaa aacggtactt                          6100

<210> SEQ ID NO 25
<211> LENGTH: 5001
<212> TYPE: DNA
<213> ORGANISM: Homo sapiens

<400> SEQUENCE: 25
tctatctgtc ttttggacaa aggacttctg atgaagagga tggagtggac catattcttt      60
aatccatgac gttatttgtc cccatcaaat acaaatatct aaatgtattt atatattttc     120
attatcacta gtcctcattc tcattcccct cactccccag tgggatctat cctactaata     180
tatatccttt tgtctgtgtc tttgtataat gtgtactatt ttgaatatat cattctcatt     240
taagtcaata gagttccgca atcacttact cacaattctt aaacttacac agctctggac     300
accagaagtt ttctcttaaa ttcttaacag cgaaatctga ctgaagcgac aaggggttac     360
ttggggttct ttagccactc aatgtaacta ttcctatgtt ttgctgcgga actattatgc     420
ttgattatgc gatgccacct cttccttttc taaattccaa gcattttgaa ttccaaaaac     480
```

```
aaatctgagc ccccccattt ttttcttttt ctttctttcc ttttctttt cttttaagtg      540 agacagggtc tcactctgtt gcccaggtta gagtacagtg acacaatcat ggctcactat      600
agccttgacc ttccgggctc aggtgatcct cccacctcag cctacttggt aggtgggagt      660
acaggcatgt gccaccatgc ctgactaatt tttgtatttt ttgtggagat ggggaatccc      720
tatgttgccc aggctggtct caaactcctg ggttcaagca atccactttc cttggcttcc      780
caaagtgctt ggattacagg catgagccac tgtgcccagc cccaaagggt tttaattgtc      840
tacttataca ttatagagag agatcttact ctgttttcct gtttttactc agtattatat      900
ttttaataca tatccatgtt actgcatgta catctagtct attacttcta actgccgtag      960
aatactccat gaagtggatc cctacattcc actcacccac tcccccagta atgagcagct      1020
acattgcctc cagttcccca tcactacaaa caatgactta atgaacatcc tcatacatgt      1080
tcctttgtgg acctgtatga aatctccat aggatataca cccagggtta acagctgggt       1140
catgggtgtg aatatactta atctggtcaa ggaatgccag aatacccttc aaaacagcca      1200
tgtcagccta ctggcatggt gtgatataat agatcctgta gtcccccatt ttcccaacac      1260
ttaccagtat ccagtgttct caacttgtca gtctaagagg tgtaaagaga tatctcattc      1320 ttttttttcat ttgcattttc tgatataact gagcctccag gtatgctcat tagtctttgg     1380
ggtttcttct cgttaaattg cttattcatg agctttacgc attttttact agtgtttctg      1440 tcttttttctt gctgacttac aagagttcct tgttttaga cattgaaaat attggtttta      1500
gacactgaaa aatatcttct ctcaatctgt cagctgtctg ttcatttggt tcatgcatag      1560
aggaaatgtg taaaacagaa atcttcattt ttatgtaatc caattgatag gtattttgcc      1620
ttatggtttg gagctttaga agttttaaaa aagtccttcc cacttataag tgacaaagac      1680
agtcctctat attttcttct actactgtaa caatttttact tttcacattt ggtctttaat      1740
tcacttccaa atggattcac ctctgttgtt ttagattgga gtccagtttt atttttcatc     1800
atacgctgaa cattttctct ttttaaaaaa atttttttgta gggagttttt gctcagactg     1860
gccttgaact actgacctca agcaattctc ctgccttgac ctcccaaagt gctgggatta      1920
caggtgtgag ccattatgcc cagcccattg agtattttct actaaatatt gcatgttttc      1980
ctcattgatc agggaatcat ctgtattatc ttatacttaa tacccaaata tacaaatcta      2040
tctataattt ctctactctg tttcaatggt ccatatgcct gatctgttgc aaagatcact      2100 actttaatttt ctatggcttt aaattatgtc catatgtgat aggggttagtc ccccttttca     2160 ttattccctt agcatttta cttaaggcca ggaacagcag ctcacgcctg taatcccagc       2220
actttgggag gccaaggtgg gtggatcact tgagcccagg agtttgagac cagcctaggc      2280
aacaaaacta gactccgtct ctacaaaata caaaaataaa aattagctgg acatgatggt      2340
gttgcctgtg gtccaagcta ctcaggaggc tgaagtggga ggatcacttt agcccaggag     2400
gtcaaggctg cagtgagctg tgactgtgcc accactacac tccagcctgg gtgatacagt      2460
aaaaccatgt ctcaaaaaaa attttttttaa cttagtcata gatttttatta catctgtatt     2520 ttagagtagg cttattatta agttctgag aaaatttatt tgtagcttgt attggaatta       2580
cattgagcat gtgaattaac gaaagaggc ttaagctttc tatatagaga aaccttccac       2640
ccaagggtat agaattattt aattaaatca cactatattc ttgactgaac tttaaaattt      2700
ttctccaaac actattctgt agttatccaa gctcatgtaa taatcataat aactctatac      2760
tgtaggtact tttattatca tcatttaaca gatgaggaaa ctgagcccag agagataaat      2820
aactcaccta agaacacaca gcaagtaagt agcagaacct ggattaacat agtttagtcc     2880
```

```
atactcttag ccattatact gcctctgtat ctacagtcag ttactttata gtttggctgc    2940
ttctatgcat gtcatcttgt ttttattaca ttttctgatg gattgttgca gatacaaaga    3000
aaatcggctg atttttttta agttgatatg tgtattgcat gatgttgtta aattctcttc    3060
ttagttctaa tagtctatta attttttttc tttttgtata tcaactgtaa aaagtgacag    3120
ttttaccttt tcttttccaa tgtttaaagc tctcatttct ttttctttcc ttatagcatt    3180
ggccgagacc tccacgacaa tgctacacac tgtgaagtag tgattgtgag ctaagactgt    3240
cacttataga aaatcatgt attcctagaa gaaggttttc atttcatctt agctagagga     3300
catggagcac ttcaggaaac tatttcacaa aaatgtaaat tagaaactgt gtctggtagc    3360
caataatcca ttttttaacag tggccctgtg ctcatctaag caacagaaat tactttgta    3420 taggagatgg cccttccagg ggagaaacag ctcagttgtg atacacttgt cttcatcctg    3480
actttaagta catttaactc cacactaaac ccttgtggcc acaacacagc tctgcacctg    3540
tcatttgctc tagacaaact gctaaacgca attgtttctg acaatggatt actctgtatc    3600
ccgtggggga attctcagac agcagcatta gaaggggcct tagagatcaa ccatttctct    3660 tatttttacac acacctaaaa ctccctacag ccgtgcttca tcagcttcga gcagatgagc    3720
cacccagaag gcagctccag ttattaggtc ctagggcctg ggtgtagtca ggcccttttgg   3780 aagctccaag tcagagatca aacacatcct ccccactacc cacgcctagg gtgactaatg    3840
cctgtgggaa aaacaactga actaaaaagt cccacaggaa cctcaaaccc agcacatcca    3900
aaatggaact tctcaccatc tcctccaaac tcagtcctct tatacagtaa tccctgtaaa    3960
gctagaacaa tctccattcc ccattctcag ggccttcctc tcccgctcac ctgaggagct    4020
accaagcctt ggcccacaag ccctctgaga gtccctcctg cccaccctgt gttctccata    4080
ctgaataagg acttggccac accttgtcaa ctcttccctc tgctctactc ctgaccctgg    4140
atccatcctt catgctgtgg ctgaagggat cccccccatca tgcaaattct gccacatctc    4200
ccgcctaaaa cccaggaaga ctccccacta ctctcagcac agaaagtaca ctccttagta    4260
tggcatcccc tgccctcatg gcatggcccc atccagccct ccagcctcac accctgcaag    4320
gacacctaga cccccacctc cctcaaccct tcatgactgc gcttctgatc cctgtttccc    4380
ctggctagac cctgcgtgcc ctcccgctgg aagcggtcta atgcctgctt gttttttaaca   4440 ctcaggttgg ggccctgcc tgctcccggg agcctttgct gactcctgga ccccgttgct     4500
ccggctgagc gtgggctctt tctctaggtc tttcctccca ggactctgtg tattcatcct    4560
atcgttaaac tggattctct acaagagtaa taattgcaga gtcagccagc tctcatccct    4620
tttcaggttt cagaaaagac ctgtgaacaa aacgccttga gtctgattta gtgtggcaat    4680
gccccaaggg tcctgttctc cctgggtgtc ctgcacctgg tgcaacgtcg gcctggcatc    4740
tagtgagcca tctaaaggaa cgatgatgag tgaatgattt gcctacccct tccagtacta    4800
ggctggaggt cgtggttagg gcccatccct acgcaggaca tgcaaagtgg gaggcactcc    4860
tctctctacg tcggcagggg gcgctgcaca gctgcgggc ggggtagctt agacacgggg     4920
cgtccggcta aggccgggga cccagggtgg tgggcggggt gtcccgcccg cctgtggacc    4980
ccgcgcagta actgcgaaca t                                              5001

<210> SEQ ID NO 26
<211> LENGTH: 5001
<212> TYPE: DNA
<213> ORGANISM: Homo sapiens
```

```
<400> SEQUENCE: 26
atggtttaac ctttgatttg gggttgcata tgctggcatg cttctggggg gttgcctccc        60
ttctcccctg attcttctct tggggtggcc tgccagcact tgggaggggc cacatacaca       120
gtatgtttac tgaaattgta cgcatgttca cttgaggcat tcttcccttta ctagttgagt       180
gttcttagaa gaagctcata caccagttaa attcgaccat ttttccctcct agtgctcatg       240
cttaagccca ttcgcccagc tcctaagatc ttatccggaa gctgctaatc accagcttca       300
ggtgttctat ctattgggag actgcctttc cctggtacca gctgtgacca attattattt       360
tagagaaaca gtttaataac catctgaccc tcacctgatg gttgcctgac attcctagtg       420
gtggtgggcg gggagtggcg ggggaaccct cttctgccct gctcatgtct gactagctat       480
ctgccgtgac acttccactc ttcttttggt aagagcatgt atgtatgagg caggaggtag       540
aagctacttc ccatactcct aggctagaag tatcccttca aaagcaactg accatttggg       600
ggaagaagcc ttagttttca ttatccacac aattgcccta tttctgcact tcactggccg       660
cacaaatcac ttggactcat gtaacagaca catgtgactg tatccataat aggttcattg       720
cccattgcac acagcaagtc aatacgccga gaggccaggt tgcagcagag aaagaggttt       780
aatcgtaggg tcaccaaatg aggagacagg aagaaacctt aaatctatct ccttgtggca       840
tttgggggcta gggttttttaa gagtttggga gtgggctgat gtgttggaga tggttgactg       900
gttgaagagt gcatggtgaa gtcatgggac agggtgaagc tgtattttca acctgatccc       960
ctttctttgt gggggtttttc aaactgaaat atggtagaat tggggacctg aaaaacaact      1020
taagtgattc ttaaacaaaa gcgttctgat tgtaatgtca gagatcccat ctaaaggaac      1080
aatagggata caaatcaatt cctacacaat cttatgaccc taatgtcaga aatcctatct      1140
acaggaataa tgcagatgca aatggtcagg atcagtgct acgtgacttt gagcaacaag      1200
gaagtgggcc aacgtgcaac ctaatcaatg cttaattata actatattcc tgtccagaac      1260
ccagcatgca attcttgtca accctgtgag ggtggttttca tgactctcaa tggcctacca      1320
ctttccatct agtagggcaa acctgccttg tctatcactt tccttgtaat aagcccattc      1380
tccttgtcag ggagtggtat acaggtgata agtgagactt catgaaaagg ctatggagct      1440
tgtagggcaa attatttgct cctaagagac atcaacagga caagatagtc ttttcttatc      1500
ccaggtgtta tcagtcctta gtggattgat gcctggaact gcagagctcc ttagaaaact      1560
aagcccaggg caacctaatt gatgcagacg tgaaatctgt tcaagtgacc tctagcaagt      1620
cactgcaagt gactgaatac aaaatagact gttgcaagaa aagagcaact tgcagaacaa      1680
tatgtatagt atgattccat ttatatagcc agatagatat aaatacatag agaagcattc      1740
agaagctctg caggaatgct ggcactggta acctctggaa gccacaggaa tcagggcctc      1800
aacattgtat tctatgtata tttgtattgt ttgaagtttt tacaatagca tgcatgcatg      1860
tattgcttat gtaattttct aagatttttaa ttttttataag tacacatggc ttctccttta      1920
tttgaaatgt gtactagatg atcaaagcat tcttctagga gaaaataagt ttttgtggcc      1980
aaaaaaattc tttaagttat ttttggtttt tagggggttg cctccatgtc acagcttaat      2040
catcagacac attaaccttg cagctcagca cgccctctgt ttgtcagcag accttcctcg      2100
cccataggggt aagcaataga aagcttatag gtatcagttt atttttgcctg ggatcagggt      2160
ctggattgtg aagtgggaca tgttgataaa cctcttctcc aaaattaggt caatgggcat      2220
ttggctcata ttaccagaat gctggctggc catgtacagc ctgtctccga gagaggctct      2280
aatgtggccc ccacattaga acaacctgcc aatgaccaca ttagaacctc cattgttaaa      2340
```

```
atgcaggttc ctgagcccca tcccagatct gaatcacaat ctccaagcat cagccccaag    2400
aacctgaatt ttgttgttac atgcagataa agtacgagaa ccacttcctc catgggtgaa    2460
ctgaacttac caaaatagtc agtcccgagg ggcagagatg gcgtaggtgc cagttcttct    2520
ttctcatcct agatgctcag agtcaaattc ttggctcagc aatagacaag tgatttcact    2580
gtgggaagac aattcagagc cctgttccag gctcctcaca ttgattctct ctgtcttctt    2640
ccactcctct ttgtcatctt tgatgtcccc ttgtgagcta cgaaaagact ttctgggaca    2700
cgacaggata aaaaaataaa taagtgcaag cagccattca ttaaacgttt agccaggatg    2760
ctgctttaac tgcatcccat catatctcat aatcttcac accagtcctg agatcaggta    2820
ctattattaa cccgatttta cagatgtgag gaactgaggc ttaacgaagg taagtaactt    2880
gcaggtgcgg gtatccagct ctctaactcc agagcccatg ctcttaaaac cctattactt    2940
gtccctggtg gaggtgaaca ctgggggccc tttcatatag gactagccct cgggctgcaa    3000
tctgagcgga aaagggagga tgagggcata cttcgaagct tcttttgcat aactggcgct    3060
ggatttttac tgagacttta cgttacagtt ttttttttt aattttcaag gtgcttttac    3120
gaacacatga ataaaatatt tgtgtcattt tgaaccttac ttgtcttatt ttatgcatgt    3180
atttatttat gggggggcac aaggactcat ctgtggtggt gcagccactg taaataaatt    3240
agtgaaacta cttcacgtca atttctgttc agtacacttt agtgatggat cggaggaaat    3300
taatacatgt ttacaaaaag cccctccccc agttgttaca tatgcctcag agataccagt    3360
tgtgaaaagt gcaggtgcac ttacacacat acgcacacac accccacaaa tggtatcata    3420
cgaaaaaaca tacctgcaat ctgctttgtc cacttaattg tatatcttgg atacagaact    3480
tgtttcactg gaaggctaaa aggcaaagtc tggggaggcc tagaggacac aggggatggg    3540
aggaggcgct ctgagctgga tgtaaggtct ccacccacgg ccagagcaca aggtcggata    3600
accagtgggc ctgccggctt ggctgcctgg ccctcccct gccgagacaa acggctggag    3660
ggaggaagtg tgcggctggg aagctccgct gctctggccc gggtttccca tttccccctt    3720
cccgcgctga gacggcgagg aaagttagcc cggaaatctg cgcccgccta aaacccggcc    3780
tggtcccagc caccgcccca ggaacttccc ccaccgcagg ggcggaggtc gagagcaggg    3840
atggagaagt ggacctgcgc gggtggactc cggggcgcgg gtggactccg gggcgcgggg    3900
ggactccgag gagcgggtgg actgtggggc gcgggtaccg tctcgcagcg acctctgtcg    3960
gcggctctgg ggatggcccg catctgtctg cgtgtacctg gtatacgtgc aggtacatgt    4020
tcctgttcac gtgcagactg ggcggggat ggggggtcc acaccggtgt acacctttgc    4080
atacctctta gcaacttgaa attccaccac gagagatatc tttattccgc tattcctgtg    4140
catctgcacg gagcccctag gccatagat ttgtgtgcaa atgaaatgag gatgtagtct    4200
gggtgcccaa ggggggtgc cttgagtgtg gttgtctgta tgcctccctg agggtatttc    4260
actttctgct cccatccgcc cctatgagcg agtacctatg agcacaggat gtgcacatat    4320
ttgagtctta ttagtggtac acgcagtttt atcatctccc caggtctgtg tctgtatgaa    4380
atgtgcatgg gtgtgtgtgt gcacgcgtgt gttcccactc ggggaatgtg gggagaggtg    4440
catggagcca agatgggtgg taaatagtat gtttctgaaa ttaaaggact aatgtggagg    4500
aaggcgcccc agatgtacta aacccttgc ccttcatctc atcctctctg acttgggaag    4560
aaccaggatt ttgtttttaa gcccttgggc atacagttgt tccatcccga catgaactca    4620
gcctcccgtc tgaccgcccc ttggccttcc ttcttcctcg atctgtggaa cccagggaat    4680
```

```
ctgcctagtg ctgtctccaa gcaccttggc catgatgtaa acccagagaa attagcatct    4740
ccatctcctt ccttattccc cacccaaaag tcatttcctc ttagttcatt acctgggatt    4800
ttgatgtcta tgttccctcc tcgttattga tacacacaca gagagagaca aacaaaaaag    4860
gaacttcttg aaattccccc agaaggtttt gagagttgtt ttcaatgttg caacaagtca    4920
gtttctagtt taagtttcca tcagaaagga gtagagtata taagttccag taccagcaac    4980
agcagcagaa gaaacaacat c                                              5001
```

<210> SEQ ID NO 27
<211> LENGTH: 5001
<212> TYPE: DNA
<213> ORGANISM: Homo sapiens

<400> SEQUENCE: 27

```
acttgcaagc taagtgaaaa tgggctcatg tatgagaatg ttcgtgttag acattttttg      60
tgttagacaa aaactagaaa caaaccaaat ccccatcaac agaatatatt agaatatatt     120
gatacaatag aatattacat cataattttt tttaaaaaca ttactgatac atacaaccac     180
gtatatgaat ctcacaaaca taatgctgac tgaagaagt caaacagaaa tgagtacatt      240
ctgtgtgatt tcatttatat gatgccccaa accaggagga aataatctat ggtgataaaa     300
gtgagagagt ggttggttat cttggaggg tatcagcagg gagggggcat gagggaacct      360 gctgggggacc tgaaaatacg tggagctggg tggtggctac atacagatgg aaaaattcat    420
cagctgtaca cttaagaggt gtccacctca tacctaagtt acatatcaat aaaaaggaaa    480
aaaattttgg aaacttttt tttttttttt tgagacagag tcttgctctg tcccccaggc     540
tggaatacag tggtgcgatc ttgactcact gcagcctccg cctcccaggt tcaaataatt    600
ctccagcctc agcctcccga gtagctggga ctgcagatgc gcaccagcac gcctggctaa    660
tttttgtatt tattatagag atggggtttc accatgttgg ccagctggtc tcaaactcct    720
gacctcaagt aatccgccca cctcagactc ccaaagtgcc aggattacag gtgtgagcca    780
ctgcaccagg cctggaacaa ttttaaaata atgtattggc tctgcaaatg cagcttcaga    840
acaagtccct tagctgtccc caccccaccc taagtcacca cccttaagcc tcacccatgt    900
ggaattctga aacttccttt gtagaaaact ttggaaggtg tctgccacat tgatcctgga    960
atgtgtgttt atttggggtt atataaatct gttctgtgga agccacctga agtcaggaag   1020
agatggaggg catccttcag gagtgagatg agacctcatc atacttgact gtccagcatc   1080
atctctgagt aaggggacca aaaaatttat cttccaaact aggacacttt caagagtgga   1140
agggggatcc attaatattt tcacctggac aagaggcaaa caccagaatg tccccgatga   1200
aggggatata taatgaccct tcttgatgtg aaacctgcca gatgggctgg aaagtccgta   1260
tactgggaca agtatgattt gagttgtttg ggacaaggac aggggtacaa gagaaggaaa   1320
tgggcaaaga gagaagcctg tactcagcca agggtgcaga gatgttatat atgattgctc   1380
ttcagggaac cgggcctcca gctcacaccc cagctgctca accacctcct ctctgaattg   1440 actgtcccctt ctttggaact ctaggcctga ccccactccc tggccctccc agcccacgat   1500
tcccctgacc cgactccctt tcccagaact cagtcgcctg aacccccagc ctgtggttct   1560
ctcctaggcc tcagcctttc ctgcctttga ctgaaacagc agtatcttct aagccctggg   1620 ggcttcccg ggccccagcc ccgacctaga acccgcccgc tgcctgccac gctgccactg   1680
ccgcttcctc tataaaggga cctgagcgtc cgggcccagg ggctccgcac agcaggtgag   1740
gctctcctgc cccatctcct tgggctgccc gtgcttcgtg ctttggacta ccgcccagca   1800
```

```
gtgtcctgcc ctctgcctgg gcctcggtcc ctcctgcacc tgctgcctgg atccccggcc    1860
tgcctgggcc tgggccttgg tgggtttggt tttggtttcc ttctctgtct ctgactctcc    1920
atctgtcagt ctcattgtct ctgtcacaca ttctctgttt ctgccatgat tcctctctgt    1980
tcccttcctg tctctctctg tctccctctg ctcaccttgg ggtttctctg actgcatctt    2040
gtccccttct ctgtcgatct ctctctcggg ggtcgggggg tgctctctcc cagggcggga    2100
ggtctgtctt ccgccgcgtg cccgcccccg ctcactgtct ctctctctct ctctctttct    2160
ctgcaggttc tccccatgac accacctgaa cgtctcttcc tcccaagggt gtgtggcacc    2220
accctacacc tcctccttct ggggctgctg ctggttctgc tgcctggggc caggtgagg     2280
cagcaggaga atgggggctg ctggggtggc tcagccaaac cttgagccct agagccccc     2340
tcaactctgt tctcccctag gggctccctg gtgttggcct cacaccttca gctgcccaga    2400
ctgcccgtca gcaccccaag atgcatcttg cccacagcac cctcaaacct gctgctcacc    2460
tcattggtaa acatccacct gacctcccag acatgtcccc accagctctc ctcctacccc    2520
tgcctcagga acccaagcat ccacccctct cccccaactt cccccacgct aaaaaaaaca    2580
gagggagccc actcctatgc ctcccctgc catcccccag gaactcagtt gttcagtgcc     2640
cacttcctca gggattgaga cctctgatcc agacccctga tctcccaccc ccatccccta    2700
tggctcttcc taggagaccc cagcaagcag aactcactgc tctggagagc aaacacggac    2760
cgtgccttcc tccaggatgg tttctccttg agcaacaatt ctctcctggt ccccaccagt    2820
ggcatctact tcgtctactc ccaggtggtc ttctctggga aagcctactc tcccaaggcc    2880
acctcctccc cactctacct ggcccatgag gtccagctct tctcctccca gtaccccttc    2940
catgtgcctc tcctcagctc ccagaagatg gtgtatccag ggctgcagga accctggctg    3000
cactcgatgt accacggggc tgcgttccag ctcacccagg agaccagct atccacccac     3060
acagatggca tccccaccct agtcctcagc cctagtactg tcttctttgg agccttcgct    3120
ctgtagaact tggaaaaatc cagaaagaaa aaataattga tttcaagacc ttctccccat    3180
tctgcctcca ttctgaccat ttcagggtc gtcaccacct ctcctttggc cattccaaca     3240
gctcaagtct tccctgatca agtcaccgga gctttcaaag aaggaattct aggcatccca    3300
ggggaccaca cctccctgaa ccatccctga tgtctgtctg gctgaggatt tcaagcctgc    3360
ctaggaattc ccagcccaaa gctgttggtc tgtcccacca gctaggtggg gcctagatcc    3420
acacacagag gaagagcagg cacatggagg agcttggggg atgactagag gcagggaggg    3480
gactatttat gaaggcaaaa aaattaaatt atttatttat ggaggatgga gagagggaa     3540
taatagaaga acatccaagg agaaacagag acaggcccaa gagatgaaga gtgagagggc    3600
atgcgcacaa ggctgaccaa gagagaaaga agtaggcatg agggatcaca gggcccaga    3660
aggcagggaa aggctctgaa agccagctgc cgaccagagc cccacacgga ggcatctgca    3720
ccctcgatga agcccaataa acctcttttc tctgaaatgc tgtctgcttg tgtgtgtgtg    3780
tctgggagtg agaacttccc agtctatcta aggaatggag ggagggacag agggctcaaa    3840
gggagcaaga gctgtgggga gaacaaaagg ataagggctc agagagcttc agggatatgt    3900
gatggactca ccaggtgagg ccgccagact gctgcagggg aagcaaagga gaagctgaga    3960
agatgaagga aaagtcaggg tctggagggg cggggtcag ggagctcctg ggagatatgg     4020
ccacatgtag cggctctgag gaatgggtta caggagaccc ctggggagat gtgaccacag    4080
caatgggtag gagaatgtcc agggctatgg aagtcgagta tggggacccc cccttaacga    4140
```

| | |
|---|---|
| agacagggcc atgtagaggg ccccagggag tgaaagagcc tccaggacct ccaggtatgg | 4200 |
| aatacagggg acgtttaaga agatatggcc acacactggg gccctgagaa gtgagagctt | 4260 |
| catgaaaaaa atcagggacc ccagagttcc ttggaagcca agactgaaac cagcattatg | 4320 |
| agtctccggg tcagaatgaa agaagaaggc ctgccccagt gggtctgtg aattcccggg | 4380 |
| ggtgatttca ctccccgggg ctgtcccagg cttgtccctg ctaccccac ccagcctttc | 4440 |
| ctgaggcctc aagcctgcca ccaagccccc agctccttct ccccgcaggg acccaaacac | 4500 |
| aggcctcagg actcaacaca gcttttccct ccaaccccgt tttctctccc tcaaggactc | 4560 |
| agctttctga agccctccc agttctagtt ctatcttttt cctgcatcct gtctggaagt | 4620 |
| tagaaggaaa cagaccacag acctggtccc caaaagaaat ggaggcaata ggttttgagg | 4680 |
| ggcatgggga cggggttcag cctccagggt cctacacaca aatcagtcag tggcccagaa | 4740 |
| gacccccctc ggaatcggag cagggaggat ggggagtgtg aggggtatcc ttgatgcttg | 4800 |
| tgtgtcccca actttccaaa tcccgcccc cgcgatggag aagaaaccga gacagaaggt | 4860 |
| gcagggccca ctaccgcttc ctccagatga gctcatgggt ttctccacca aggaagtttt | 4920 |
| ccgctggttg aatgattctt tccccgccct cctctcgccc cagggacata taaaggcagt | 4980 |
| tgttggcaca cccagccagc a | 5001 |

<210> SEQ ID NO 28
<211> LENGTH: 5001
<212> TYPE: DNA
<213> ORGANISM: Homo sapiens

<400> SEQUENCE: 28

| | |
|---|---|
| aatgcaagaa ctaatgcacc tatcatgata gttttgacac ctgttgcaat acttttaaat | 60 |
| aaagccttcc ttactgttat accaagtgtc agaataaatt tttctttacc agatccttaa | 120 |
| attaaggcag tacaatcaac actgcagcat actctggtga cctacaacat aaaaggcatg | 180 |
| aaccagctgg caagtcaggt gactcagggt cttttgtcat ctcagtcctc atcctctaat | 240 |
| gccatggact ctcctcattt ctccagaagt gttccatttt ccacacccttt aataattcct | 300 |
| ttactttagt taacctttcc aggtgtgctc tccctgagct ctgagcctta gttcattggt | 360 |
| ttagctctga tttagttcat gtctgtagcc tgacaatgac ttgttctttc ttaaatttgt | 420 |
| gctacacagg tggaaatcta aagtatggtg catatttgat taaaagaata gtactatgta | 480 |
| gaattttaaa tggatagaaa tatatagggt ttatgaatac atttactggg gcaaacaaca | 540 |
| tgttttacaa atacactcat gtttatgata gtgtatcctc aagaagacaa aactagaata | 600 |
| taacgtatat actcctttac aaggagcata agtaaagcgg ggcccaattt cattgtaatg | 660 |
| ttgccatgag caaatggggc attacagtga aggagacaaa tggaaactga agagaaagac | 720 |
| tctgtcatta cataggcagg actctactag gaaaggattg actggtctat aaatcagctc | 780 |
| tggttcttat ggcccgaaat attcccagag agcatgtaag agctaagact tcagagttga | 840 |
| attttctgca tccaaactgt agctccaaaa cttaatagct tcctgtgctt tcattgtttc | 900 |
| ttttgtaaat ggggacaata gtaaaatctg tcactgtgtg ccttggtcag tgatatctcc | 960 |
| agtgaataaa tggggttagg gacatggtag atgttcagta aatacgaaaa acaaaagtat | 1020 |
| tctttattgg ctaagtgagc atcgattatg caagtgctaa aaacagtgtc tgactgaaaa | 1080 |
| taaagactgt ctagagttta gatatctcat tcctcttatt aacattatct ttattatata | 1140 |
| actctattaa gttggggaag tgtcctttga aattatcaag tctcttgttt cttattagaa | 1200 |
| atataacaag aaaaaaattg atctttggag tgtacttatc cactagtgga gagcttggtg | 1260 |

```
caatgaacac ttaactattt tccagagaga atattgcact ctctaaagtt tgcctttctt   1320
gtgtataaat gcttgcagtt ggtgtgtttg caagatgggc ttcagtaaat ctgaaaacac   1380
cctgtggacc aggagtaatt acttttcttc cagcccatac ttatttgcta cctttgacct   1440
atatcccttc taccattttg cttctgttct ttcccacccc ttaacctcca tcatggctgg   1500
gctgaatgca gctaaggtac attttgtcat tgttttttct tagtgggata ttacttccat   1560
ttacatttta atcacattta gatatatttt tgttttattt ttgtcccccat tcattagggt   1620 gcaaaaagtg acaattttttg cttttttatga aagagaaag aaagatatca tgtctggcat   1680
gctatggaaa acaactgtac aagtcattta tgttataaca tttacatctc attatgaaca   1740
tttaggacaa agatggtttc ctttagttgg atcagaatca acaaagaacc tctgaagttt   1800
ctttggaaat ttgaattttc atgcaaaaaa gtgttttttaa tcaaattgag gatatttttt   1860
caattgtgta ttctcattga gtatgatgct actcccaagg gtgtaaaagt gtagttcttg   1920
agagtgggaa caaatcttac agatttaaat gatttgtggc ccttcaaagt tcaaccctat   1980
ctaacaaagt cttattcctt agtttttttgt tttctcccca ttgggttttc ttgtgtatca   2040
catgagaagc attgacatta agttcatgga agatacacaa aatgtatata agttcagtgt   2100
tacaaaccta tggaaaatga gtggctgtga ttgcagtact ttccaaggct tactagatct   2160
cacagtcata tcaagagatg tgtcctctgc atacatatgt tttgtcactg gccatcttat   2220
agttgttgct tatttttgat ccttagcatt tctaactgtg ttgtgggctt tgaggataat   2280 ttatattttta ttaattctac aaaaattgtt cagcacatca ataattaggt caagcatcga   2340 agaaaaagt cttgacaata tttaggtgac tagcagctag tgaagttaaa aaatttcaca   2400
catgcaacaa aattaaaagt taagtacaac cctgccacag aggccgggag aggcgactgg   2460 cccttttgttg gtctgtgaga aatcaaactt ccaacatgac aagcaggaag cctgcggtta   2520
agggagtcag cgtgtcacaa atacaagcac ctggggtctt ccaagagcat catacctcct   2580
ccagcccctg gagccacctg ctttcctaac tggctgtggg aaatggcctg aggtcccaga   2640
tgctgccact gtgctgctgc cttccactct ctccaagcag agcgcaagtt cagccacctt   2700
tgaaagacac ccaccccctg gcctggggat gcacaagttc agagctttgc agggagtaac   2760
catgggttat ggcttcatga aaatgtccta ctcaccagtg ccttttttcgc agatgtggat   2820 gtggaggcat gagggagggt aattattgga ttaccaaggt gctgctaaga gcagaggagg   2880
aaacccctat tcccagtcat atgtctggtg tgacatttca ctaacccatt taagtgcaca   2940
ggcctccaaa tatctaccta atgagtatga tggtttgggc attttacact taaaatcact   3000
ggcctcatgt caactgaagc ctgactggcc agtgtctcaa agtcacagat gatgacctga   3060
tccctcagga acagatggtg tttcagcttt gtgggagtga ctgtcaaggt atggagcact   3120
taggtggtct ttgaaaccctg tcaggtttca catctctgct ttgagtgaaa agctcatcac   3180
ccacagtagt gaggaatgtg cctatacttg ctggggctga tctgttgaaa ctttatgtgt   3240
agacaatgga acatccagg agcatttctg ctttcatgta gcctcttaat aattgatgtc   3300
cctgaagtcc tgtgtcctca gggacagttc ctctgattcc tggattgtac cagctttcat   3360
gatgttaaat ctaatctgta aaactctgag cattaatctc catgaaaata agaccttgtt   3420
ctttctcatt taaatgcccc ttttttttct tgtctaatat tctgagtagg atttccagta   3480
ctgtgttgaa agaagtagtg agagtgggca tccttatctt ataataaatc tcagaaaaaa   3540
gattccaaca tttcaccact gactatagtg ttagctaatg gcttatctta tagctaataa   3600
```

```
ggaatgtgtc tctttattct gaggtatatt ctttatatac ctaatttgtt ataaattgta   3660
ttagagatgg attttaaatt ttgtcaaaat aattttaggc atgcataaaa atagttatga   3720
tttttaatct tttattgtgt aaataaggag tatggcattt attgattcca acatattaaa   3780
atattcttgc atcccaggaa taaatcaagc ttgatcataa taaatgatcc ttttatagtg   3840
cttttgaatt tcatttgcaa ctactttgtg gatgattttg catctgtgtt catcaggaat   3900
attggctgta attttttttt ttcttgtaat gtccatctct ggcttaggta tcaaggtaat   3960
gctggcttca taaatgagt ttgggagtat tcctccttaa ttttttcaaa gatttggttc   4020
tgtttaaatg tttggtgaaa ttcaggagta atcagatcta aaaaaacgta agaacactaa   4080
aaataaatga taaaaatatt ttaaagttttt aagtgtttat cactttcaaa taattttaa   4140 gtattcatta cttagaaaat gtttatctat aaacattaga aaatgtttat aatttgttaa   4200
tttgcttatg taatttgata cactacaatt tatttgtttg tttgtttttt gaaacagagt   4260
ctcactctga cacccaggct ggagtgcagt ggcacaatct cggctcactg caacctccac   4320
ctcatgagtt caaggaattc cctgcctcgg cctcctgagt agctgggatt acaggtgcac   4380
acaaccatgc ctagctaatt ttttttttgt ttttttttg ttttttcgt tgagatgggg   4440 tttcaccgtc ttggccaggc tggtcttgaa ctcctgacct cgtgatccac ccacctcgga   4500
ctcccaaagt gctgggatta caggcgtgag ccacctcgcc aggcctacag tacaatttat   4560
atcagtaaat aaattacgtt gaagtccata agcaaattta gttataaagt taagaaaaat   4620
ttgaatagat tttaaattta acttttagct taaattttc atttggttat ttttaaacct   4680
gcattgaata caaagattaa actttgtact ttttgattat agagatatac atatagtata   4740
taaatagata catattgtat ctgtgttatt aaattttcac ggtgggttca attaggaaaa   4800
agatatctaa aaagtctctg ggaacaagat ggggaagaca ataatgaaaa acaaaacatt   4860
tgagaaacac ggctctaaac tcatgtaaag agtgcatgaa ggaaagcaaa aacagaaatg   4920
gaaagtggcc cagaagcatt aagaaagtgg aaatcagtat gttccctatt taaggcatt    4980 gcaggaagca aggccttcag a                                              5001
```

<210> SEQ ID NO 29
<211> LENGTH: 5001
<212> TYPE: DNA
<213> ORGANISM: Homo sapiens

<400> SEQUENCE: 29

```
aggcacaaag caaagagcaa gccctcatca gacactgaat ctgctagggc cttagtcttg     60
gcttttccaa cctccagaac tataaaaaga aatgcttgtt gtctaaaagg cattcagtct    120
atggtgtttt gttagagcag ccccaagaga cttaagaggg aacaagaggg cgatttctgt    180
tgtgttgata atgtttagtt tgtggttaca aaagagtgca gacgttttta ttttataaca    240
attcattgag ctatatactt aagatgtatg cgtaattttc tatgtatatt attgttttat    300
aaactttttc ttaaaagagg aaatgggaat tctcccttt atgtattaat ctcttatgaa     360
agagtttgtt ggcttcccaa gatatttctg aaagattgct tttggcttca tttatgttct    420
gccactgctt atgcacctct caataactct tcatctgta taatttatca ttctttgata     480
gggaccctct tccttgaaaa ataattgaag atataaggag gaggaagaga agacaactaa    540 aatgttttatt tctagataca tagtagtcct gcatagataa ttatattcaa aagaggagga   600
caaattggct cctatctctg aaatttatag aaaagcattt ccacattaaa gtgatttcaa    660
atgactagaa atgtcattca agttttactt tctaaatgtc actctgtctc tccaaaccctc   720
```

```
attaaccaca aggaactggt gcagggactg gaagtagttt tctcatacaa cggaaagtta    780
acgaggggag gaaaggatgt gtgcaaaaat aacgtccaca gaagggacaa ataacaaagg    840
gaaagatgac aggaaagggt tcgggcacta acccttacaa tgcagataca cactgggctg    900
gtctaagaaa taggtttccc tggtagacag aaggttaaat aaattttcct ggttattctg    960
atacaactct aataaaagaa gagaaatgaa gctaaaactt aaaatgatgt atttaaaagg   1020
aagaaatttt aacccattca taggtgagct tctgccaaga ttactactaa tcctcaggag   1080
aaggggtaga ggagaaactc cataaaggca actggaagtg gagtattagg aagcacctca   1140
agaacacaat agcaggaagt agctagagaa caaagagaag aaaccagaaa aaaaaaatcc   1200
cttttattt ttctgtttcc attcctttgg ctccatttcc acagctatgg cctttatttt   1260
caccctccac agccatgaga gcctctgggc aggagttctc ctcgcctctc cctgttccaa   1320
tcacctctaa catttctgcc tattgttctg cccagggaaa aaactccagt ctcttctctg   1380
tcaaagacct cttgaattaa gtccaaatgc tacactctgg cattcaagac tccgtaatac   1440
agctcaacct gacttttcca ccctcagcct ccttgattcc taaaatgaag cctgtccaca   1500
attgaagctc cttgtctttg ctcctgcaaa cttgttcatt ctcctggctg tgtttgtgct   1560
ggtctctgtc tatctagagc tgtggatatc atggtatcta ttgtctatca tgctagccat   1620
gaaccacatg tggctggtga gcattttata tggtactagt ctaaattgac atctactgtg   1680
agtgtaaaaa tgtgcattat gttttgaaga ctgtacacaa aatttaatta tctcatgaat   1740
aattttagat tggttatatg ttgaaattat aatattttgg atatactatg ctaaataaaa   1800
catattatta aaattaactt cacctgtttc ttttcctctt tcaatatggc tactagagct   1860
ttttaaattg cattatgtga ctttattgga cagtaccgat tgaatgccct caaccacatc   1920
acctcaccac agccacctct acctgtagtg atcataccac ttctttaggc acactgcctg   1980
cattaagggc aatgaatgcc ttttcatctt ctccactaga tgtagtttct ttttctttg    2040
agagccatca tcaccatcat ggttgacacc atgaacctat ctgaagatgt cagccataga   2100
ctgcttgata ttctacagga aagatcacag ttttaagtgc aatctaccca tgttattagc   2160
agtgtgtatc tttcacacat tacacagcct ctctaagcct catttctctc ctctgtaaga   2220
tggggatgat aataacccat ctcaaatgtt tactatgagg attattcaaa gaatggcaaa   2280
tagcaagtgc ttaataaatg ataactagta ctaccgccac tactgttgtt tttattgtat   2340
tagattatga actctctaag gaccatttcc ggatggagga taagagacca tttgatgtgg   2400
gcagtgatga ggccttctgt tgcacctgga aaggtcaact atatacaagc ctgcaagtca   2460
ttctatagga gcaggcccca gtgaccagac tctatagact gtctcctctt tcctgagagg   2520
gacagccatc tctaggttga ctaacctctg aagctccttg cattggcttt tgtgctatga   2580
gccatggatg attccagact aatccgagaa tgctcgtcaa aaccccaagg aattactcaa   2640
atactgacat aacagacatt tttgagtgga agagccgagt tttttttaat attctgaaac   2700
tcattgtttt taaaatgcat gagatggcca aggtcttgct aagagctggc ctgcaaaggc   2760
caaaaggcca gagagaatga aacccataga gaggcagaat aaccagaaag gttgggactc   2820
gtttatttta taatgtaaat tagtctatta tgaaacaata cttgtttact ggtggaaaat   2880
tggaaaatac aaagaataaa aggaggaaaa aaatcactct ttagtttcac aagccaaatc   2940
aagccactat taaaatggtg gtttacttcc tttattaat tttctctaca tatttttgca    3000
taatcatgtt gtatgtacaa ttttatgttc tatttttcaa tattaactgg tgtctttcaa   3060
```

-continued

| | |
|---|---|
| atttcctaat gacaaaaata atatatgctc ataatagaac attttaaatg caaataaaac | 3120 |
| aaaataaatg ttaaaattta gtaatattta ttaaattttc tccaagtgca cgaaattaca | 3180 |
| aatgtaacaa cctaattccc tagtggccta ataccctat ttcccagacc tcttctcatt | 3240 |
| acaaggaaaa actcatatgc agatagttct aaaggtatga agtgaaaaga taaagatttt | 3300 |
| tcttccttgc tgcatcctca ccccatcagc attattcccc agggtaacta ctattaatag | 3360 |
| atagtaattc tacccaaagg aaaaaatcat atgcatataa cagcatcata tgtataccctt | 3420 |
| tctagtaact tacaaaacaa atgataatat catatccttt cttatgtgta ttgctctttt | 3480 |
| cactaaatgt atctgtgata tgtgtctata tcagctgatt gtccttttg atggctgaat | 3540 |
| aatattccat cttgtccacg tgatagtatt acttgacaag ctccctgctg atggacattt | 3600 |
| gtctttgtta ctatgatagt aatataatca acatttatat atgttttgta tgtatctata | 3660 |
| atacacatgc acatacacat gcatatttct gcagggatag ccatagtaaa taactagtaa | 3720 |
| cggtattgca agtaaaagga acaatctcat tgcttgaaat tttaaatttt gaaatacact | 3780 |
| gccaattttc atggtctctc cttgtaagct agtttgggct ttctcacagc atgacaggct | 3840 |
| cagggcagtc agaccatcct ggccaaagag cagagtgcca cagaccacaa ctgcttctaa | 3900 |
| tcagccatct tcccaaagcc ttctctttt tctattaata actttgtatg agattccatc | 3960 |
| ttaatacttt tctgttgttt ggtcttgtaa gagcttattt ttcctgaacc aggaagtggt | 4020 |
| tcagggcggt ttttctaact tcacagagct ccctcttctg ttagcttttg tgaaatggtc | 4080 |
| aaaaacatag cagcctgcct tctgagttct ccatcccacc ctggttgggc cttctctatc | 4140 |
| cttgtctgtg ttgtttatat cctgctgaag tgtgattcca cttgtggcag tttctcctct | 4200 |
| gtgtaggatc aaaagggctg tgactggttg gtttgaaaat ttcttatacc ctagactatt | 4260 |
| ccagtgcctt tcagaagttt ccaaggcccc ctcacactaa tctattatca tattgggcaa | 4320 |
| aactccttgc agtttcagct actattccct gattgacttt tcagtaaatc tatctctcag | 4380 |
| tctttcagta tccaaagaag attggttcta ggaccaccat cccgctgcct ccacagatac | 4440 |
| caaaatcaga ggatgctcaa ttccctctta taaaacgttg cagtatttgc atataatctg | 4500 |
| cacatgtatt tctgtatatt ttaaatcatc cctagattac ttataatacc tgatacaata | 4560 |
| taaatgctaa atagctgtaa cactgtatct ttaaaattta cattatttt tgttgttgta | 4620 |
| ttattatttt tattgtattt ttaaaaaata ttttccatct acagtcagta gaatccacgg | 4680 |
| atacagaacc tatggatagg aaggaccaac tgtatctttt agtgttttga ggttcttgaa | 4740 |
| ttctcaggtc gtttgctttc ctttgctttc tcccaagtct tgttttacaa tttgctttag | 4800 |
| tcattcactg aaactttaaa aaacattaga aaacctcaca gtttgtaaat ctttttccct | 4860 |
| attatatata tcataagata ggagcttaaa taaagagttt tagaaactac taaaatgtaa | 4920 |
| atgacatagg aaaactgaaa gggagaagtg aaagtgggaa attcctctga atagagagag | 4980 |
| gaccatctca tataaatagg c | 5001 |

<210> SEQ ID NO 30
<211> LENGTH: 711
<212> TYPE: DNA
<213> ORGANISM: artificial
<220> FEATURE:
<223> OTHER INFORMATION: coding sequence of mOrange

<400> SEQUENCE: 30

| | |
|---|---|
| atggtgagca agggcgagga gaataacatg gccatcatca aggagttcat gcgcttcaag | 60 |
| gtgcgcatgg agggctccgt gaacggccac gagttcgaga tcgagggcga gggcgagggc | 120 |

```
cgcccctacg agggctttca gaccgctaag ctgaaggtga ccaagggtgg cccctgccc      180 ttcgcctggg acatcctgtc ccctcagttc acctacggct ccaaggccta cgtgaagcac     240
cccgccgaca tccccgacta cttcaagctg tccttcccg agggcttcaa gtgggagcgc     300
gtgatgaact tcgaggacgg cggcgtggtg accgtgaccc aggactcctc cctgcaggac    360
ggcgagttca tctacaaggt gaagctgcgc ggcaccaact tccctccga cggccccgta    420 atgcagaaga gaccatggg ctgggaggcc tcctccgagc ggatgtaccc cgaggacggc    480
gccctgaagg gcgagatcaa gatgaggctg aagctgaagg acggcggcca ctacacctcc   540
gaggtcaaga ccacctacaa ggccaagaag cccgtgcagc tgcccggcgc ctacatcgtc   600
ggcatcaagt tggacatcac ctcccacaac gaggactaca ccatcgtgga acagtacgaa   660
cgcgccgagg ccgccactc caccggcggc atggacgagc tgtacaagta g             711
```

<210> SEQ ID NO 31
<211> LENGTH: 1428
<212> TYPE: DNA
<213> ORGANISM: artificial
<220> FEATURE:
<223> OTHER INFORMATION: coding sequence for tandem-d-Tomato

<400> SEQUENCE: 31

```
atggtgagca agggcgagga ggtcatcaaa gagttcatgc gcttcaaggt gcgcatggag    60
ggctccatga acggccacga gttcgagatc gagggcgagg cgagggccg cccctacgag    120 ggcacccaga ccgccaagct gaaggtgacc aagggcggcc ccctgccctt cgcctgggac   180
atcctgtccc ccagttcat gtacggctcc aaggcgtacg tgaagcaccc cgccgacatc   240
cccgattaca gaagctgtc cttccccgag ggcttcaagt gggagcgcgt gatgaacttc   300
gaggacggcg gtctggtgac cgtgacccag gactcctccc tgcaggacgg cacgctgatc   360
tacaaggtga agatgcgcgg caccaacttc cccccgacg gccccgtaat gcagaagaag   420
accatgggct gggaggcctc caccgagcgc ctgtacccc gcgacggcgt gctgaagggc   480
gagatccacc aggccctgaa gctgaaggac ggcggccact acctggtgga gttcaagacc   540
atctacatgg ccaagaagcc cgtgcaactg cccggctact actacgtgga caccaagctg   600
gacatcacct cccacaacga ggactacacc atcgtggaac agtacgagcg ctccgagggc   660
cgccaccacc tgttcctggg catggacacc ggcagcaccg cagcggcag ctccggcacc   720 gcctcctccg aggacaacaa catggccgtc atcaaagagt tcatgcgctt caaggtgcgc   780
atggagggct ccatgaacgg ccacgagttc gagatcgagg gcgagggcga gggccgcccc   840
tacgagggca cccagaccgc caagctgaag gtgaccaagg gcggccccct gcccttcgcc   900
tgggacatcc tgtcccccca gttcatgtac ggctccaagg cgtacgtgaa gcaccccgcc   960
gacatccccg attacaagaa gctgtccttc cccgagggct tcaagtggga gcgcgtgatg   1020
aacttcgagg acggcggtct ggtgaccgtg acccaggact cctccctgca ggacggcacg   1080
ctgatctaca aggtgaagat gcgcggcacc aacttccccc ccgacggccc cgtaatgcag   1140
aagaagacca tgggctggga ggcctccacc gagcgcctgt accccgcga cggcgtgctg   1200 aagggcgaga tccaccaggc cctgaagctg aaggacggcg ccactacct ggtggagttc   1260 aagaccatct acatggccaa gaagcccgtg caactgcccg gctactacta cgtggacacc   1320
aagctggaca tcacctccca caacgaggac tacaccatcg tggaacagta cgagcgctcc   1380
gagggccgcc accacctgtt cctgtacggc atggacgagc tgtacaag              1428
```

<210> SEQ ID NO 32
<211> LENGTH: 720
<212> TYPE: DNA
<213> ORGANISM: artificial
<220> FEATURE:
<223> OTHER INFORMATION: coding sequence for superfolder GFP

<400> SEQUENCE: 32

```
atgcgtaaag gcgaggagct gttcactggt gtcgtcccta ttctggtgga actggatggt      60
gatgtcaacg gtcataagtt ttccgtgcgt ggcgagggtg aaggtgacgc aactaatggt     120
aaactgacgc tgaagttcat ctgtactact ggtaaactgc cggtaccttg gccgactctg     180
gtaacgacgc tgacttatgg tgttcagtgc tttgctcgtt atccggacca tatgaagcag     240
catgacttct tcaagtccgc catgccggaa ggctatgtgc aggaacgcac gatttccttt     300
aaggatgacg gcacgtacaa aacgcgtgcg gaagtgaaat ttgaaggcga tacccctggta     360
aaccgcattg agctgaaagg cattgacttt aaagaagacg gcaatatcct gggccataag     420
ctggaataca attttaacag ccacaatgtt tacatcaccg ccgataaaca aaaaaatggc     480
attaaagcga attttaaaat tcgccacaac gtggaggatg gcagcgtgca gctggctgat     540
cactaccagc aaaacactcc aatcggtgat ggtcctgttc tgctgccaga caatcactat     600
ctgagcacgc aaagcgttct gtctaaagat ccgaacgaga aacgcgatca tatggttctg     660
ctggagttcg taaccgcagc gggcatcacg catggtatgg atgaactgta caaatgatga     720
```

<210> SEQ ID NO 33
<211> LENGTH: 720
<212> TYPE: DNA
<213> ORGANISM: artificial
<220> FEATURE:
<223> OTHER INFORMATION: coding sequence for mVenus

<400> SEQUENCE: 33

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct gatctgcacc accggcaagc tgcccgtgcc ctggcccacc     180
ctcgtgacca ccctgggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca ccgccgacaa gcagaagaac     480
ggcatcaagg ccaacttcaa gatccgccac aacatcgagg acggcggcgt gcagctcgcc     540
gaccactacc agcagaacac ccccatcggc gacggccccg tgctgctgcc cgacaaccac     600
tacctgagct accagtccaa gctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 34
<211> LENGTH: 711
<212> TYPE: DNA
<213> ORGANISM: artificial
<220> FEATURE:
<223> OTHER INFORMATION: coding sequence for mNeonGreen

<400> SEQUENCE: 34

```
atggtgagca agggcgagga ggataacatg gcctctctcc cagcgacaca tgagttacac      60
```

```
atctttggct ccatcaacgg tgtggacttt gacatggtgg gtcagggcac cggcaatcca    120
aatgatggtt atgaggagtt aaacctgaag tccaccaagg gtgacctcca gttctccccc    180
tggattctgg tccctcatat cgggtatggc ttccatcagt acctgcccta ccctgacggg    240
atgtcgcctt tccaggccgc catggtagat ggctccggat accaagtcca tcgcacaatg    300
cagtttgaag atggtgcctc ccttactgtt aactaccgct acacctacga gggaagccac    360
atcaaaggag aggcccaggt gaaggggact ggtttccctg ctgacggtcc tgtgatgacc    420
aactcgctga ccgctgcgga ctggtgcagg tcgaagaaga cttaccccaa cgacaaaacc    480
atcatcagta cctttaagtg gagttacacc actggaaatg caagcgcta ccggagcact    540 gcgcggacca cctacacctt tgccaagcca atggcggcta actatctgaa gaaccagccg    600
atgtacgtgt tccgtaagac ggagctcaag cactccaaga ccgagctcaa cttcaaggag    660
tggcaaaagg cctttaccga tgtgatgggc atggacgagc tgtacaagta a             711
```

```
<210> SEQ ID NO 35
<211> LENGTH: 57
<212> TYPE: DNA
<213> ORGANISM: artificial
<220> FEATURE:
<223> OTHER INFORMATION: ER localisation sequence

<400> SEQUENCE: 35
atggagtgga gctggatctt cttgttcttg ctcagcggca ctgcaggtgt tcactcc       57
```

```
<210> SEQ ID NO 36
<211> LENGTH: 12
<212> TYPE: DNA
<213> ORGANISM: artificial
<220> FEATURE:
<223> OTHER INFORMATION: ER retention sequence

<400> SEQUENCE: 36
catgacgagt tg                                                          12
```

```
<210> SEQ ID NO 37
<211> LENGTH: 74
<212> TYPE: DNA
<213> ORGANISM: artificial
<220> FEATURE:
<223> OTHER INFORMATION: WAK1 ER localisation sequence

<400> SEQUENCE: 37
atgaaggtgc aggagggttt gttcttggtg gctattttct tctcccttgc gtgtacgcag    60
ctggtgaagg ggca                                                        74
```

```
<210> SEQ ID NO 38
<211> LENGTH: 5268
<212> TYPE: DNA
<213> ORGANISM: Arabidopsis thaliana

<400> SEQUENCE: 38
ccactttttt gattgaccaa aggaagaaga agaagaagaa gaagaatctg aagagagcga    60
tgaagcatat tttcaagaag ctacacagag gtgggaatca agagcagcag aatcgaacca    120
acgatgcagc tcctccatcg gatcaaaatc ggattcacgt ttctgctaat cctcctcaag    180
caaccccttc gtcagtcact gagacgcttc cggtggccgg agctacttct tctatggcct    240
ctcctgctcc aaccgctgct tcgaaccgtg cggattacat gtcttctgag gaggagtatc    300
```

```
aagtgcagtt agccctagcg atcagtgctt cgaattcgca gtccagtgag gatccggaga    360
agcatcagat ccgagcggcg acgcttctga gcttaggaag ccatcaacgg atggattcaa    420
ggagggattc atcggaggtg gtagcccaga ggttatcgag acagtactgg gtaagttttc    480
tcttttata tctagggaaa tgctggattc tctctttgtg tttatcgact cttgggtcat    540
aatgacttca aggtacgccg agcttgataa gagccgaatt tagcatgtca tgattgttgg    600
gattcttatt agctaattga atttcattac ttctttactg atccatatgc caagtaaatt    660
tctttctggt gattttttg gttgttgttg cacctgcttg gttttataca gctttgtttc    720
ctctctgacg attcagccaa agcttttata gaaagttttg ccgttttac actgcctaca    780
tgattttaca tgaataataa cttgtagtaa actatttcta ggaatatggc gtgcttgact    840
atgaggagaa agttgtcgat agtttctacg acgtatacag tctatccaca gactccgcaa    900
agcagggaga aatgccatcg ctggaagatc ttgaaagcaa tcatggcaca cctggctttg    960
aagctgtagt tgtaaatcga cctattgatt cttccctgca tgagttgcta gaaatcgcag   1020
agtgtattgc actgggttgt tctactacca gtgttagtgt gttggtacag aggctggctg   1080
agcttgtcac cgagcatatg ggtggatctg cggaagattc cagtatagta ttggcaaggt   1140
ggactgaaaa aagcagcgag ttcaaggcag cattgaatac ttgcgtattc cctattggat   1200
ttgtaaagat tggtatctca aggcatcgtg ctctgctttt caaggtatat tctcaaaccc   1260
tcttcctaga tttagtctct tgtcttatcc tacttgtggc aagtcatgaa atcgttgaat   1320
gattggacca gctagtaaaa agaaggaaac atgaaatctc atatgttaag gatgattgaa   1380
caaatgactt gtgctgtttt cgcagaatca gatgctttgc tgcttgtact cataaatctt   1440
gtttgatttt gaaaactgat ccgtgggcag tttacttctc ccaatgtagg ttttggcaga   1500
tagtgtcagg ttaccttgta ggttggtaaa aggtagccac tacacaggca atgaggatga   1560
tgctgtgaac acgataagac tggaagatga aggtgttttt tgtttatctt tttcactatg   1620
attccattat tttctttttt cttttacga aaatgtaaca tatctcccct tctttcagag   1680
agtacttggt tgatcttatg acagatcctg ggacgcttat acccgctgat tttgcaagtg   1740
ctagtaataa caccgttgag ccatgtaact caaatggaaa caaatttcct acagctcagt   1800
tttcaaatga cgtgccaaag ctctcagaag gtgaaggaag tagtcacagt tctatggcca   1860
actatagttc ttcttttggat agaaggacag aggctgaaag gacagattct tcatacccaa   1920
aggtgggacc acttcggaac atagactata gttctccttc tagcgtaact agttctactc   1980
agttggagaa caattcctca acagcaattg gaaaggggag tcgaggagcc ataattgaat   2040
gttcaagaac aaacatgaat atagttcctt acaatcagaa cagtgaggaa gacccaaaaa   2100
accttttcgc agaccttaat ccatttcaaa ataaggagc tgacaagctg tatatgccca   2160
ctaaatcagg tttgaataac gttgatgatt ttcatcaaca gaaaaataat cctctggttg   2220
gtagatcacc tgcgccaatg atgtggaaga attacagttg caatgaagcc ccaaagagaa   2280
aggagaatag ttatatagaa aatcttctcc cgaaactcca ccgtgatcct cgttatggaa   2340
acactcaatc ctcatatgct acctcaagct ccaatggagc tatttcctca aatgtgcatg   2400
gcagagacaa tgtgacattt gtgtcaccgg ttgctgtacc atcatccttc acatccactg   2460
aaaatcagtt tagaccaagt atagtggagg atatgaacag aaacaccaac aatgaactag   2520
atcttcagcc tcatactgct gctgtggtac atggacaaca gaatgatgaa tctcacatcc   2580
atgatcacag aaagtacaca agtgatgaca tatccactgg ctgtgatccg aggcttaagg   2640
atcacgaaag tacaagttca tctcttgatt ctacatccta ccggaatgat cctcaagttc   2700
```

```
ttgatgatgc agatgttggt gaatgtgaaa ttccttggaa tgatctcgtt attgcggaga    2760
gaataggatt aggtaatgtg gcctgcagtt tatttgttta cgtgtttgaa agatttaact    2820
agttagtatc tattttcttt tctattttgg acggcagcta attattatct agtgggagca    2880
caattttata gcatagcccc ttttttacga tctacagttg cttattacaa gggatagctg    2940
tgcaataaac tttaggtagc atatagcttt tggagatcat atgtcctaat gcttatcttg    3000
ttttggttag ggtcctatgg agaggtctat catgctgact ggcatggcac ggttagtttt    3060
tcagaacctt acatttgatt tcattagagc tattgtagca acttgtatct gttattctct    3120
tccagaactt gccgctttag ttgcgttcac atttttagg gcttcaattg tgtcaaggag    3180
catgtatctg gcggttatct ggaacttcaa acattattaa cctgtcaaat tgttaatga    3240 gtgcaaagag ataaaatgca gcgcttaaat gcatgttttg tcattaaata ttcaaagcag    3300
tgtttgtgtt cttaaagtga aacagtttta aaaagcactt ttatatacgc ttgtttcagt    3360
cactagccac aaaaatgcat tagtgccctc catggtattg tctcacattc tctcatcaat    3420
attagctgtt gtcttttag tttatttagt gatagattat ttttggtgat ttaaactagc    3480
cttctgtgtc tgcccgtgct gtttatcttc acagaagtgg aaggtttcaa gtttatattt    3540
ctgcattttt gttatgattg gatttaggaa gttgctgtca agaaattttt ggaccaggac    3600
ttctcaggtg ctgctttagc cgagttcaga agcgaagtaa gccataagtt cacttgcgtt    3660
tatttactag tatacttagc tacccatta tttttttggt tgaacccaat ggcttacgtt    3720
gcagcttatt tgcttgcctt tgaattccca ctctattaat atttccctat ctgaaggtac    3780
ggattatgcg aagattgcgt catccaaatg ttgtattctt ccttggggct gttactcgtc    3840
ctccaaatct ttccatcgtc acagagtttc tgcctaggtt tgtcccatct tcttcttgtg    3900
aaagttaatt gcatatgaga ttttgagtc ctaaaagatt ctaatgtttt tttgctgttt    3960
tattatagag gaagcttgta tcgaatcctt catcggccca aatctcacat tgacgagcgg    4020
cgccggatta aatggccct tgacgtggta gaaaaataga ttcatatatc aacttccatg    4080
tcccccaggc ttatttcttc agaatagtca ctaaattcca gactattgtt actttcaggc    4140
aatggggatg aactgcttac acaccagtac accgacaatt gttcatcgtg atctcaaaac    4200
accaaacctt ttggttgata caactggaa tgttaaggta ggaagacttt ttcttaagt    4260 tgtccaacga atatacttgt ttactctaat ggtaaataaa tagattttgt ttttatctta    4320
ctaaccttgt aggtcggtga ttttgggttg tctcgcttaa agcacaatac ttttttatcc    4380
tccaaatcaa ctgctggaac ggtgagaacg cagaaccctt aaatctcttt acttttgat    4440 agaaatgcaa ctttcctact ggcatgcttg ttataatctg gggtacggct tcttctctaa    4500
tcacatgcat tgttaatttt accagcctga atggatggct ccagaagttc tacgcaatga    4560
gccctcaaat gaaagtgag tagcttatta gaagctcagt tctgttcttg gttctactag    4620
aaaatgttaa ggcagatact actctttact ttcccttttcc ctttttttcc aaggagatta    4680
aaaaaaatgt tggctgtttt tcgtcaggtg tgatgtgtac agtttcgggg taatactttg    4740
ggaactagca acattgagat taccatggag aggaatgaac ccaatgcaag tagttggagc    4800
agttgggttc cagaatcggc ggcttgagat ccccaaggaa cttgatcctg tggtgggaag    4860
gatcatcctg gaatgttggc aaacgtaagt gtcatgaaac aaactcaaaa cacttttaga    4920
atctgcgctg gttgaaaata tgtttggttt tatgttgggg cagggatccg aatctgcggc    4980
cgtcatttgc tcagctgacg gaagtgctga agcctttgaa ccggcttgta cttcctacac    5040
```

| | |
|---|---:|
| cacaatagat gtcatctgtg tgaatatgtg aaagaaaatt tggttaatgt atactatttg | 5100 |
| acctctggtg ctgcgcagag ttattataca taagccagcc tagaattgag gaatgtaaat | 5160 |
| gaaatcaatg tacactatac tacgttttga tgtattattt gttataggaa aagccgctat | 5220 |
| gctgtgctta ttttatcaga aataatgcta ataagttaaa cgtctgtc | 5268 |

<210> SEQ ID NO 39
<211> LENGTH: 3939
<212> TYPE: DNA
<213> ORGANISM: Arabidopsis thaliana

<400> SEQUENCE: 39

| | |
|---|---:|
| attttattgt aatttgttta ataataaaga attactgttt cctcccactt cccatctctc | 60 |
| ttttcctttt gtgttcttct tcttctccgc tttgtttccc caatctctct cttctctctc | 120 |
| tctgaagaaa aataaataaa agatctaact ttgacggctc tcttaatctt actcactccg | 180 |
| taagttccaa atctctctcc tttactctca tatctatatc gtccgaacaa aacccaggag | 240 |
| aattgcttca ccccctttt gggttttta tcattttctc agattctcag tttctgtttc | 300 |
| cgtcttctag attctgggtt cagtttctgt tttgctctta ttgaattttc ttattcattt | 360 |
| tgtgtttcgg agttattcat ggtagctgaa tttgttaatt ctgatgttgt tttgcgtttt | 420 |
| cttctttct agtttggcta tgtcgtcttt gatctgatgc tgggttattc tctttccctc | 480 |
| tgttttggtt tcttttaggg ttttaagtcg aatagactg atgggagctt gatggttatt | 540 |
| gttagatcag atgtggattt aaagccttcg ctgaactaac aagtctatgg aagaagcaaa | 600 |
| gacccttgtt ttacactgta tgttgtgagg aatttgtctg attttgggtg ataaaggtga | 660 |
| agtctttgag tttgtaattt tgagataaga ttggatggtg ggaagagagg atgcgatggg | 720 |
| gaatgatgaa gctcctcctg gttctaagaa aatgttttgg cggtctgcct cttggtctgc | 780 |
| ttcacggact gcatcacaag ttcctgaggg tgatgagcaa agcctgaaca ttccgtgtgc | 840 |
| tattagttct gggccgagtc gaagatgtcc agctgctcct ttgacacctc gttcacatca | 900 |
| taacagcaag gctagagctt gtttgccacc attgcagcct cttgccatt ctaggaggag | 960 |
| cttagacgag tggcctaagg cgggttcgga tgatgtcggt gagtggcctc atccaccaac | 1020 |
| acctagcggg aacaaaaccg gggagagatt gaagctcgat ttatcatcaa cgcagcagcg | 1080 |
| ggtaacagat aagagctctg gtctagctaa gagggagaag attgctttct ttgataaaga | 1140 |
| atgttcaaag gttgctgatc atatatatgt gggtggagat gctgtggcga aagacaagag | 1200 |
| catactgaaa aacaatggaa tcacgcatat cttgaactgc gttggtttat ctgtccggaa | 1260 |
| tatttcaagt ctgattttg ttacagatcc ttgtggttac aggatagtcc gtcagaggat | 1320 |
| ataactagta ttctgtacga tgtgtttgac tactttgaag atgtgaggga gcaaagtgga | 1380 |
| aggatctttg ttcattgttg tcaagggtt tcacgatcta cctcgttggt aatagcatat | 1440 |
| ctgatgtgga gagaagggca aagttttgat gatgcatttc agtatgtgaa gtctgctaga | 1500 |
| ggtattgctg atcctaacat gggctttgct tgccaattgt tacaatgcca aaagagggtt | 1560 |
| catgcgttcc cgcttagccc tacctcctta cttagaatgt acaaaatgtc tccacactct | 1620 |
| ccttatgacc ctttgcatct tgttccaaaa ctgttgaatg atccatgccc gggttctctg | 1680 |
| gattcaagag gtgcatttat cattcagtta ccttctgcaa tttacatttg ggttggtagg | 1740 |
| cagtgtgaaa ccatcatgga gaaagatgca aaagctgctg tttgtcagat tgctcgatat | 1800 |
| gagaaagtcg aagcacctat tatggtggtc agagaaggtg atgagcctgt ttattactgg | 1860 |
| gatgcatttg caagcatttt gcctatgatt gggggctcgg taattaaagt tcaaccaggt | 1920 |

```
gacaggaagg tcgacgcata taatctggat tttgagattt ttcagaaagc catagaggga      1980
ggttttgtgc caactttagc atcatccaac aacgaacatg agactcatct tcctgcaagg      2040
gaaaacagtt ggagctcact gaaatgtaag tttgcatcaa ggtttgacaa aggttttcgg      2100
tatgtctcca aaacgccact atctagggtc tattcagatt cgatgatgat cgtgcattca      2160
tcaggctcac cttcctcaac aacttcttca tcatccactg cgtcgcctcc ttttctctct      2220
cccgattctg tatgttcaac aaattcaggc aatagcttaa agagtttctc tcaatcctct      2280
ggacgttcgt ccttgagacc ttctattcca ccatcgctga cattgcctaa attttccagc      2340
ctatccctcc tcccttccca aacttctcct aaagaatctc gtggtgtcaa tacttttctt      2400
caaccgtcac caaatagaaa ggcttcacct tctcttgctg agcgtagagg cagcctgaaa      2460
ggatctctga agttgccagg tttggctgat tccaacagag gcacacctgc ttttacttta      2520
catccggatg atagtaatga catagtcttc aatctggagg gtattagaaa cggcgatcta      2580
tatccaccaa gtgattgcaa agggacaagt gtagattcag atttgccaga gaaggaaatt      2640
atatccttaa tcagttgcag taaatctgac agacacaaat cgggaggtga tactgatagc      2700
tctggccagc ctttagcatg tcgttggcca agtatggaga tgattacaaa actgagcaga      2760
gcttacttag attcagaatc tgttatagca atcccgttgc caagtgatgc tgtaggagaa      2820
acgggtagta ggaatttgta catttggatc ggaaagtcat tctctttgga taacaactgt      2880
tctctagtag atagcaacaa agcggcagac actgtggaga atgttgattg ggtacaaatt      2940
ggtgaatcca ttttgtgtca gatggacttg ccaaaagata cccctataaa ggtaataata      3000
gcctaaactt tggaggctct gatactttt actaattgta aagtctgcgt gctcatcttt       3060
gtcatgtctt atccaaccaa actatatttc gaagatgaaa attacaatct cagcactttc      3120
attactgact actgaggacg gttaggtaga atccttatga tttcagcagt tgtatgtatt      3180
ggtttattct ctagtggttt gcatggttcc aacttgttat gatccttttg ttgtttgtaa      3240
ctgataagtt gcttttcttt cttgttaaca gatagttagg gaatctgagg atcagacaga      3300
gttgctagca ctgctgagcg cgctataaca cccacccgca agctctacac atttactctg      3360
tttttttttc acagattcct tcaaccgcaa cacttttcca ttttcagaca gagtattcat      3420
tcagctcagg tgagaattct ctgaaagcag tctgtaacac ttcatcttca cagttgcatc      3480
cgaatacaat cgttagttct ggattatgtt taattgctat ctgatcatga atttgagtta      3540
gaggatggtt ggaacaaaaa aacttagaag ctcgaatgac cggttttttac caaattctca     3600
tagaccatat ttgattcttt tgatttactt ctggtgcagg actctctgtg cttatggaag      3660
ttgatgttgg gggaaacaac tctcttgtac agtggggaaa aaacttcttc ttcttctttc      3720
tatcacatga aaatcctcaa gggccattat tagtatgatc agattataaa attgtaaggt      3780
taggggcttt atgaggattt tgatggactt gttacaatgt ttacatatac actcagcagc      3840
acaatagatt tttgttaaac ttacatgtta ttcaagtaaa agtactatgt agatgttgaa      3900
gtctaattga agaattagtt aatgatagtc ttaaacact                             3939

<210> SEQ ID NO 40
<211> LENGTH: 1298
<212> TYPE: DNA
<213> ORGANISM: Arabidopsis thaliana

<400> SEQUENCE: 40
ctgtacaagt ggaattttga aaaagaagc agagagcgat ggagaaagtg gttgatctct         60
```

| | | |
|---|---|---|
| tcggagtcgg agaagctaat tcccagaagc tactcgaagg aggcaaagat ctcagcgaga | 120 | |
| tccaacaggt tttcttcgtt tctcttctct atctatccgt ctaatttcac acttggaatt | 180 | |
| tctcaggttt tggagtcttt aattccgaaa atcgtttgt tggatgagtt tattctcagg | 240 | |
| gattgttcat aggatcagta gctgaagcga ataacaagga ttttctcaaa agctctaata | 300 | |
| tcactcatgt cttaaccgtt gctgtggcct tggctcctcc ttatcctgat gattttgtct | 360 | |
| acaaagtcat tgaaggttgg gttttttttc ttcaatcctt agcctgtttt tgaaattttt | 420 | |
| cgtttagaga ttttataaac ttgttcttca tcgtgtagtg gttgatagat ccgagaccga | 480 | |
| tttgacagta tatttcgatg agtgttatag cttcatcgac caagctattc aatctggtgg | 540 | |
| tggtgtttg gttcattgct tcatgggaat gtctaggagg ttttgattct tttgccctta | 600 | |
| aatctcatac attcagttat tagatttagt gtttaagaat catcaatgtg aaccaattgc | 660 | |
| aaattatgta accatatcaa aaagtgtat ataaattgcc aactgagtaa ccataggaaa | 720 | |
| ctacagagac tcagattggc aaaagtgtat atgaatcttg tagtttgctt tgattctttt | 780 | |
| atagcttgct gattctggta ttagtaggag ttatggtagt gaacagatta catttgttg | 840 | |
| tggacaaatt aagagttttt cttgaacctg taatttgctt attgtgtcgt tctgttatat | 900 | |
| atatacttac acaatttgat tggtttgagt ttttctttga agtgtgacta tagtggtggc | 960 | |
| ttacctgatg aaaagcatg gaatgggatt ctctaaagct atggaacttg taaggagccg | 1020 | |
| acgacatcag gcatatccta atcccggttt catttcgcag ctccagcaat ttgaaaaatc | 1080 | |
| catccaaggt aatgcatgat tgcttcagct gataagaaga ttcaagatag tggcatgatg | 1140 | |
| aactctcatg aaattccggc aagtgtcttc agccccatgt tggccaaaaa agttgattgg | 1200 | |
| tttcgtgctg tgaaggattt ttttcttgtga actattgatg gtgagcactt tgccatgtcc | 1260 | |
| attagccaat tgaaatgaat gaaaacgcag aatttaca | 1298 | |

<210> SEQ ID NO 41
<211> LENGTH: 1994
<212> TYPE: DNA
<213> ORGANISM: Arabidopsis thaliana

<400> SEQUENCE: 41

| | | |
|---|---|---|
| accgttcaat aaaaaaaaaa gggtaaaggt agagacttta taacgaaatg tcaacaccca | 60 | |
| tcttctcgat tcctcaattt ctctagggtt cttcgttttc gttgttgtga ggaattttgc | 120 | |
| tccgatgtcg gcggagagtt gtttcggaag ctcgggtgat caaagcagca gcaaaggagt | 180 | |
| ggctactcat ggtggtagct atgttcagta taatgtctat ggcaatctct tcgaagtttc | 240 | |
| tagaaagtat gttcctcctc ttcgtcctat cggtagaggc gcttatggaa ttgtctggtg | 300 | |
| agttccaaaa ttaatcagat tgggtttttg aaacatgtaa tgttcacttc tgggggttctt | 360 | |
| agatttggga attagggttt tggaatctgt tgttattata ataacttgtg ttgataattg | 420 | |
| ttgatcagtg ctgctacaaa ctcagagact ggagaggagg tagctatcaa gaagattggt | 480 | |
| aatgcttttg acaatattat cgatgctaaa aggactttga gagagattaa gcttctcaag | 540 | |
| catatggatc atgaaaatgt acgtgttact aatcatcagc atctctggtt ttttttgtgt | 600 | |
| gaatcttata ttggtttatt gtgcaggtga ttgctgtaaa ggatataata aaaccaccgc | 660 | |
| agagagagaa cttcaatgat gtttacattg tttatgagct tatggacact gatctccacc | 720 | |
| aaattattcg ctctaaccaa cccttaactg atgatcattg tcgggtatgc atcaatctcc | 780 | |
| atcttgctta tatctagcag ctgaatcttc tgtttctact ttagaagcag ctgttattgt | 840 | |
| gttagagcat ctgatgagta ttgcttgata ctttataagt gagagctaat aaggatttcg | 900 | |

-continued

```
tttgttatgc tttgaagttg tgtttagtaa ttagtttcga ttatgttttg cagttttttc      960
tgtatcagtt gttgcgtggg ctcaaatatg ttcattcagc taatgtattg catcgagatt     1020
tgaaacctag caatttgctc ctgaatgcaa attgtgatct aaagcttggg gatttcgggc     1080
ttgcgaggac caaatccgag actgacttta tgactgaata tgttgttaca cgttggtatc     1140
gagctccaga gctgctactt aattgctctg aatacacagc agcaattgat atttggtctg     1200
tcggttgtat actcggtgaa acaatgacac gagagccctt gtttcccggt aaagattatg     1260
ttcatcagct tagactcatc actgaggtaa tctagtttag tatgtttcat ccaaagaatc     1320
accacttagt ctctcttcac ggtattaatg aatctttgga aagcagctta taggatctcc     1380
tgatgactca agcttgggat tcttaagaag tgacaatgca agaagatacg ttagacagct     1440
tccacagtac cctagacaga actttgctgc tagattccca acatgtcgg ctggtgcagt      1500
cgatttgctg gagaaaatgc ttgttttgta tccaagcaga cgcatcacag gtgagttata     1560
ttttatataa ctgcttctct gtttcttcgg ctatttctg aacatgtttt ttgtgtgtgt      1620
agttgatgag gcgttgtgcc acccatattt ggcgccgctg catgatatca acgaagaacc     1680
ggtatgtgtg aggccgttca attttgattt cgagcaacct actttgacag aagagaacat     1740
taaggagctt atataccgtg aaacagtcaa gttcaatcct caagactcag tgtgagagaa     1800
agagagagag atatatatcc ttaaaaggaa actcatcaaa atgctatgtt ttgttttgct     1860
ctgcttttgt tatcaaatct ctgataagtt tgataatatg tctgtaattt gaataacatc     1920
ctaaaaaatt ggaaaaaaag aaaagaacaa cctttgagct gtgttttgca atagagtgta     1980
tttaaatttc ctta                                                        1994
```

<210> SEQ ID NO 42
<211> LENGTH: 5742
<212> TYPE: DNA
<213> ORGANISM: Arabidopsis thaliana

<400> SEQUENCE: 42

```
agatctgagt ttatcagatt ccacgtacga tatgttcttt aaaagctcaa agattcacac       60
acatgcatgt cctgattctt tcggcttaca atttttgaga cattacggct tcttttgctg      120
atagaaccaa gactgatcaa gagtgacaaa gatgggtttt tataagatag aaatgtaaat      180
tgtagacttg gattcattag agaggagaag agatacattt ttttttttctt tacatgagag     240
atatgtaaaa tggtggtgtg ttattttgga agttaacata tgaatttctt ttgttaagat      300
tacttaaata atgatttagg aatggattag tagtttagta ccgttcatta cacgaagaca      360
agctaatctt ttgtctaatt aaaataaagc tgtctacatg aatcgaatcc agcgagataa      420
gttagttatt ttaagcgttg gttggaacac tttacatggc ttttcgtaga aatttcccca     480
agttgggttt tattaagacc aagaaaattc tagtctccta gactttttt tgtttctttt      540
gttaatttag tctcctaggc ttttcattc tatctgaaag caaatatgg ttatgcaatt       600
tggtttagcc aaaaaaacaa actaaatttt tctagtccgg ttcatgtaac ttcataatca     660
aacaagtaaa agtcgaatgt gacgcgtctt gccgaacgca aaacggacc aggcaagaag      720
gtgtagttag ttaattcggt taatattcag ctgagagaaa tcgaaccggt tccatatctt     780
gtagattatc cggtttactt tccggataag atttataagc aaaacagagt taaagtagta     840
gatttcttct atacgagacc aaatctgaaa acccaagtca agctacaaaa acttaactcc     900
aagcgaacaa atctcctcat tcattaaaca acaaaattgt tttccgacaa aaaagtgaat     960
```

-continued

```
atcactgagt tactgcgaaa tcccaaccga gagtgacatc tcaaaccaaa agatggagtc    1020
tatattaaag agacgaagac tccaaagtca agctacaaaa tttccaagca aagattacac    1080
agagaaaact ttccgaccaa atgtgaatgt ttatgaaagt ttctgcgaaa ctccagtcat    1140
gtcggatgta caaagccata aaccaatgta aaaccgacac gtggaaagct aagattccta    1200
gcttttcttt cttcatgagt ctccaatagc caaagagtca actccaaaaa aaaaacccat    1260
ttttgcattg aaatggtctc atgatggggt attttgggta actaattagt cctgtctaca    1320
tcttcccata aattaacaga gtaggagcgg attaagaag caagacgatt caaaagaaaa    1380
aagagagaag aaagtccact aaagaaaaga gaatagatat agatcaatgg cgtttgaagc    1440
tcttaccgga atcaatggtg atctaatcac cagatcatgg tcagcctcga agcaagctta    1500
cctaaccgag cgctatcaca aggaagaagc aggagcagtc gtaatcttcg ctttccaacc    1560
atctttctca gagaaagatt tcttcgatcc ggacaataaa tcttcctttg gagaaatcaa    1620
gttgaaccgt gttcagtttc cttgtatgag gaaaatcggt aaggtgatg tagctactgt    1680 taacgaagct ttcctcaaga atcttgaagc tgtcattgat ccaagaacct catttcaagc    1740
ttctgtaaga agattgaaaa catccgaata tattttttctt gttttttcct ttttggtctc    1800
ttatgctttt acttcttcag gtggaaatgg ctgtgaggag tagaaaacag atagtgttca    1860
caggacattc ctcaggaggt gcaactgcaa tcttagcaac agtttggtat ttggagaaat    1920
acttcatacg caatccaaat gtttaccttg agcctcgttg tgtgacattt ggagctcctt    1980
tggttggtga ctctatcttc agtcacgcac ttgggagaga aaaatggagc cggttctttg    2040
tgaactttgt cacaagattc gatattgtcc ctcggattac gcttgctcga aaggcgtctg    2100
tagaggaaac tttgcctcat gttcttgccc aattggatcc cagaaattct tcggtccaag    2160
agagtgaaca gagaataaca gagttttaca catcggtgat gcgagacaca tcaactgttg    2220
caaaccaagc tgtttgtgaa ttgactggaa gcgcagaggc gattttagag accctttcta    2280
gtttccttga gctaagtcct tatagacccg ccggtacttt tgttttctct acagagaaga    2340
gattggttgc agtgaacaac tcggacgcca ttcttcaaat gctgtttttac acttgtcaag    2400 ccagcgatga acaagaatgg tctctaattc catttcgaag tatcagagat catcatagct    2460
atgaggaact ggtacagtcg atgggaatga agttgtttaa tcatttggat ggagaaaact    2520
caatagagtc ttcgctcaat gaccttggag tggtaagtct ctctctctct ctctctctct    2580
ctctctctct ctctctcttt tcatactgtg cagctccata gctccattct tgcaatcatt    2640
taaacccttc agagtgtttc cttttttctgc agagcacaag aggcagacag tacgttcaag    2700
ctgcattaga ggaagagaag aaacgagtag agaatcagaa gaagattatt caggtttgtg    2760
gttgaaaagc ttgttcatga ataatgcagg tacgtgcttc gtctgtttgt gtctaacaac    2820
ataaaacttg ttggctctgt ggttttttagg tgatccagca agagaggttt ttaaagaaac    2880
tagcatggat agaagatgaa tacaagccaa agtgtcaagc ccataaaaat gggtattatg    2940
attccttcaa agtttcaaat gaagagaatg acttcaaagc aaacgtcaag agagctgagt    3000
tagccggtgt ttttgacgag gtgctcggtt tattgaagaa atgtcaactt ccagatgagt    3060
tcgaagggga catagattgg atcaagttag caactcgata ccgcagatta gttgagcctc    3120
ttgatattgc aaactaccat cgacatttaa agaacgaaga cacagggccg tacatgaaaa    3180
gaggaagacc aacccgctac atatatgctc agagaggcta cgaacatcat atactgaagc    3240 caaacgaat gattgcagaa gatgtatttt ggaacaaggt aaatggtctt aacttagggt    3300
tacagctaga ggaaattcaa gagactctaa agaattcggg atccgagtgc ggatcatgct    3360
```

```
tttgggctga ggttgaagaa ctcaaaggaa agccatacga ggaagttgag gtaagagtta    3420
agacattaga agggatgctt agagaatgga tcacagccgg ggaagtagat gagaaggaga    3480
tatttctgga gggttcaacg tttagaaagt ggtggatcac gcttcccaaa aatcacaaat    3540
cgcattctcc tctgcgagac tatatgatgg atgaaataac agatacctga accttaggtg    3600
gtggagtatt taagctatta gaacacttgc ttctcttaat ttgtgcaata agaaatgttt    3660
atcaatctgg tttccacttc atgatgatct tagaataaga aacatgttgt atgatcattg    3720
tgaagtaatg taatagctct ctattctaat gtcaaatttg gtttccactt tacagtgatc    3780
ttagaatata tacgttactc tactaaagcc taaagccatc tcaaatagca tgaaccagta    3840
acaaacaacc ttccttagat tgaaatggtc tcatgatggg gtattttggg taattactcc    3900
tgtctacatc ttcctactat attaacagag taggaggact aagaatcaag acgactcaaa    3960
agaaaaaaga gaagaaagtc cactcaagaa aagagaaatg gcgtttgaag ctcttacggg    4020
agtcaacggt gatctagtca ccatatcatg gatggcgtcg aagggagcta accaaacgga    4080
gcactatctc aaagaagaag taggaggaac cgttttttc gccttccgag catctttctc     4140
gtcggaagat ttgttcgcta cggagaatac atctcccttt ggagaaataa agatgaagcg    4200
taatcaattt ccttgtatga gaagcatcgg caacgacgtt gacgctactg ttaacgaagc    4260
tttcctcaag tcacttgaag ttctcattgg tccaagaacc tcatttcatg cttctgtaag    4320
taaacaaaag cttcttaaat gcgttttaaa tcgaaacat cagaataatt tgtgtctgaa     4380
acttactttc ttcaggtgca aagcgcggtt gatagaaaac aacaggttgt gttcacagga    4440
cattctttcg gaggcgcaac tgcaattcta gcaacagttt ggtatttgga gacatacttc    4500
atacgtgacg cctatgctgc ccctgagcct cgttgtgtga catttggagc tcctttggtt    4560
ggtgagagaa ttggagccgg ttttttcgtaa actttgttac aagattcgat attgtccctc    4620
ggattatgct tgctcggaag acaatgatgg agcaaaccct gtcttacgtt cttggcaaat    4680
tggattctac aagagctccg atccaagaga gcgaccaggt gataacagaa ttttacacaa    4740
gggtgatgcg agacacatat actgttgctt ccaaagctgt ctgtcagttg attggaaacg    4800
gagaagcgtt tttagaaact cttttctagtt tttatgagct aagtccttat agaccagtag    4860 gcactttgt cttctctaca cagaaaagat tggttgtagt gaacaactca gacgccattc       4920
ttcaaatgtt gttttacact tgtcagtcca acgacgaaca agaattgtct gtgattccat     4980
ttctaagcat tagagatcac catggctatg aggaactggt acaatccatt ggtattaagt    5040
tgcttaatca tttggatctg cataatccgc ttttggatgg agaaaactca ataggctccg    5100
ctctcgacga ccttggaatg gtaaatcttt ttctcttttc aatttgtgca gctccattag    5160
ctccatcctt atttatgttt cctttttgc agagcacaag agccagacag tgtattcatg     5220
ctgcattaga ggctgagaag caacgagtgg aaaatcagaa gaagatagaa accaaaagag    5280
atcaaatagt agaaagacta acttggatag tggaagtata caagccaaag tgtcaagctc    5340
ataaaaatgg gtattacgat tccttcaaag attcaaatga agagaatgac ttcaaagcaa    5400
acgtcaagag agtggagtta gccggtattt tcgacgaggt gcttggttta gtgaagaaag    5460
gtcagcttcc agatggattc gaggggagca gagactggat caatttagca actcaatacc    5520
gcagattaat tgaacctctt gatatttcaa actaccatgg gcagttaaag aacgaagaca    5580
cagggccgta catgttacat ggaagaccaa gccgctacaa atacgctcag agagggtacg    5640
aacatgatat attaaagcca actggaatga tcgcaaaaga tgtgtttgg agcaaggtaa      5700
```

```
atggtcttaa cttaggatta cagcaagaca ttcaagagat ct              5742
```

<210> SEQ ID NO 43
<211> LENGTH: 3033
<212> TYPE: DNA
<213> ORGANISM: Arabidopsis thaliana

<400> SEQUENCE: 43

```
ataaaaccag tacaatttta ctaaattatg atgttaaagt aagagacttt gaagaagacg    60
acttagcaaa gaccaaaacc aagaaattac ataggaacaa gccaagaaga tacatagata   120
atttcttttt gcttgtaata tatttacaac ttcataaaca tcatcgttct gcaactctct   180
actcgatatc caatcatgga cgattgtcga ttcgagacga gtgagttgca agcttcggta   240
atgatatcga ctcctttatt taccgattct tggagttcat gcaacaccgc aaattgcaac   300
gggagtataa agatccatga catcgccggg attacatacg ttgctatacc ggcggtatcg   360
atgattcagt tggggaatct tgtgggcttg ccagtcaccg agatgttct tttccccggc    420
ttatcctccg atgaacctct acctatggtc gacgctgcca tactcaaact ctttcttcag   480
ttaaaggttt gttttctctt cctctgtttt tttttctttc tattggatgc aatttaacct   540
atttattatc ttcaaggcat gtggatattt gaatttcaat taataatacc tcgagagaaa   600
aatacaaaaa tcattaaatg ctaatatggg aaattatttc acaaggatt ttaaaaaaaa    660
acaaaattct atcataagtt ttattcgttt ggatttgcga aaacgaattt tacctattaa   720
agttactatt ttttttacgt attttagtac tttttagtag aactgatgat cattactatt   780
ttttatttaa atatctctgt cctctgaatt ttgatgaatt ataatccaaa tggaggtttt   840
ttttgtcctt ttaaaagatt attataaact atcaccacca cctacccaa taggcaatag    900
acaatagata ataaataaaa attatttct tgtaagaaat tctaaaaaga ttcgtggaca    960
caattattcc aaatccacca tttggaatat gtcattgtcg cgaccttttgg atatcataag  1020
caagtcaatt gaaagtttgg tttgtatgcc atcacgtccg tccgcccaag tgatttaaaa  1080
aatttactaa ttagtgagtg aaacgtcatt ggtatttttg acaccaaaaa aaacaaaaaa  1140
tgttaatgga attggtagct ttacgcttta tgctttaaca cacctcggcg aagtttataa  1200
atgtgcgctc aaaaagtttt taacccatga ttattgtgtc accatcatgt attttattcc  1260
cttttttcgtc gaatactttt agttttgtt ttgtctctaa ggatatgaaa atcttgaaca   1320
aaaacaagtt cctattggtt ttgatgagta gaaaaaacaa gaagtgacca ttaatgtaga  1380
tataagttgt aaaaatggta agtctagaga ggtgtcttaa ctgattttta ttcaaatttg  1440
gttaaaccaa gtaattggca aatttagtct ctaaatcagt ttacattatt agaggaaatt  1500
gtacactcag aaggaaggta atctataatc agttttgttc ttgttagtca accaatttac  1560
agtaacgtcg actgcattaa cgtgcagatc aaggaaggat tggaattgga attgttaggt  1620
aaaaagctgg tggtgataac cggccattca accggcggcg cattggccgc tttcaccgca  1680
ctttggcttc tatctcaatc ttctccgccg tcattccgcg tcttttgtat cacctttggc  1740
tctcctctgc tcggaaacca atctctctcc acctcaattt cacgatcacg tttagcacac  1800
aacttctgcc acgtggtctc catccacgac ctcgttccta gaagcagcaa tgaacaattc  1860
tggcccttg gaacttactt gttctgttcc gacaaaggag gtgtctgtct agacaacgct  1920
ggttctgttc gtctgatgtt taatatcctc aacaccacag caactcaaaa caccgaggaa  1980
catcagaggt acggacacta tgtgttcaca ctttcacaca tgtttcttaa atctagaagc  2040
tttcttggtg ggagtatccc cgacaatagc taccaagctg gtgttgcgtt agccgttgaa  2100
```

-continued

```
gctctaggtt tctctaacga tgacacaagt ggcgttttag tcaaagaatg tatagaaaca    2160
gctacaagaa ttgttcgggc tcctattctg aggtcagctg agttagccaa tgagcttgct    2220
agtgtcttgc cagcaagact cgagattcaa tggtacaaag atcgttgcga tgcatcagaa    2280
gagcagctag gttactacga tttcttcaaa cgatattcgt tgaagagaga ctttaaagtg    2340
aacatgagtc gcataagact agctaagttt gggacacag tgattaaaat ggtggagacg     2400
aatgagttac ctttgattt tcatttagga agaaatgga tttacgcatc tcaattttat      2460
caactcttag ccgagccact cgacattgcg aatttctaca aaacagaga tataaagact     2520 ggcgggcatt acttggaggg aatagacct aaaaggtatg aggtgattga taaatggcag     2580
aaaggagtta aagtgcctga ggagtgtgtg agaagcagat acgcgagcac aacgcaagat    2640
acttgctttt gggctaagct tgagcaagca aaagagtgg tggatgaggc gagaaaagag     2700
agtagtgatc cccagaggag atctttgtta cgggaaaaga ttgttccatt cgagagttat    2760
gcgaatacat tggtgacgaa gaaggaggtt tcttttggatg ttaaagcgaa gaactcgagt   2820
tatagtgtgt gggaggcgaa tctgaaagag ttcaagtgca aaatgggtta tgaaaatgaa    2880
attgagatgg ttgttgatga gagtgacgca atggagactt agtaggacta atagcaaatc    2940
gaatgtttga tatgctatat aacaatctgt atcattgttg ttcatcatgt ttatgcaaga    3000
ctttctgatg aatgttacta tatattctaa aac                                 3033
```

<210> SEQ ID NO 44
<211> LENGTH: 1554
<212> TYPE: DNA
<213> ORGANISM: Arabidopsis thaliana

<400> SEQUENCE: 44

```
aatcatacaa accacaccaa gaggaaagaa aaataagata ccactcacca aaaacttcct    60
caaaactaac aaatggatac taataaagca aaaaagctta agttatgaa ccaactcgtt     120 gaaggccatg acttaacaac tcagcttcag caactcctct ctcaacccgg gtccggtcta    180
gaggatctag tggctaaaat cttagtgtgt ttcaataaca ccatctccgt tcttgatacc    240
ttcgaaccca tctcctcctc ctcatccctc gccgccgttg agggatctca aaatgcttca    300
tgtgataacg acggcaagtt tgaagattcc ggcgatagtc ggaaaagatt gggacccgtt    360
aagggtaaaa gaggatgcta caaaagaaag taagtttcgc ccttttctct ctcttactca    420
attattaacc ataatgatat aaaatcaatc catcgtagtt ctattagacc gattacgttg    480
atcatatgta ccatatatct agtgatcatc catactcatg gaaaaaacta tcatctagga    540
tttacttact gttatggtta gtcacaaaca aacaagacat ttagctttgg ttgcaagaat    600
cataagtagc caaatgatta attgatttca ttaatattat gagcagaaag agatcggaga    660
cgtgtactat agagtcgact atacttgagg acgcattttc ttggaggaaa tatggacaaa    720
aggagattct taatgccaaa ttcccaaggt ccttttttacc cctatatagt tttgtctata    780
tatattcgta tctgatatgt gacatgttgc cgggtattat tacacatgga ccgcaattat    840
atctaccata aatgtggtct gagcttaatt ggttgtgggc ttgaggcata tatattttgg    900
cctaaattat tttatttaa tttatgttgt gcagaagtta ctttagatgc acacacaagt    960 ataccccaagg gtgcaaggca acaaagcaag tccagaaggt tgagctcgaa cccaagatgt   1020
tcagtatcac atacatagga aaccacacgt gtaacaccaa cgcagaaact cccaagagca    1080
agacttgtga ccatcatgat gagatcttca tggattccga agatcacaag agtcctagtt    1140
```

| | |
|---|---:|
| tatctacctc aatgaaggaa gaagacaatc ctcatcgtca tcatggttcg tccacggaga | 1200 |
| atgacttgtc attggtgtgg ccagaaatgg ttttcgaaga agattatcat catcaggcca | 1260 |
| gttacgtcaa tgggaaaacg agtacatcta tcgatgtttt gggttctcag gatctcatgg | 1320 |
| tgtttggagg tggcggcgat ttcgagttta gcgaaaatga gcacttctct atcttcagtt | 1380 |
| catgttcgaa tctatcttga gtttaccact actataggac taagaccatg agttttaatc | 1440 |
| attaattagg ccatgtagag tggaaaacat ataatacata ttttgccctt ttctctaatg | 1500 |
| agtgtatgta ctgtacatat agtactataa ataaaactct tgctggatta aaac | 1554 |

<210> SEQ ID NO 45
<211> LENGTH: 1829
<212> TYPE: DNA
<213> ORGANISM: Arabidopsis thaliana

<400> SEQUENCE: 45

| | |
|---|---:|
| tcattcagtc ggaccaactt gtgaccgaag aaagcaaatt gagactacgc accaactagt | 60 |
| cctttggttt gtatcttaag ataaaggttt ctttatgga cggttcttcg tttctcgaca | 120 |
| tctctctcga tctcaacacc aatcctttct ccgcaaaact tccggtaagt ccggatttcg | 180 |
| tctgatccat tttcccgaaa tctaagttga ttttttgtatc ccttcaattt ctatgaactg | 240 |
| ggatttgggg aattaatcat gggttcattt caaattttcg tatttcagaa gaaggaggtc | 300 |
| tcagttttgg cttctactca cttaaagagg aaatggttgg agcaagacga ggttagttct | 360 |
| ttcgtcgaac acttggtgtg cactaccttc gacttcatat acttgttcga acattcagct | 420 |
| tttatcaatt ctttaacttc actttagtac tttacgaatc aattaagatg ggtctgagtt | 480 |
| tgaatgtctt tgcatcgaaa tgaatcggtg atgatgtagt tagtataaag tctgaaactt | 540 |
| tacataatca atcttgtttg gaacaaaaag gaagaatctt tttagtaatt tgatctttgt | 600 |
| ggtggtaatg aacagagcgc aagtgagtta cgagaggagc taaacagagt taattcagag | 660 |
| aacaagaagc taacagagat gttagctaga gtctgtgaga gctacaacga actacataat | 720 |
| catttggaga agcttcagag tcgccagagc cctgaaatcg agcagaccga tataccgata | 780 |
| aagaaaagaa aacaagaccc ggatgagttc ttaggctttc ctattggact cagtagtgga | 840 |
| aaaactgaga acagctccag caacgaagat catcatcatc atcatcagca acatgagcag | 900 |
| aaaaatcagc ttcttttcatg taaaagacca gtcactgata gcttcaacaa agcaaaagtt | 960 |
| tcgactgtct acgtgcctac tgaaacatcg gacacaagct tggtaaggga ttttgtctgt | 1020 |
| gaatcttttg attaaagagt catatgtttg aaattgcata gagacaaatg actaagcaga | 1080 |
| gtgtaactct gcagacagtt aaagatggat ttcaatggag gaaatacgga caaaaggtta | 1140 |
| caagagacaa cccgtcacct agagcttact ttagatgctc gtttgcaccg tcttgtccag | 1200 |
| taaaaaagaa ggtaatttac acacatcgag tttattgtat ttatagcttc atttgtaatt | 1260 |
| gtttatctct gcttgcttct tcagtttgtct aatgatctgt ggtattactg ttcaggtaca | 1320 |
| acgcagcgca gaggatccat ctttacttgt agcgacatac gaagggacgc ataaccactt | 1380 |
| gggtccaaat gcttctgaag gggatgctac aagccagggt gggtcaagca cagtgacttt | 1440 |
| ggatctggtt aatggctgtc atagactagc gttggagaaa aacgaaaggg ataatacgat | 1500 |
| gcaagaggtt ctgattcaac aaatggcgtc atcgttaaca aaagattcga aatttacagc | 1560 |
| tgctcttgct gctgctatat ctgggaggtt aatggagcaa tctagaacat gaacgttttt | 1620 |
| agtgaatgta ttgttttgt ttgtttagaa tgattcttcg ttttcgaatt gtgtctttcg | 1680 |
| attaggagat aaaagatgta tataaatatt ataagtagat gaagaaatcg tataagtatt | 1740 |

```
cgagaaactt taaatgtacg aattctatat aaccagttag atgtcgtctg aatactgtat   1800
atgaaaattt tgaaataaat gatgtggtt                                     1829

<210> SEQ ID NO 46
<211> LENGTH: 1985
<212> TYPE: DNA
<213> ORGANISM: Arabidopsis thaliana

<400> SEQUENCE: 46
ctcgaacttg tttttggttc atctctcaaa accaaaatca ctaaagagga gaagattgct     60
aaagtttgat aaaacattcc aaaatcaatg gctgatagga tcaaaggtcc atggagtcct    120
gaagaagacg agcagcttcg taggcttgtt gttaaatacg gtccaagaaa ctggacagtg    180
attagcaaat ctattcccgg tagatcgggg aaatcgtgtc gtttacggtg gtgcaaccag    240 cttcgccgc aagttgagca tcggccgttt tcggctgagg aagacgagac gatcgcacgt     300
gctcacgctc agtcggtaa taaatgggcg acgattgctc gtcttctcaa cggtcgtacg     360
gacaacgccg tgaagaatca ctggaactcg acgctcaaga ggaaatgcgg cggttacgac    420
catcggggtt acgatggttc ggaggatcat cggccggtta agatcggt gagtgcggga     480 tctccacctg ttgttactgg gctttacatg agcccaggaa gcccaactgg atctgatgtc    540
agtgattcaa gtactatccc gatattacct tccgttgagc ttttcaagcc tgtgcctaga    600
cctggtgctg ttgtgctacc gcttcctatc gaaacgtcgt cttcttccga tgatccaccg    660
acttcgttaa gcttgtcact tcctggtgcc gacgtaagcg aggagtcaaa ccgtagccac    720
gagtcaacga atatcaacaa caccacttcg agccgccaca accacaacaa tacggtgtcg    780
tttatgccgt ttagtggtgg gtttagaggt gcgattgagg aaatggggaa gtcttttccc    840
ggtaacggag gcgagtttat ggcggtggtg caagagatga ttaaggcgga agtgaggagt    900
tacatgacgg agatgcaacg gaacaatggt ggcggattcg tcggaggatt cattgataat    960
ggcatgattc cgatgagtca aattggagtt gggagaatcg agtagacaaa gtgagattat   1020
taggaaactg tttaaattgg agaagaagaa aaatgctctg ttttttttctc ctttggatta   1080 ggcttaagaa ttttgggttt taaggaaatg tatagaggaa atcgagtgaa caaagctcga   1140
gagctgggga cgtagtgacg aagacgaaga tcaaatttct cttaagctat tcaggaaaat   1200
aaaataaatt tttatttata actacgctta atgatgataa tagatcaaat taatacacaa   1260
agtatcacaa agtgaaagat aaatgatcca gttaaagaac aagtttgtcg aggattggta   1320
aagacttgca tttggcaact aaaggcacag atttgggcat ggtaagaccc tttccttccg   1380
acatgtcaac ggcaacgtca ttgtctctct cccaatcgaa acactggatc aatgagccta   1440
aagctaagct cagtactagt tgggccaggc ccataccagg acatgctctc ctaccgattc   1500
cgaaaggcag aaacttacca cgatgggtct ctgattcaaa cctctctggt ttgaaagttt   1560
ctgggtcatc ccatacattt gggtctctct gaatagccca cgcattgata aatagccagg   1620
tgcgacgtgg aatgtcaaat ccagcgactt cacagtcagt ggatgaagcg tgtgggacaa   1680
gtaagggcgc cgccggaaac aaacgaagag tctcagagat cacattgttg agataaggac   1740
acttgccagt atctgattcc tcaaacacac gcccttcttt cgaaacctcg tttagttccg   1800
ttttgagttt ccttaaaact tccggatgat ttagaaggtt agccatagcc cactccaacg   1860
tcactgcggt tgtgtccgtt ccagcaagca acatcacctg caatgaatcc tttgaatctt   1920
tgatgaatca atcttgatca ctcctattaa cgattcaaaa ttataggaat taaaaactca   1980
```

| | |
|---|---|
| tgtac | 1985 |

<210> SEQ ID NO 47
<211> LENGTH: 1503
<212> TYPE: DNA
<213> ORGANISM: Arabidopsis thaliana

<400> SEQUENCE: 47

| | |
|---|---|
| agacattaga cacggagaca ttgttgtcgt tcttcgcaga catttcgatt ttgaagacaa | 60 |
| atcacaatgg gagaagcgcc tgcccagatt ccgacgagtt tcggccacga gcttagggct | 120 |
| tgtcttcgat gccgcctcgt caagacctac gatcaggtct ggattctctt gtcacttgtg | 180 |
| atttgcgtgt ttcttctctt gcgaatattt tttgcctaat ctggtttctc caacagttta | 240 |
| gggattctgg atgcgagaac tgtcctttct caaaatagaa agacgatcat gaacgcatcg | 300 |
| tcgatgttac aactcccaac ttcaatgggt atggcttaaa ttcgaatcct tactttgaaa | 360 |
| atttacatgg cactgttcat aagtctgtct ctcgtacttg tcgttacatt gaaatttctg | 420 |
| aacctagtct atacttatga ttaaatcgta tagtctatac ttattgagaa gacttattgt | 480 |
| tggtcgctaa tctctcgttt ttttgttgaa tgagtcgttg caaattgtga atcactgtg | 540 |
| gtggatatga ccataaagtt tgctgcttta cgttaaaatg agttaatagt aacagagatg | 600 |
| atgctagtgt tgattatact tgtcatttgt tgatgtcacg tccatgtaat tatgtattga | 660 |
| tataatgaat gttttttgcag tataatctct atgatggatc cacgcagaag ttgggcagca | 720 |
| agatggttaa gaattggtat gtttcagctc tgtttcctga tcatcctcat tgtcttttag | 780 |
| agtttactat actgtgtagc ttcttctttc cgtttcctgt tattcttgtc tcaccattat | 840 |
| actttataaa tggggatatt agtgctgaat ttaactgtgt tgtctgcatc catttgagcg | 900 |
| gtagctgcat tctgatttgc tgtgtgttta tggcttgatg acctgatgtt gtattcccta | 960 |
| atattgccag ctttgtttca gacagaagag aaataaatct aacacattgc aatatcttgt | 1020 |
| ttccagggaa gtttgctcct ggttgctaca ctcttgctgt ctcagaggca ctcccagagg | 1080 |
| aaatgcaggt aaacatattt acttctctta gaaacctaag aagggattaa taagcaaatc | 1140 |
| cttagctctg ttttcgtatt gactgttcgt ctttttcaca tgtatgtggc ggaaatccgc | 1200 |
| tggcagttca tatgccaaca agcacgggtg cagtacgttc cacccaaacg tatttgaaac | 1260 |
| cttttgcagg ttgcagcaag tgtctccata ttagcatctc tgcaagtcgt cagtttcaag | 1320 |
| acaacttagt ccgatggagg ttatgaatgg aagtagttaa gttttatgta ctttgtttct | 1380 |
| gatttcaact aatatagaga gatttgatcc tcttattgtt atcaaaaact cttatttgat | 1440 |
| ccggaagata gagatagatt acatttttttt tttcaagtat ggaatggatt tcttttcctg | 1500 |
| tga | 1503 |

<210> SEQ ID NO 48
<211> LENGTH: 4585
<212> TYPE: DNA
<213> ORGANISM: Arabidopsis thaliana

<400> SEQUENCE: 48

| | |
|---|---|
| atgtctcagt actcagacga cgattattca catgaagatg actcggagat ggaggatgag | 60 |
| gacgaagaag acgaatatga acccagaagt agccgcaaag gaagatcagg gaagaaaagg | 120 |
| ggaagatcaa attcagattc cgatggtcgg cgagggagta aaagaagtc ttcgggctcc | 180 |
| gccttcattg actgggaggt tgaggtagat gacgacgtcg aagacgacga tgatgatgtg | 240 |
| gacgttgaag acggtaagca acagttgaaa tttgggggatt tttctctttg ttgaattcct | 300 |

```
tgattgaatt cgaaagttcc agttttatt gattttgaag tagaagaata tcacaaagtc    360
atctcctttg actatgaatt tgcaggtttc attgtaagtg gtgaagctga ccttcctaat    420
gaggattctg atcatcgtag gcaatattac caacggggt tcatcctca tgaagaagat     480 gtcgacgagt tggaaaagag aactttggaa agattgtcta cgaaatatgc aaaggatgat    540
tatgagcttg atgatgttaa cgacgttgat caacaagcgc ttttgccatc agtccgtgac    600
cctaaactgt ggctggtgaa atgtgcggta tgatttcttt cttgttatct cttaacttgg    660
atgtttgatt caattcagag cactgatgtt ttacaatgga atcacagatt ggacgtgaaa    720
gagaagttgc tgtttgtctt atgcaaaaaa tcgtagatag aggatcagag ttcaagatta    780
gatctgctat tgctcttgat catcttcaaa actatgtata tattgaagcg gatatggaag    840
ctcatgtgaa agaggtattt ttatggtttg tcctgttttc gtagcaatat tttgatgttt    900
tgactatagt ttgatgatat attttcctct gtggtatagg ctatcaaggg catgcggaat    960
atttatgcta atcagaagat tttgcttgtc cccataaaag aaatgactgc tgttctttct   1020
gtcgagagta aagcaatcga tttatcccgt gactcgtggg ttagaatgaa acttgggata   1080
tataagggtg atctagctca ggtacgatcc attttcatg tgttttaagt gttcagagtt    1140
ctctgaaacc tttctgaaat ttaagtttgg tacaggtggt tgatgttgat aatgtacgta   1200
agagggtcac agtcaagttg atcccaagaa ttgatctgca ggctctagcc aataagctgg   1260
tatacgacct ttttatactt aagtgtaaca atgctgtgt attgtgaaac atacttcttc    1320
ctatcttata tacttagggt atatgtagga aggaacagag aatgtcaaga agaaagcttt   1380
tgctccacct ccacgtttca tgaacattga tgaggcaagg tactgttcca gacttctggt   1440
gaaactatcc tatgtttttc taagcaataa ttgtgttctt tggttatgat ttatcagtat   1500
ttgtaacgtg attataggga acttcacata cgtgttgagc accggcgtga tccaatgacg   1560
ggtgactact ttgagaatat cggtggaatg cttttcaaag atggttttct ttacaagaaa   1620
gtatcgacga agtccattgc tgctcagaat gtaacaccaa ccttcgatga acttgaaaga   1680
ttcaagagac caaatgaaaa tggggagatc gacttcgttg atgagtcgac tttatttgca   1740
aatagaaaga agggtcattt catgaaaggt gatgcggtta ttgtgatcaa gggggatctt   1800
aaaaacttga agggctggat tgagaaagta gatgaagaga atgtccttat cagatcagag   1860
atgaaagatc ttcctgtaag tatccaaaat cttcatcttt tcataaacaa catatttgtt   1920
gctaaaatgt tgtagccagt aaaagactgt attcactgtt gcagaatcct attgcggtta   1980
atgggagaga gctttgtaaa tactttgaac ctggaaattt tgtgaaggtt gtgtctggca   2040
tccatgaagg aggaactggc atgattgtca agttgatca gcatatgctt atcattctgt    2100
ctgatacaac caagaacat gtaaggcata ttttgtttaa gttgtgtgtt aatttctgac    2160
aagggtaata taacgcatgg ggatgatatt ttatatgtag atttgcgtct cgctgatca    2220 tgttgccaag agtgcagaag tgactaaagg tgtcacaaaa attggggact atgaacttca   2280
tgatcttgtg attctaaggt aagttgaatg cgcccaacca cctctaattg atatcatttc   2340
tatcggtatg atagctttat attacacgat gcagtgactt tagctttgga gtaatcctaa   2400
aacttgatag tgaagctatc caggtaactt accaatcata caaatgcctc ttatcatgtc   2460
aatgctataa tgttattatt tatttcaaga tttgctgtaa ctccatttta tttcagattc   2520
ttaaaggggt tcctgacagc tcagaggtct ctattgtcaa agccagcgaa ataaaataca   2580
aaatttggaa gaaaatcaat gtgcaagacc gttacaaaaa tgtcgtcgcg gtgaaagatg   2640
```

| | |
|---|---:|
| ttgtcagggt cattgagggt cctagcaaag tgagttcctt tgcagtctgg tcgtttttt | 2700 |
| gttagcaaac tctttaaata tcatttgata agtcttatac cgatttatat atttgtgata | 2760 |
| gggtaaacaa ggtccagtgg tgcaaatcta caaaggagtg ttgtttatac atgaccggca | 2820 |
| taaccttgaa cacactggat ttatctgcac tagatgctca tcttgtgttc ttgctggtgg | 2880 |
| caatttcaag acaccagccc tggttcctcc atctccaagg agattccaac gggcagacat | 2940 |
| gggatataac cgtatgtcag atttcttcgt attattttgg ttctttattc ttgactcgtc | 3000 |
| cagtgcatgt taaagagggg ccccctacg tatgacttgt aaataggttt agtctgaaac | 3060 |
| tgttatgcgt aacttagaat gcattcgttt actgcagctg gagctggagg gagacatcag | 3120 |
| ggtggacgag ggagaagggg tgacgatcat ttggtaggta cttatgtcaa aattcgtctg | 3180 |
| gggccttttca aggatatag tgggcgttta gttgaagtca agataagct agtgcgtgtg | 3240 |
| gaacttgagg ccaagattgt gacaggcaag ctccactgta atttcacttc tattcacagc | 3300 |
| tggttgctga atgttgaatg aattctaact ctttttgtat gaacagttga gcggaaggcg | 3360 |
| atatcagata tgactgataa tgtagtcgca accccgcagt ataatatggg aagccaaact | 3420 |
| cctatgcatc cttcccggac tccacttcat ccctgtatga ctccaatgcg gcattctgga | 3480 |
| ggtttgtcac cttaatttcg cagtttcaag atccaatcat ttgtttgtgt ttttgtttct | 3540 |
| catttgacaa catgtttgat atgtttatgt aaaaaattca gctacaccta tccatgatgg | 3600 |
| aatgaggaca cctatgcgtg gtagagcttg gaatccttac atgcctatga gtcctcctag | 3660 |
| gtactttaac atggccactc ttcatttatt cccataaata tttcacattc tgagcaagtg | 3720 |
| tctcaaacca aaatatggtt gttgtgtctc agggataact gggaagatgg gaacccggga | 3780 |
| tcatggggaa caagtccata tgaagcagct acgcctggat cagattgggg tagtagtact | 3840 |
| cctggtcgta gtagttacag agatgccgga acaccaataa acaatggttt tgtctactac | 3900 |
| cttttatgcc ttaacggttt cttgctttga cgaatcttat tctcacacac ttttctcatg | 3960 |
| cagctaatgc cccaagtcct atgacaccaa gctcaacttc ctacttacct accacacccg | 4020 |
| gaggacaagc aatgactcct ggaaccgatc tcgatgtcat gtctcttgat ataggtgcct | 4080 |
| gcctatctct tagttttata ccattggtgt ttttgattct catattctta actctaccag | 4140 |
| gtggagatgc agaaaccagg ttcatacccg gtatattggt caatgtacac aaagctggag | 4200 |
| aggatagaaa tcccggtgtt attcgagatg ttcttccggt ttgtcctctt taaactacac | 4260 |
| agaagaatgt tgtattggag taaacatttt ccagtttact gattatgtaa gcctcttttt | 4320 |
| cctttgtggt catcatcagg atggctcctg tgtagtcgca cttggacaca gaggtgaagg | 4380 |
| cgagacgata agagcgacac agaacaaagt gagcctagtt tgtccgaaga agaacgaacg | 4440 |
| tgtgaagatt cttggaggca agtattgtgg ttcaacagct aaggtcattg gtgaggacgg | 4500 |
| tcaggacggt atagttaagc tagatgaaag tctcgatatc aagatattga agctgactat | 4560 |
| attagccaag ttagttcatg agtga | 4585 |

<210> SEQ ID NO 49
<211> LENGTH: 2754
<212> TYPE: DNA
<213> ORGANISM: Arabidopsis thaliana

<400> SEQUENCE: 49

| | |
|---|---:|
| aagatttcaa tctctccttc tcgttttctt ctttggtgct gctgagaaga aattagtgaa | 60 |
| attgtgaaag agaagatgtc gaaagagacg aagggtaata acaatacaag cagagtgatg | 120 |
| agtggctatg gcggtagctt ggaagctaac accttggcta tgattgattc caccggagct | 180 |

```
aaagacagtc gcgacgctaa cgaagatcgt acgtttcctc aattttcaat cttcgtcttt    240 gttttgtta  attgtattga tcctttgaat gaaaaacctt aggtttgcag tatctggaag    300
ctgttcgtgc tgcttcactt gtacccgaaa atggaattcc tccaaccaag taaaaaataa    360
aaaactctgt ttttctaaga aatttgaagt ttttacctct aaaagagtac tgattttgat    420
ttgggttttg tttaattttg aagcaaaatg taccaagcga ttttcaggat attgagattt    480
ggtaaaacat tggaacttat cacagcaagt ttccagcttt tgactcaatt acatcaggta    540
cttgttgcaa gattttggta gtgtaatttg tccataact  tttatgaggt ttcagtgttt    600
tgcttattat gattatgttt tgtttcagcg gtttccttgg gttatgtat  ctgattcagc    660 tgatcagttg gacatcgttg acgaggtact tgttacaaaa gttttgatgt gttttgttc    720 attctttgtt atggtgggga tggttgattt catgtgtttg tttatggttt tgttttgcag    780
gcttggtcac cgtttaattt cgggtctgat gttgattctg atgaaaagga tttatcagtg    840
agaagcttat gtaaggacgt ttgtcttctc tttttgagtt agcttttgt  tggttcttgc    900 taaatatgat ttttgtttg  ttttatgatt tcagttttgc aacagctgat tcagaacatg    960
aacaaaagag ttaatgagtc tgaggaatca gatttaaagg ttgatttatt tgttatgttg   1020
cagataagct ttaaaaattg gtagactttc acacaacttg ttgttatttg attctttgt   1080 ttggatttct gcagatcctt ggaaatatgt ttctgttcaa gtatcttgct catgttctta   1140
agctagattt cacaccccga aatcaagtgt atgaaggtat agattatgtc ttcatagttt   1200
taagatttct ctttatcttg ttaagtttgg ggaaattctt agaactttt  gtgtcctttt   1260 gtgctccaga aactatgaac tggagtctct taaaggaatc ttttctgaat ctacttctgg   1320
tacatcccac aatcaatggc tcagaaacta gtatagtaat ttatttgtga ttttaatgt   1380 tatggttctg cttgtaggct tcaagaaaag tgaatttcaa acttctaatg aaagattatc   1440
tatcaacaat gtgtgcatcc attgatgctg atgaaaagtc tatcagtttg gtagaattgc   1500
acaaggacat gcttactgct atgaaagaac ttctagtaat ggtaagtttt cggttaccag   1560
agtattagtg tttcaatttt cggagctttt tgctcttacg tttctgttcc ttgtttagat   1620
catggagctt gatacatcaa agaagaaagc tgacttagaa gggattacct ctagaggaga   1680
tggcgtaagg taatgagttt ctgcctcact tttgaattgt gttttctcca tgtttgtgat   1740
ccaatttgat gcaggacccc tgcaatggag atcattctcg acgagctgac ttatgatgga   1800
tacttgctgt caaatttct  tcaggtaaga gacaaaccac ttctgaaact cactgtggtc   1860
tgtaaaattc ttctctctgt ggttcttgag tgaaaatttc ttaatcaggt tttcgatgat   1920
cctaaatgga agctagagat tgttctccaa taccttacta aatacattcc taaggtttgt   1980
tgttaattct ctgatctctc gctctctgat tatcttctcc aacaaatgat gtacaatata   2040
tagttatttc tctgatttct ctctctgacc aaatttcttt catgttgtag cctgttgtac   2100
gtacccgaag aacaactgtt cctcaagcag aggattcgaa acactaaat  gggatcttga   2160 agacgttttc aaatggcaca aatccaaaga acatcactaa aaagatagga cctgacattg   2220
ttcagatcct catcggccat gcctttctgg taacacaata ataccttttgt ttcttctttc   2280 acgttctcag agctttttt  ggcctcctaa tgtatttaac tattcgtcag gctcggctta   2340
cattctctga ccctcacgaa ggagactcta tttcagagat atgcagtagt atcatctctg   2400
catttactag tctaaagcga gtagatcagt aagctgcagt ttctttcact ctcagttttt   2460
tttctctttg tgcaatcgag atactatacc gctttccttt gtccaaccga aagtttaatg   2520
```

-continued

| | |
|---|---|
| gttgttatag gaaaatcgag attctaccgt ttgggaaaga agtgttgttt actgcaggaa | 2580 |
| tggtactcaa ggcaaaagct taaagcatct aggaatcaag attttaacaa atctagagac | 2640 |
| ttcaattgga ttagaagcaa agaagttaca atgtaatgta ggaattaaga gttacagatc | 2700 |
| aatgaattat gaatttatat attctatagt tttgccaata caaaatgagt gatc | 2754 |

<210> SEQ ID NO 50
<211> LENGTH: 1895
<212> TYPE: DNA
<213> ORGANISM: artificial
<220> FEATURE:
<223> OTHER INFORMATION: first to third exon of WRKY6 gene

<400> SEQUENCE: 50

| | |
|---|---|
| atggacagag gatggtctgg tctcactctt gattcatctt ctcttgatct tttaaaccct | 60 |
| aatcgtattt ctcataagaa tcaccgacgt ttctcaaatc ctttggcgat gtctagaatt | 120 |
| gacgaagaag atgatcagaa gacgagaata tcaaccaacg gtagtgaatt taggtttccg | 180 |
| gtgagtctct caggtattcg tgatcgtgaa gatgaagatt tttcatctgg cgttgctgga | 240 |
| gataatgacc gtgaagttcc cggcgaagtg gatttcttct ccgacaagaa atctagggtt | 300 |
| tgtcgtgaag acgacgaagg atttcgtgtg aagaaggaag aacaagatga tcgaacggac | 360 |
| gtaaatgtaa gtacgacttt tcgataaatc atatgaaata caattttctt actaatggtt | 420 |
| tgtattagtg tggacgtgtc ataatttggt ttacatttga aatatcaaat aaaaatacca | 480 |
| aattttgttt cattttttt tttttgataa aggtatcata ttttgttttc ttacaaaatg | 540 |
| atttctaaat ttgaatttta atttgttata gaccggtttg aatcttcgaa caactggtaa | 600 |
| tacaaagagt gatgagtcaa tgatcgatga tggagaatct tccgaaatgg aagataagcg | 660 |
| tgcgaaaaat gaggtaagtt tagtttgatt ttacattagt aatatttaat agatgaataa | 720 |
| tttgaaccgg tttgattaat atttcgattt tttttgttt atcacagttg gtgaaattac | 780 |
| aagatgagtt gaagaaaatg acaatggata atcaaaagct tagagaattg cttacacaag | 840 |
| ttagcaacag ttacacttca cttcagatgc atcttgtttc actaatgcag caacagcaac | 900 |
| aacagaacaa taaggtaaat aattattaga ttgatcaacc acaagtaaat ggaatttacc | 960 |
| ctacatgaat aggcaattaa ttttggtgaa cctatatgat taggtaatag aagctgctga | 1020 |
| gaagcctgag gagacgatag taccaaggca atttattgat ttaggcccta cgagagcagt | 1080 |
| aggtgaggcc gaggatgtgt caaattcttc atccgaagat agaactcgtt cgggggggttc | 1140 |
| ttctgcagcc gagaggcgta gtaacgggaa gagacttggg cgtgaagaaa gccccgaaac | 1200 |
| tgagtccaac aaaattcaga aggtgaattc tactaccccg acgacatttg atcaaaccgc | 1260 |
| tgaagctacg atgaggaaag cccgtgtctc cgttcgtgcc cgatcggaag ctccgatggt | 1320 |
| aagttgattt attagatact aatacttata agactatata aaaaataaac tatgtgcttt | 1380 |
| agagattaat tatctttgta ctttatgttt ctatagataa gcgatggatg tcaatggaga | 1440 |
| aaatatggcc agaagatggc caaagggaat ccttgtccgc gggcatatta ccgctgcacg | 1500 |
| atggccacgg gctgtcccgt tcgcaaacaa gtaagattta aagatttaa ccattggact | 1560 |
| aaaagattct tgttgtaaaa acattagaga tttcaatgta tatatgtttg cgtgattggc | 1620 |
| taatacgttc ggtccgaaat gatatttata ggttcaacgt tgcgcggaag acagatcaat | 1680 |
| tctgattaca acctacgagg gaaaccataa ccatccgttg ccgccagccg cggtagccat | 1740 |
| ggcttctacc accacggcgg cggctaacat gttgctatcc gggtcaatgt ctagtcacga | 1800 |
| cgggatgatg aaccctacaa atttactagc tagggctgtt cttccttgct ccacaagcat | 1860 |

```
ggcaacaatc tcagcctccg cgccgtttcc aaccg                                    1895

<210> SEQ ID NO 51
<211> LENGTH: 31
<212> TYPE: DNA
<213> ORGANISM: artificial
<220> FEATURE:
<223> OTHER INFORMATION: WRKY6 forward promoter

<400> SEQUENCE: 51
tagatatctt cagaaacaaa cctcgcttgt c                                          31

<210> SEQ ID NO 52
<211> LENGTH: 37
<212> TYPE: DNA
<213> ORGANISM: artificial
<220> FEATURE:
<223> OTHER INFORMATION: WRKY6 reverse promoter

<400> SEQUENCE: 52
tagaattcga agtcttctgc cagaacataa gactctc                                   37

<210> SEQ ID NO 53
<211> LENGTH: 38
<212> TYPE: DNA
<213> ORGANISM: artificial
<220> FEATURE:
<223> OTHER INFORMATION: CHS 5' UTR forward primer

<400> SEQUENCE: 53
tagaattcac aacacaaatc agatttatag agagattt                                  38

<210> SEQ ID NO 54
<211> LENGTH: 38
<212> TYPE: DNA
<213> ORGANISM: artificial
<220> FEATURE:
<223> OTHER INFORMATION: CHS 5' UTR reverse

<400> SEQUENCE: 54
tacccgggtg ttttttttt tttataaat ctctctat                                    38

<210> SEQ ID NO 55
<211> LENGTH: 29
<212> TYPE: DNA
<213> ORGANISM: artificial
<220> FEATURE:
<223> OTHER INFORMATION: WAK1 ER localisation forward

<400> SEQUENCE: 55
tacccgggat gaaggtgcag gagggtttg                                            29

<210> SEQ ID NO 56
<211> LENGTH: 30
<212> TYPE: DNA
<213> ORGANISM: artificial
<220> FEATURE:
<223> OTHER INFORMATION: WAK1 ER localisation reverse

<400> SEQUENCE: 56
tagcggccgc aatgcccctt caccagctgc                                           30

<210> SEQ ID NO 57
<211> LENGTH: 32
<212> TYPE: DNA
```

```
<213> ORGANISM: artificial
<220> FEATURE:
<223> OTHER INFORMATION: WRKY 6 CDS forward

<400> SEQUENCE: 57
tagcggccgc atggacagag gatggtctgg tc                                32

<210> SEQ ID NO 58
<211> LENGTH: 30
<212> TYPE: DNA
<213> ORGANISM: artificial
<220> FEATURE:
<223> OTHER INFORMATION: WRKY6 CDS reverse

<400> SEQUENCE: 58
atacaccgcg gtgacggttg gaaacggcgc                                   30

<210> SEQ ID NO 59
<211> LENGTH: 32
<212> TYPE: DNA
<213> ORGANISM: artificial
<220> FEATURE:
<223> OTHER INFORMATION: mNeonGreen forward

<400> SEQUENCE: 59
atacaccgcg gtgatggtga gcaagggcga gg                                32

<210> SEQ ID NO 60
<211> LENGTH: 50
<212> TYPE: DNA
<213> ORGANISM: artificial
<220> FEATURE:
<223> OTHER INFORMATION: mNeonGreen reverse

<400> SEQUENCE: 60
ataagcggaa gagcttacaa ctcgtcatgc ttgtacagct cgtccatgcc             50

<210> SEQ ID NO 61
<211> LENGTH: 39
<212> TYPE: DNA
<213> ORGANISM: artificial
<220> FEATURE:
<223> OTHER INFORMATION: OCS forward

<400> SEQUENCE: 61
atagctcttc cgctctgctt taatgagata tgcgagacg                         39

<210> SEQ ID NO 62
<211> LENGTH: 35
<212> TYPE: DNA
<213> ORGANISM: artificial
<220> FEATURE:
<223> OTHER INFORMATION: OCS reverse

<400> SEQUENCE: 62
ataagcggaa gagcctgctg agcctcgaca tgttg                             35

<210> SEQ ID NO 63
<211> LENGTH: 1346
<212> TYPE: DNA
<213> ORGANISM: Arabidopsis thaliana

<400> SEQUENCE: 63
acgacgttgg actgtttcat catatcccat aaaaatacat gattggggtg aaaatcttga  60
acatattaaa aaaatattaa atcaaaatga taaagatagg gatttataaa tgtaaaacgg  120
```

```
gcgtgtcgag aatttatgg acattgggac aagctttata tgcagcatgc atcgccgcat      180
cgatatcccg aggtgcatcg tttctacttt catgtccaaa tttggggtta actcacaata      240
tatatcatgt tgcctatgta aatttataat cataaatcta aacccaaatt ttaatcctca      300
ttccaaagca aaagttctaa gccctacaaa atatgtatt tcccaagttt aaaaagaatt       360
aatctatact tttacaaatt taaattctga tctcttataa tgttcggttt ttcctttttt      420
atttattaag ttagttaaaa tttgcagtta ttttgttgaa tgtcgttgtt tacgaattta      480
cgaataatac ctttatagct aatctacaaa attttgatga ctgacaacac cgttaatgtt      540
tttttttaaa ttaccctgag cctctcactt gcggtcagac catgcatgtc gatagtccat      600
tacgtttaag gccacaatca actatagttt gtttatcaat agccaactaa gctaactttt      660
aggttcctgc cctctccgtt cctccggtac caatcgtttc tttgtccctt cgatagtttg      720
aaaacctacc gacggtgaga gcaaaatatt gatgaatcat ccaattttca gtaataggtg      780
tgtcccaggg atatataaat ggcgaaacta cgcgagaacg gttccttgtt ctgcaaactt      840
ggcggaacaa tgctgctctt gagatcaacc aaaccatatg tttagtccac aacgatctat      900
atgtctaggg gtgatcctct aatcgaaaaa tgttgtattt gttcgacgat gacgaaggtc      960
agactatgaa ctgcacagtc tgcacttgtc ctaaccgcga gaatctctga catcaatata     1020
cttgtgtaac tatggcttgg ttaagatatt attttcttga gtcttaatcc attcagatta     1080
accagccgcc catgtgaacg atgtagcatt agctaaaagc cgaagcagcc gcttaggtta     1140
ctttagatat cgacagagaa atatatgtgg tggagaaacc agccatcaac aaacaaaaag     1200
caagatctta tcttttgata ttggctacgg gaagatgatg tctgtttaat gtgtggggtt     1260
accacgttat tgtacgatgc acaagtagaa gattaaccca ctaccatttc attataaata     1320
gacgttgatc tttggcttat ttcttc                                          1346

<210> SEQ ID NO 64
<211> LENGTH: 2000
<212> TYPE: DNA
<213> ORGANISM: Arabidopsis thaliana

<400> SEQUENCE: 64 tttatttag taactttca ataagtggag ctaaatgaca tgagatggtt aacaatcgta        60 aaccaacaa acggaagatt agtagtgcgg atcttttgt atcaatgtaa ctcgaagacc       120
aattattgtc gtgcgtatat ataaggttgg cctcaacagg atccaattgg tgtttagtgt     180
ctatttcttt ctttttttaat aaggttggcc tggcctcaat tattgttttt ttttatttct    240
aatattacat ttatcaattt ttggtgtttt ttcggtgaaa cacaaatgaa aaaactttaa     300
atagatcaag gtaatgtggg tggtggaaag ggcaagagca tgtggataat gtagagttgt     360 tggggacaa tattttaatg aattccgagt aaattaataa tgtctttaat atgtatgctc      420
cattattgat gctttacgct gtcatcgaca tccattgcct caacaaacaa tggttgataa     480
tgatgatatt tgttttattt attatttatc tgattttta gtaaatttga tctagttgt       540 atccttggtt gtcaaattca ccacatgtat ttacttgttt gtagaatact tagttcaata     600
taaattggct gattttgctc tcgttgtgaa ttacaacttg taacttaaca agtacaaaat     660
gcacaaaaga tggttctcaa aaaacagatt cacaaaagat gattacaaga agatgaaaga     720
tacacaaaaa taaacaagaa gcacagcttc gtcccaacaa taattaagta atttgggggg     780
aaaaacattt tgggccatgg ttaacactag ggaaaaaaaa ttggggcctt acattttctc     840
```

```
ataataatgg gcttttcatc aatttcttta aatattaatg ggcctttggc ccgataacag      900
ctaccctatc catttggtcc gggcactcta gaatactctc ttcgctcttc tctttctctc      960
gtgtactctg ttttatccaa cttataacaa tttgaagcgg acttgatatg ggctcagttt     1020
cggtaaacca aacccgtatt gcccgttaag cccatagaca aacaattcaa gttgactttg     1080
actgaagtca acacttaaag atctgtaggc tcgccagccc agtctctata ctattttaga     1140
tcaaagctga aaattcatct cgtgtcaata agaaaaatt acgaggaagc ggatagattt      1200
gcttttttac ttacgcatca tagaagaaat ttgttaaact gctaagtgag ttttgagaaa     1260
caaaatttta aataatccaa aatggctaat tcaatggacc gattatgtta actttgatta     1320
gtcaatgatc gaaattcaat atttatccaa atgagagcga ctcttatcta ctaggctgct     1380
attttctaca aacaaacaaa aacaatcaca attagccgcc tctcctcatt agtcattatc     1440
tgtatcgcga tggggaagat acgcaatgct tagttataaa ccgtccgatc agatgacttt     1500
gaccagtgac cttccgttca agaatatcg acggttctta gacacatttt tcaccggagt      1560
ctcaccctca caggtcatct taatttctcg taaaagagca tattacattg atattccaaa     1620
ttataccact tcataattta ttttatttt ccaaataaaa ttaatttatt aaaacttcag      1680
cactccaatt ctgtagagaa attttaagag gagaaaccca attttctttt attttgtaac     1740
gaatctcttt taaaaaaatc taacaacaga attatatatt ttcattattc tatcgaatcc     1800
aacgaaattt caatatacag atatctatat acaaatattt aacctacatg tgtgtatcat     1860
atggtttaag cacgttacct gtaacgtatg taattaaatc aattgcgtag aatcacaaga     1920
aaaacattat tatataatta actattgatc ctataatttt attattttca tatatatata     1980
gatatataga tagatgcatt                                                  2000
```

<210> SEQ ID NO 65
<211> LENGTH: 4448
<212> TYPE: DNA
<213> ORGANISM: artificial
<220> FEATURE:
<223> OTHER INFORMATION: pGreenII-0229 plasmid

<400> SEQUENCE: 65

```
agctctcatc aaccgtggct ccctcacttt ctggctggat gatggggcga ttcaggcgat       60
ccccatccaa cagcccgccg tcgagcgggc ttttttatcc ccggaagcct gtggatagag      120
ggtagttatc cacgtgaaac cgctaatgcc ccgcaaagcc ttgattcacg ggctttccg       180 gcccgctcca aaactatcc acgtgaaatc gctaatcagg gtacgtgaaa tcgctaatcg      240
gagtacgtga atcgctaat aaggtcacgt gaaatcgcta atcaaaaagg cacgtgagaa      300
cgctaatagc ccttcagat caacagcttg caaacacccc tcgctccggc aagtagttac     360
agcaagtagt atgttcaatt agcttttcaa ttatgaatat atatatcaat tattggtcgc     420
ccttggcttg tggacaatgc gctacgcgca ccggctccgc ccgtggacaa ccgcaagcgg     480
ttgcccaccg tcgagcgcca gcgccttgc ccacaacccg gcggccggcc gcaacagatc     540
gttttataaa ttttttttt tgaaaagaa aaagcccgaa aggcggcaac ctctcgggct      600
tctggatttc cgatccccgg aattagagat cttggcagga tatattgtgg tgtaacgtta     660
tcagcttgca tgccggtcga tctagtaaca tagatgacac cgcgcgcgat aatttatcct     720
agtttgcgcg ctatattttg tttttctatcg cgtattaaat gtataattgc gggactctaa     780
tcaaaaaacc catctcataa ataacgtcat gcattacatg ttaattatta catgcttaac     840
gtaattcaac agaaattata tgataatcat cgcaagaccg gcaacaggat tcaatcttaa     900
```

```
gaaactttat tgccaaatgt tgaacgatc tgcttgactc tagggtcat cagatttcgg        960 tgacgggcag gaccggacgg ggcggcaccg gcaggctgaa gtccagctgc cagaaaccca     1020
cgtcatgcca gttcccgtgc ttgaagccgg ccgcccgcag catgccacgg ggggcatatc     1080
cgagcgcctc gtgcatgcgc acgctcgggt cgttgggcag cccgatgaca gcgaccacgc     1140
tcttgaagcc ctgtgcctcc agggacttca gcaggtgggt gtagagcgtg gagcccagtc     1200
ccgtccgctg gtggcggggg gagacgtaca cggttgactc ggccgtccag tcgtaggcgt     1260
tgcgtgcctt ccagggaccc gcgtaggcga tgccggcgac ctcgccgtcc acctcggcga     1320
cgagccaggg atagcgctcc cgcagacgga cgaggtcgtc cgtccactcc tgcggttcct     1380
gcggctcggt acggaagttg accgtgcttg tctggatgta gtggttgacg atggtgcaga     1440
ccgccggcat gtccgcctcg gtggcacggc ggatgtcggc cgggcgtcgt tctgggctca     1500
tggtagatcc ccctcgatcg agttgagagt gaatatgaga ctctaattgg ataccgaggg     1560
gaatttatgg aacgtcagtg gagcattttt gacaagaaat atttgctagc tgatagtgac     1620
cttaggcgac ttttgaacgc gcaataatgg tttctgacgt atgtgcttag ctcattaaac     1680
tccagaaacc cggctgagtg gctccttcaa cgttgcggtt ctgtcagttc caaacgtaaa     1740
acggcttgtc ccgcgtcatc ggcggggggtc ataacgtgac tcccttaatt ctcatgtatc   1800
gataacatta acgtttacaa tttcgcgcca ttcgccattc aggctgcgca actgttggga     1860
agggcgatcg gtgcgggcct cttcgctatt acgccagctg gcgaaagggg gatgtgctgc     1920
aaggcgatta agttgggtaa cgccagggtt ttcccagtca cgacgttgta aaacgacggc     1980
cagtgaattg taatacgact cactataggg cgaattgggt accgggcccc ccctcgaggt     2040
cgacggtatc gataagcttg atatcgaatt cctgcagccc gggggatcca ctagttctag     2100
agcggccgcc accgcggtgg agctccagct tttgttccct ttagtgaggg ttaattccga     2160
gcttggcgta atcatggtca tagctgtttc ctgtgtgaaa ttgttatccg ctcacaattc     2220
cacacaacat acgagccgga aghcataaag tgtaaagcct ggggtgccta atgagtgagc     2280
taactcacat taattgcgtt gcgctcactg cccgctttcc agtcgggaaa cctgtcgtgc     2340
cagctgcatt aatgaatcgg ccaacgcgcg gggagaggcg gtttgcgtat tgggcgctct     2400
tccgcttcct cgctcactga ctcgctgcgc tcggtcgttc ggctgcggcg agcggtatca     2460
gctcactcaa aggcggtaat acggttatcc acagaatcag gggataacgc aggaaagaac     2520
atgaaggcct tgacaggata tattggcggg taaactaagt cgctgtatgt gtttgtttga     2580
gatctcatgt gagcaaaagg ccagcaaaag gccaggaacc gtaaaaaggc cgcgttgctg     2640 gcgttttttcc ataggctccg ccccctgac gagcatcaca aaaatcgacg ctcaagtcag    2700
aggtggcgaa acccgacagg actataaaga taccaggcgt ttccccctgg aagctccctc     2760
gtgcgctctc ctgttccgac cctgccgctt accggatacc tgtccgcctt tctcccttcg     2820
ggaagcgtgg cgctttctca tagctcacgc tgtaggtatc tcagttcggt gtaggtcgtt     2880
cgctccaagc tgggctgtgt gcacgaaccc cccgttcagc ccgaccgctg cgccttatcc     2940
ggtaactatc gtcttgagtc aacccggta agacacgact tatcgccact ggcagcagcc      3000
actggtaaca ggattagcag agcgaggtat gtaggcggtg ctacagagtt cttgaagtgg     3060
tggcctaact acggctacac tagaagaaca gtatttggta tctgcgctct gctgaagcca     3120
gttaccttcg gaagaagagt tggtagctct tgatccggca acaaaccac cgctggtagc      3180 ggtggttttt ttgtttgcaa gcagcagatt acgcgcagaa aaaaggatc tcaagaagat      3240
```

-continued

| | |
|---|---|
| cctttgatct tttctacggg gtctgacgct cagtggaacg aaaactcacg ttaagggatt | 3300 |
| ttggtcatga gattatcaaa aaggatcttc acctagatcc ttttaaatta aaaatgaagt | 3360 |
| tttaaatcaa tctaaagtat atatgtgtaa cattggtcta gtgattagaa aaactcatcg | 3420 |
| agcatcaaat gaaactgcaa tttattcata tcaggattat caataccata tttttgaaaa | 3480 |
| agccgtttct gtaatgaagg agaaaactca ccgaggcagt tccataggat ggcaagatcc | 3540 |
| tggtatcggt ctgcgattcc gactcgtcca acatcaatac aacctattaa tttcccctcg | 3600 |
| tcaaaaataa ggttatcaag tgagaaatca ccatgagtga cgactgaatc cggtgagaat | 3660 |
| ggcaaaagtt tatgcatttc tttccagact tgttcaacag gccagccatt acgctcgtca | 3720 |
| tcaaaatcac tcgcatcaac caaaccgtta ttcattcgtg attgcgcctg agcgagacga | 3780 |
| aatacgcgat cgctgttaaa aggacaatta caaacaggaa tcgaatgcaa ccggcgcagg | 3840 |
| aacactgcca gcgcatcaac aatatttttca cctgaatcag gatattcttc taatacctgg | 3900 |
| aatgctgttt tccctgggat cgcagtggtg agtaaccatg catcatcagg agtacggata | 3960 |
| aaatgcttga tggtcggaag aggcataaat tccgtcagcc agtttagtct gaccatctca | 4020 |
| tctgtaacaa cattggcaac gctacctttg ccatgtttca gaaacaactc tggcgcatcg | 4080 |
| ggcttcccat acaatcggta gattgtcgca cctgattgcc cgacattatc gcgagcccat | 4140 |
| ttatacccat ataaatcagc atccatgttg aatttaatc gcggccttga gcaagacgtt | 4200 |
| tcccgttgaa tatggctcat aacacccctt gtattactgt ttatgtaagc agacagtttt | 4260 |
| attgttcatg atgatatatt tttatcttgt gcaatgtaac atcagagatt ttgagacaca | 4320 |
| acgtggcttt gttgaataaa tcgaacttttt gctgagttga aggatcagat cacgcatctt | 4380 |
| cccgacaacg cagaccgttc cgtggcaaag caaaagttca aaatcaccaa ctggtccacc | 4440 |
| tacaacaa | 4448 |

<210> SEQ ID NO 66
<211> LENGTH: 708
<212> TYPE: DNA
<213> ORGANISM: artificial
<220> FEATURE:
<223> OTHER INFORMATION: octopine synthase terminator

<400> SEQUENCE: 66

| | |
|---|---|
| ctgctttaat gagatatgcg agacgcctat gatcgcatga tatttgcttt caattctgtt | 60 |
| gtgcacgttg taaaaaacct gagcatgtgt agctcagatc cttaccgccg gtttcggttc | 120 |
| attctaatga atatatcacc cgttactatc gtatttttat gaataatatt ctccgttcaa | 180 |
| tttactgatt gtaccctact acttatatgt acaatattaa aatgaaaaca atatattgtg | 240 |
| ctgaataggt ttatagcgac atctatgata gagcgccaca ataacaaaca attgcgtttt | 300 |
| attattacaa atccaatttt aaaaaaagcg gcagaaccgg tcaaacctaa aagactgatt | 360 |
| acataaatct tattcaaatt tcaaaagtgc cccaggggct agtatctacg acacaccgag | 420 |
| cggcgaacta ataacgctca ctgaagggaa ctccggttcc ccgccggcgc gcatgggtga | 480 |
| gattccttga agttgagtat tggccgtccg ctctaccgaa agttacgggc accattcaac | 540 |
| ccggtccagc acggcggccg ggtaaccgac ttgctgcccc gagaattatg cagcattttt | 600 |
| ttggtgtatg tgggccccaa atgaagtgca ggtcaaacct tgacagtgac gacaaatcgt | 660 |
| tgggcgggtc cagggcgaat tttgcgacaa catgtcgagg ctcagcag | 708 |

<210> SEQ ID NO 67
<211> LENGTH: 7

```
<212> TYPE: PRT
<213> ORGANISM: Artificial sequence
<220> FEATURE:
<223> OTHER INFORMATION: Artificial heptapeptide repeat

<400> SEQUENCE: 67

Tyr Ser Pro Thr Ser Pro Ser
1               5
```